US010252856B2

(12) United States Patent
Michaels et al.

(10) Patent No.: US 10,252,856 B2
(45) Date of Patent: Apr. 9, 2019

(54) FLUID COLLECTION AND DISPOSAL SYSTEM HAVING INTERCHANGEABLE COLLECTION AND OTHER FEATURES AND METHODS RELATING THEREOF

(71) Applicant: ALLEGIANCE CORPORATION, McGaw Park, IL (US)

(72) Inventors: Thomas L. Michaels, McCullom Lake, IL (US); Russ A. Johnson, Spring Grove, IL (US); Adam S. Fedenia, Libertyville, IL (US); Wen Tang, Waukegan, IL (US); Frank Garrett, Barrington, IL (US); Otakar Kudrna, Burr Ridge, IL (US)

(73) Assignee: ALLEGIANCE CORPORATION, McGaw Park, IL (US)

( * ) Notice: Subject to any disclaimer, the term of this patent is extended or adjusted under 35 U.S.C. 154(b) by 641 days.

(21) Appl. No.: 13/908,708

(22) Filed: Jun. 3, 2013

(65) Prior Publication Data
US 2013/0341330 A1     Dec. 26, 2013

Related U.S. Application Data

(62) Division of application No. 12/076,842, filed on Mar. 24, 2008, now Pat. No. 8,500,706.
(Continued)

(51) Int. Cl.
*A61M 1/00*     (2006.01)
*B65F 1/06*     (2006.01)
(Continued)

(52) U.S. Cl.
CPC ............. *B65F 1/06* (2013.01); *A61M 1/0001* (2013.01); *A61M 1/005* (2014.02);
(Continued)

(58) Field of Classification Search
CPC ........ A61M 1/00; A61M 25/00; A61M 27/00; A61F 13/02; A61J 1/00; A61J 1/05; A61J 1/10; A61J 1/16
See application file for complete search history.

(56) References Cited

U.S. PATENT DOCUMENTS

| 687,790 A | 12/1901 | William |
| 1,703,834 A | 2/1929 | Thompson |

(Continued)

FOREIGN PATENT DOCUMENTS

| CN | 1199192 | 11/1998 |
| CN | 1199192 A | 11/1998 |

(Continued)

OTHER PUBLICATIONS

Baatz, S. et al., Hand off Support for mobility with IP over Bluetooth, Univ of Bonn, Inst. of Computer Sci IV (2000 IEEE), pp. 143-154.
(Continued)

*Primary Examiner* — Tatyana Zalukaeva
*Assistant Examiner* — Ilya Treyger
(74) *Attorney, Agent, or Firm* — Jacob R. Lenzke

(57) ABSTRACT

Various implementations of a fluid collection system having a flexible liner are disclosed. In one exemplary variation, the fluid collection system may include a container having a top opening, a lid configured to close the top opening, and a flexible liner attached to the lid. The liner may be interposed between the lid and the container when the lid closes the top opening. The liner and the lid may define a substantially sealed interior space therebetween. The lid may include an access port through which the interior space receives fluid. The flexible liner may also be configured to controllably collapse as the fluid is removed from the interior space.

21 Claims, 47 Drawing Sheets

Related U.S. Application Data

(60) Provisional application No. 60/919,607, filed on Mar. 23, 2007, provisional application No. 60/963,325, filed on Aug. 3, 2007.

(51) Int. Cl.
  *B08B 9/08* (2006.01)
  *A61M 25/00* (2006.01)
  *A61M 27/00* (2006.01)
  *A61F 13/02* (2006.01)

(52) U.S. Cl.
  CPC ........ *A61M 1/0005* (2013.01); *A61M 1/0009* (2013.01); *A61M 1/0017* (2014.02); *A61M 1/0052* (2014.02); *B08B 9/08* (2013.01); *A61M 2205/7536* (2013.01)

(56) References Cited

U.S. PATENT DOCUMENTS

| | | |
|---|---|---|
| 2,057,238 A | 10/1936 | Krug |
| 2,452,503 A | 10/1948 | Teetor |
| 2,686,625 A | 8/1954 | Sundholm |
| 3,035,623 A | 5/1962 | Goetz |
| 3,164,186 A | 1/1965 | Weber et al. |
| 3,164,600 A | 1/1965 | Janssen |
| 3,307,746 A | 3/1967 | Edwards |
| 3,397,648 A | 8/1968 | Henderson |
| 3,515,127 A | 6/1970 | Reymond |
| 3,537,455 A | 11/1970 | Skyles et al. |
| 3,680,560 A | 8/1972 | Pannier, Jr. et al. |
| 3,719,197 A | 3/1973 | Pannier et al. |
| 3,745,999 A | 7/1973 | Deaton |
| 3,768,478 A | 10/1973 | Ashley et al. |
| 3,773,211 A | 11/1973 | Bridgman |
| 3,780,738 A | 12/1973 | Deaton |
| 3,782,414 A | 1/1974 | Holbrook |
| 3,804,090 A | 4/1974 | Holbrook |
| 3,805,788 A | 4/1974 | Kleiner |
| 3,814,098 A | 6/1974 | Deaton |
| 3,830,238 A | 8/1974 | Kurtz et al. |
| 3,843,016 A | 10/1974 | Bornhorst et al. |
| 3,878,962 A | 4/1975 | Holbrook et al. |
| 3,915,189 A | 10/1975 | Holbrook et al. |
| 3,924,772 A | 12/1975 | Magnani |
| 3,945,392 A | 3/1976 | Deaton et al. |
| 4,014,329 A | 3/1977 | Welch et al. |
| 4,015,603 A | 4/1977 | Kurtz et al. |
| 4,022,258 A | 5/1977 | Steidley |
| 4,173,295 A | 11/1979 | Steinman |
| 4,181,140 A | 1/1980 | Ammann et al. |
| 4,275,731 A | 6/1981 | Nichols |
| 4,275,732 A | 6/1981 | Gereg |
| 4,321,922 A | 3/1982 | Deaton |
| 4,340,049 A | 7/1982 | Munsch |
| 4,346,711 A | 8/1982 | Agdanowski et al. |
| 4,347,946 A | 9/1982 | Nichols |
| 4,348,711 A | 9/1982 | Else et al. |
| 4,379,455 A | 4/1983 | Deaton |
| 4,392,860 A | 7/1983 | Huck et al. |
| 4,397,643 A | 8/1983 | Rygiel |
| 4,419,093 A | 12/1983 | Deaton |
| 4,455,140 A | 6/1984 | Joslin |
| 4,460,361 A | 7/1984 | Nichols |
| D276,464 S | 11/1984 | Weigl et al. |
| 4,492,313 A | 1/1985 | Touzani |
| 4,515,283 A | 5/1985 | Suzuki |
| 4,516,973 A | 5/1985 | Telang |
| 4,541,457 A | 9/1985 | Blenkush |
| 4,568,006 A | 2/1986 | Mueller et al. |
| 4,569,674 A | 2/1986 | Phillips et al. |
| 4,578,060 A | 3/1986 | Huck et al. |
| 4,642,128 A | 2/1987 | Solorzano |
| 4,650,477 A | 3/1987 | Johnson |
| 4,681,571 A | 7/1987 | Nehring |
| 4,706,830 A | 11/1987 | Wareing |
| 4,735,610 A | 4/1988 | Akkas et al. |
| 4,769,019 A | 9/1988 | Rosenblatt |
| 4,773,897 A | 9/1988 | Scheller et al. |
| 4,775,366 A | 10/1988 | Rosenblatt |
| 4,790,453 A | 12/1988 | Fontana et al. |
| 4,798,580 A | 1/1989 | Demeo et al. |
| 4,799,924 A | 1/1989 | Rosenblatt |
| 4,799,925 A | 1/1989 | Rosenblatt |
| 4,823,833 A | 4/1989 | Hogan et al. |
| 4,863,446 A | 9/1989 | Parker |
| 4,874,023 A | 10/1989 | Ulm |
| 4,888,728 A | 12/1989 | Shirakawa et al. |
| 4,906,261 A | 3/1990 | Mohajer |
| 4,921,679 A | 5/1990 | Martin et al. |
| 4,925,447 A | 5/1990 | Rosenblatt |
| 4,928,245 A | 5/1990 | Moy et al. |
| 4,930,997 A | 6/1990 | Bennett |
| RE33,250 E | 7/1990 | Cook |
| 4,941,689 A | 7/1990 | Sjoeberg |
| 4,948,010 A | 8/1990 | Wiggins |
| 4,950,247 A | 8/1990 | Rosenblatt |
| 4,957,491 A | 9/1990 | Parker |
| 4,957,492 A | 9/1990 | McVay |
| 4,963,134 A | 10/1990 | Bachscheider et al. |
| 4,964,189 A | 10/1990 | Rau et al. |
| 4,976,694 A | 12/1990 | Schreibman |
| 4,979,628 A | 12/1990 | Robbins, III |
| 4,980,913 A | 12/1990 | Skret |
| 4,981,473 A | 1/1991 | Rosenblatt |
| 4,986,839 A | 1/1991 | Wertz et al. |
| 5,002,534 A | 3/1991 | Rosenblatt |
| 5,010,179 A | 4/1991 | Lai |
| 5,014,389 A | 5/1991 | Ogilvie et al. |
| 5,027,963 A | 7/1991 | Robbins, III |
| 5,039,494 A | 8/1991 | Martin et al. |
| 5,071,409 A | 12/1991 | Rosenberg |
| 5,072,762 A | 12/1991 | Jimenez |
| 5,084,250 A | 1/1992 | Hall |
| 5,124,126 A | 6/1992 | Ripp |
| 5,125,891 A | 6/1992 | Hossain et al. |
| 5,149,318 A | 9/1992 | Lindsay |
| 5,156,602 A | 10/1992 | Steffler |
| 5,163,900 A | 11/1992 | Wortrich |
| 5,173,442 A | 12/1992 | Carey |
| 5,178,828 A | 1/1993 | Uesugi |
| 5,185,007 A | 2/1993 | Middaugh et al. |
| 5,192,272 A | 3/1993 | Faure |
| 5,209,565 A | 5/1993 | Goncalves |
| 5,217,038 A | 6/1993 | Pinder |
| 5,217,688 A | 6/1993 | Von Lersner |
| 5,234,419 A | 8/1993 | Bryant et al. |
| 5,242,434 A | 9/1993 | Terry |
| 5,242,474 A | 9/1993 | Herbst et al. |
| 5,252,290 A | 10/1993 | Uesugi |
| 5,254,080 A | 10/1993 | Lindsay |
| 5,267,956 A | 12/1993 | Beuchat |
| 5,268,666 A | 12/1993 | Michel et al. |
| 5,269,030 A | 12/1993 | Pahno et al. |
| 5,279,602 A | 1/1994 | Middaugh et al. |
| 5,295,518 A | 3/1994 | Baker et al. |
| 5,309,924 A | 5/1994 | Peabody |
| 5,318,516 A | 6/1994 | Cosmescu |
| 5,330,464 A | 7/1994 | Mathias et al. |
| 5,333,761 A | 8/1994 | Davis et al. |
| 5,336,169 A | 8/1994 | Divilio et al. |
| 5,364,342 A | 11/1994 | Beuchat et al. |
| 5,370,270 A | 12/1994 | Adams et al. |
| 5,380,289 A | 1/1995 | Hemstreet et al. |
| 5,399,156 A | 3/1995 | Lindsay |
| 5,417,655 A | 5/1995 | Divilio et al. |
| 5,423,779 A | 6/1995 | Yeh |
| 5,438,721 A | 8/1995 | Pahno et al. |
| 5,470,324 A | 11/1995 | Cook et al. |
| 5,494,074 A | 2/1996 | Ramacier, Jr. et al. |
| 5,514,119 A | 5/1996 | Curtis |
| 5,519,858 A | 5/1996 | Walton et al. |
| 5,520,668 A | 5/1996 | Greff et al. |
| 5,522,808 A | 6/1996 | Skalla |

(56) References Cited

U.S. PATENT DOCUMENTS

| | | |
|---|---|---|
| 5,526,956 A | 6/1996 | Osgar |
| 5,549,585 A | 8/1996 | Maher et al. |
| 5,551,001 A | 8/1996 | Cohen et al. |
| 5,588,167 A | 12/1996 | Pahno et al. |
| 5,620,428 A | 4/1997 | Hand |
| 5,607,411 A | 5/1997 | Heironimus et al. |
| 5,634,896 A | 6/1997 | Bryant et al. |
| 5,637,103 A | 6/1997 | Kerwin et al. |
| 5,645,540 A | 7/1997 | Henniges et al. |
| 5,653,270 A | 8/1997 | Burrows |
| 5,669,892 A | 9/1997 | Keogh et al. |
| 5,683,371 A | 11/1997 | Hand |
| 5,685,835 A | 11/1997 | Brugger |
| 5,688,255 A | 11/1997 | Hand |
| 5,720,078 A | 2/1998 | Heintz |
| 5,741,237 A | 4/1998 | Walker |
| 5,741,238 A | 4/1998 | Bradbury et al. |
| 5,755,705 A | 5/1998 | Van Driel |
| 5,776,118 A | 7/1998 | Seifert et al. |
| 5,776,260 A | 7/1998 | Dunn et al. |
| 5,785,044 A | 7/1998 | Meador et al. |
| 5,792,126 A | 8/1998 | Tribastone et al. |
| 5,797,506 A | 8/1998 | Lehmkuhl et al. |
| 5,807,230 A | 9/1998 | Argenta et al. |
| 5,807,359 A | 9/1998 | Bemis et al. |
| 5,808,885 A | 9/1998 | Dew et al. |
| 5,830,198 A | 11/1998 | Henniges et al. |
| 5,835,723 A | 11/1998 | Andrews et al. |
| 5,836,909 A | 11/1998 | Cosmescu |
| 5,855,289 A | 1/1999 | Moore |
| 5,859,847 A | 1/1999 | Dew et al. |
| 5,867,555 A | 2/1999 | Popescu et al. |
| 5,871,476 A | 2/1999 | Hand |
| 5,885,240 A | 3/1999 | Bradbury et al. |
| 5,901,291 A | 5/1999 | Feeney et al. |
| 5,901,717 A | 5/1999 | Dunn et al. |
| 5,906,025 A | 5/1999 | Johnson |
| 5,910,291 A | 6/1999 | Skalla et al. |
| 5,914,047 A | 6/1999 | Griffiths |
| 5,919,360 A | 7/1999 | Contaxis, III et al. |
| 5,931,822 A | 8/1999 | Bemis et al. |
| 5,944,703 A | 8/1999 | Dixon et al. |
| 5,945,004 A | 8/1999 | Ohira et al. |
| 5,947,171 A | 9/1999 | Woodruff |
| 5,968,032 A | 10/1999 | Sleister |
| 5,975,096 A | 11/1999 | Dunn et al. |
| 5,985,009 A | 11/1999 | Marsala |
| 5,997,733 A | 12/1999 | Wilbur et al. |
| 6,006,272 A | 12/1999 | Aravamudan et al. |
| 6,017,493 A | 1/2000 | Cambron et al. |
| 6,024,124 A | 2/2000 | Braun et al. |
| 6,027,490 A | 2/2000 | Radford et al. |
| 6,039,724 A | 3/2000 | Seifert et al. |
| 6,045,596 A | 4/2000 | Holland, Jr. et al. |
| 6,056,731 A | 5/2000 | Koetke et al. |
| 6,058,106 A | 5/2000 | Cudak et al. |
| 6,078,952 A | 6/2000 | Fielding et al. |
| 6,082,401 A | 7/2000 | Braun et al. |
| 6,093,230 A | 7/2000 | Johnson, III et al. |
| 6,105,093 A | 8/2000 | Rosner et al. |
| 6,105,638 A | 8/2000 | Edwards et al. |
| 6,115,881 A | 9/2000 | Hult et al. |
| 6,136,098 A | 10/2000 | Tribastone |
| 6,152,902 A | 11/2000 | Christian et al. |
| 6,160,808 A | 12/2000 | Maurya |
| 6,161,578 A | 12/2000 | Braun et al. |
| 6,180,000 B1 | 1/2001 | Wilbur et al. |
| 6,203,590 B1 | 3/2001 | Byrd et al. |
| 6,222,283 B1 | 4/2001 | Regla |
| 6,231,089 B1 | 5/2001 | Decler et al. |
| 6,233,248 B1 | 5/2001 | Sautter et al. |
| 6,244,311 B1 | 6/2001 | Hand et al. |
| 6,258,232 B1 | 7/2001 | Hasegawa et al. |
| 6,261,276 B1 | 7/2001 | Reitsma |
| 6,263,887 B1 | 7/2001 | Dunn |
| 6,270,488 B1 | 8/2001 | Johnson et al. |
| 6,280,867 B1 | 8/2001 | Elias |
| 6,331,246 B1 | 12/2001 | Beckham et al. |
| 6,358,232 B1 | 3/2002 | Hand et al. |
| 6,366,583 B2 | 4/2002 | Rowett et al. |
| 6,368,310 B1 | 4/2002 | Bemis et al. |
| 6,415,313 B1 | 7/2002 | Yamada et al. |
| 6,453,687 B2 | 9/2002 | Sharood et al. |
| 6,488,675 B1 | 12/2002 | Radford et al. |
| 6,494,391 B2 | 12/2002 | Mosenson et al. |
| 6,494,869 B1 | 12/2002 | Hand et al. |
| 6,499,495 B2 | 12/2002 | Jeng |
| 6,501,180 B1 | 12/2002 | Kitch |
| 6,507,953 B1 | 1/2003 | Horlander et al. |
| 6,522,654 B1 | 2/2003 | Small |
| 6,524,307 B1 | 2/2003 | Palmerton et al. |
| 6,588,436 B2 | 7/2003 | Dunn et al. |
| 6,615,243 B1 | 9/2003 | Megeid et al. |
| 6,618,764 B1 | 9/2003 | Shteyn |
| 6,626,877 B2 | 9/2003 | Anderson et al. |
| 6,631,476 B1 | 10/2003 | Vandesteeg et al. |
| 6,652,495 B1 | 11/2003 | Walker |
| 6,672,477 B2 | 1/2004 | Miller et al. |
| 6,673,055 B2 | 1/2004 | Bemis et al. |
| 6,676,644 B2 | 1/2004 | Ikeda |
| 6,688,436 B1 | 2/2004 | Wang |
| 6,705,591 B2 | 3/2004 | Decler |
| 6,706,198 B2 | 3/2004 | Gershenson |
| 6,721,900 B1 | 4/2004 | Lenner et al. |
| 6,731,201 B1 | 5/2004 | Bailey et al. |
| 6,735,619 B1 | 5/2004 | Sawada |
| 6,755,807 B2 | 6/2004 | Risk, Jr. et al. |
| 6,759,946 B2 | 7/2004 | Sahinoglu et al. |
| 6,770,061 B2 | 8/2004 | Wildman |
| 6,776,175 B2 | 8/2004 | Dunn et al. |
| 6,780,309 B2 | 8/2004 | Haldopoulos et al. |
| 6,793,222 B2 | 9/2004 | Katsaounis et al. |
| 6,800,074 B2 | 10/2004 | Henley et al. |
| 6,824,533 B2 | 11/2004 | Risk, Jr. et al. |
| 6,842,430 B1 | 1/2005 | Melnik |
| 6,854,053 B2 | 2/2005 | Burkhardt et al. |
| 6,856,999 B2 | 2/2005 | Flanagin et al. |
| 6,891,850 B1 | 5/2005 | Vandesteeg et al. |
| 6,893,425 B2 | 5/2005 | Dunn et al. |
| 6,902,673 B2 | 6/2005 | Smit et al. |
| 6,909,891 B2 | 6/2005 | Yamashita et al. |
| 6,915,444 B2 | 7/2005 | Vasko et al. |
| 6,934,740 B1 | 8/2005 | Lawande et al. |
| 6,976,977 B2 | 12/2005 | Yam |
| 6,982,960 B2 | 1/2006 | Lee et al. |
| 6,987,462 B2 | 1/2006 | Bae et al. |
| 7,035,270 B2 | 4/2006 | Moore, Jr. et al. |
| 7,058,722 B2 | 6/2006 | Ikami et al. |
| 7,062,531 B2 | 6/2006 | Kim |
| 7,069,091 B2 | 6/2006 | Williamson |
| 7,090,663 B2 | 8/2006 | Dunn et al. |
| 7,107,358 B2 | 9/2006 | Vasko et al. |
| 7,111,100 B2 | 9/2006 | Ellerbrock |
| 7,114,518 B2 | 10/2006 | Kirby |
| 7,115,115 B2 | 10/2006 | Bemis et al. |
| 7,115,228 B2 | 10/2006 | Lundtveit et al. |
| 7,148,142 B1 | 12/2006 | Dakshina-Murthy et al. |
| 7,149,792 B1 | 12/2006 | Hansen et al. |
| 7,163,618 B2 | 1/2007 | Beckham et al. |
| 7,200,683 B1 | 4/2007 | Wang et al. |
| 7,257,104 B2 | 8/2007 | Shitama |
| 7,258,711 B2 | 8/2007 | Dunn et al. |
| 7,287,062 B2 | 10/2007 | Im et al. |
| 7,294,839 B2 | 11/2007 | Rich et al. |
| 7,308,644 B2 | 12/2007 | Humpleman et al. |
| 7,328,816 B2 | 2/2008 | Shannon et al. |
| 7,353,259 B1 | 4/2008 | Bakke et al. |
| 7,389,332 B1 | 6/2008 | Muchow et al. |
| 7,389,358 B1 | 6/2008 | Matthews et al. |
| 7,403,994 B1 | 7/2008 | Vogl et al. |
| 7,412,538 B1 | 8/2008 | Eytchison et al. |
| 7,421,478 B1 | 9/2008 | Muchow |
| 7,430,591 B2 | 9/2008 | Chamberlain |
| 7,437,494 B2 | 10/2008 | Ellerbrock |

(56) References Cited

U.S. PATENT DOCUMENTS

| | | |
|---|---|---|
| 7,454,517 B2 | 11/2008 | Ha et al. |
| 7,461,164 B2 | 12/2008 | Edwards et al. |
| 7,468,330 B2 | 12/2008 | Allen et al. |
| 7,469,727 B2 | 12/2008 | Marshall |
| 7,481,243 B2 | 1/2009 | Michaels et al. |
| 7,497,340 B2 | 3/2009 | Hershberger et al. |
| 7,673,030 B2 | 3/2010 | Hite et al. |
| 7,673,153 B1 | 3/2010 | Oishi et al. |
| 2001/0025322 A1 | 9/2001 | Song et al. |
| 2002/0011923 A1 | 1/2002 | Cunningham et al. |
| 2002/0021465 A1 | 2/2002 | Moore, Jr. et al. |
| 2002/0026528 A1 | 2/2002 | Lo |
| 2002/0035624 A1 | 3/2002 | Kim |
| 2002/0038358 A1 | 3/2002 | Sweatt, III et al. |
| 2002/0059617 A1 | 5/2002 | Terakado et al. |
| 2002/0082569 A1 | 6/2002 | Wildman |
| 2002/0103898 A1 | 8/2002 | Moyer et al. |
| 2002/0118696 A1 | 8/2002 | Suda |
| 2002/0120763 A1 | 8/2002 | Miloushev et al. |
| 2002/0127780 A1 | 9/2002 | Ma et al. |
| 2002/0165989 A1 | 11/2002 | Etoh |
| 2002/0183702 A1 | 12/2002 | Henley et al. |
| 2002/0193144 A1 | 12/2002 | Belski et al. |
| 2003/0009537 A1 | 1/2003 | Wang |
| 2003/0014530 A1 | 1/2003 | Bodin et al. |
| 2003/0014630 A1 | 1/2003 | Spencer et al. |
| 2003/0037166 A1 | 2/2003 | Ueno et al. |
| 2003/0038730 A1 | 2/2003 | Imafuku et al. |
| 2003/0051053 A1 | 3/2003 | Vasko et al. |
| 2003/0051203 A1 | 3/2003 | Vasko et al. |
| 2003/0053477 A1 | 3/2003 | Kim et al. |
| 2003/0054809 A1 | 3/2003 | Bridges et al. |
| 2003/0065824 A1 | 4/2003 | Kudo |
| 2003/0067910 A1 | 4/2003 | Razazian et al. |
| 2003/0079000 A1 | 4/2003 | Chamberlain |
| 2003/0079001 A1 | 4/2003 | Chamberlain |
| 2003/0083758 A1 | 5/2003 | Williamson |
| 2003/0085795 A1 | 5/2003 | An |
| 2003/0088703 A1 | 5/2003 | Kim |
| 2003/0158956 A1 | 8/2003 | Tanaka et al. |
| 2003/0165142 A1 | 9/2003 | Mills et al. |
| 2004/0023162 A1 | 2/2004 | Hasegawa et al. |
| 2004/0042487 A1 | 3/2004 | Ossman |
| 2004/0047298 A1 | 3/2004 | Yook et al. |
| 2004/0055105 A1 | 3/2004 | Park et al. |
| 2004/0064578 A1 | 4/2004 | Boucher et al. |
| 2004/0088731 A1 | 5/2004 | Putterman et al. |
| 2004/0102743 A1 | 5/2004 | Walker |
| 2004/0111490 A1 | 6/2004 | Im et al. |
| 2004/0116902 A1 | 6/2004 | Grossman et al. |
| 2004/0129338 A1 | 7/2004 | Rohret et al. |
| 2004/0158333 A1 | 8/2004 | Ha et al. |
| 2004/0158388 A1 | 8/2004 | Fujiwara et al. |
| 2004/0164076 A1 | 8/2004 | Baker et al. |
| 2004/0184456 A1 | 9/2004 | Binding et al. |
| 2004/0204603 A1 | 10/2004 | Leconte et al. |
| 2004/0204679 A1 | 10/2004 | Visconti et al. |
| 2004/0204693 A1 | 10/2004 | Anderson et al. |
| 2004/0205309 A1 | 10/2004 | Watanabe |
| 2004/0224261 A1 | 11/2004 | Resnick et al. |
| 2005/0069696 A1 | 3/2005 | King et al. |
| 2005/0108568 A1 | 5/2005 | Bussiere et al. |
| 2005/0139532 A1 | 6/2005 | Hershberger et al. |
| 2005/0170269 A1 | 8/2005 | Nakagawa et al. |
| 2005/0171495 A1 | 8/2005 | Austin et al. |
| 2005/0187526 A1 | 8/2005 | Horne |
| 2005/0187528 A1 | 8/2005 | Berg |
| 2005/0187529 A1 | 8/2005 | Reasoner et al. |
| 2005/0189283 A1 | 9/2005 | Smit et al. |
| 2005/0189288 A1 | 9/2005 | Hershberger et al. |
| 2005/0190727 A1 | 9/2005 | Vanlieshout et al. |
| 2005/0202350 A1 | 9/2005 | Colburn et al. |
| 2005/0215961 A1 | 9/2005 | Romano et al. |
| 2005/0250052 A1 | 11/2005 | Nguyen |
| 2005/0267445 A1 | 12/2005 | Mendels |
| 2006/0030681 A1 | 2/2006 | Sawyer et al. |
| 2006/0036219 A1 | 2/2006 | Alvin |
| 2006/0047677 A1 | 3/2006 | Lin et al. |
| 2006/0129092 A1 | 6/2006 | Hanlon et al. |
| 2006/0156836 A1 | 7/2006 | Ny et al. |
| 2006/0156918 A1 | 7/2006 | Dahl |
| 2006/0248518 A1 | 11/2006 | Kundert |
| 2006/0271709 A1 | 11/2006 | Vasko et al. |
| 2007/0019615 A1 | 1/2007 | Baek et al. |
| 2007/0025368 A1 | 2/2007 | Ha et al. |
| 2007/0032058 A1 | 2/2007 | Sung |
| 2007/0038191 A1 | 2/2007 | Burbank et al. |
| 2007/0044439 A1 | 3/2007 | Dunn et al. |
| 2007/0135778 A1 | 6/2007 | Murray et al. |
| 2007/0135779 A1 | 6/2007 | Lalomia et al. |
| 2008/0053539 A1 | 3/2008 | Hershberger et al. |
| 2008/0097631 A1 | 4/2008 | Baek et al. |
| 2008/0222325 A1 | 9/2008 | Ishino et al. |
| 2008/0255692 A1 | 10/2008 | Hofrichter et al. |
| 2008/0259786 A1 | 10/2008 | Gonda |
| 2009/0005747 A1 | 1/2009 | Michaels et al. |
| 2009/0012485 A1 | 1/2009 | Michaels et al. |
| 2009/0159535 A1 | 6/2009 | Hershberger et al. |
| 2009/0182263 A1 | 7/2009 | Burbank et al. |
| 2011/0178482 A1 | 7/2011 | Michaels et al. |
| 2011/0313375 A1 | 12/2011 | Michaels |
| 2013/0144232 A1 | 6/2013 | Michaels et al. |
| 2013/0247326 A1 | 9/2013 | Michaels et al. |
| 2013/0341330 A1 | 12/2013 | Michaels et al. |
| 2013/0345651 A1 | 12/2013 | Michaels et al. |

FOREIGN PATENT DOCUMENTS

| | | |
|---|---|---|
| CN | 1398468 A | 2/2003 |
| CN | 1398469 | 2/2003 |
| EP | 1031357 A2 | 8/2000 |
| EP | 1 115 263 A1 | 7/2001 |
| EP | 1 202 493 A2 | 5/2002 |
| EP | 1 387 216 A2 | 2/2004 |
| EP | 1387215 A1 | 2/2004 |
| FR | 2808449 A3 | 11/2001 |
| GB | 2 233 494 A | 1/1991 |
| JP | 60-112336 | 6/1985 |
| JP | 61-216543 | 9/1986 |
| JP | 8-500763 | 1/1996 |
| JP | 08-112344 | 5/1996 |
| JP | 9295651 A | 11/1997 |
| JP | 2002-325079 | 11/2002 |
| JP | 2003-519460 | 6/2003 |
| KR | 10-2001-0093265 | 10/2001 |
| KR | 10-2002-0064847 | 8/2002 |
| KR | 20020084847 A | 11/2002 |
| KR | 10-2003-0040766 | 5/2003 |
| WO | WO 80/01558 A1 | 8/1980 |
| WO | 9112033 A1 | 8/1991 |
| WO | WO 95/01192 | 1/1995 |
| WO | 9517912 A1 | 7/1995 |
| WO | WO 98/55164 | 12/1998 |
| WO | WO 01/03178 A1 | 1/2001 |
| WO | 0124846 A1 | 4/2001 |
| WO | WO 01/50825 A1 | 7/2001 |
| WO | WO 01/80030 A1 | 10/2001 |
| WO | WO 02/09350 A3 | 3/2002 |
| WO | 02074632 A1 | 9/2002 |
| WO | WO 02/097555 A2 | 12/2002 |
| WO | WO 02/097555 A3 | 12/2002 |
| WO | WO 03/030252 A2 | 4/2003 |
| WO | WO 2005/031855 A1 | 4/2005 |
| WO | 2006041406 A1 | 4/2006 |
| WO | WO 2008/094703 A2 | 8/2008 |

OTHER PUBLICATIONS

Ganz et al., "Q-Soft: software framework for QoS support in home networks," Computer Nov. 1998, pp. 1-66.

Hwang et al., "ATM-based plug-and-play technique for in-home networking," Electronics Letters, vol. 34, No. 22, pp. 2088-2090, 1998.

(56) References Cited

OTHER PUBLICATIONS

International Search Report & Written Opinion issued in PCT/US2008/03817, dated Jun. 20, 2008 11 pages.
International Search Report issued in PCT/US2008/03818, dated Jul. 30, 2008, 13 pages.
Invitation to Pay Additional Fees & Partial Search Report issued in PCT/US2007/008371, dated Oct. 29, 2007, 4 pages.
Kent et al., "Security Architecture for the Internet Protocol," Network Working Group, Nov. 1998, pp. 1-66.
Kim et al., "Home Networking Digital TV Based on LnCP," IEEE Transaction on Consumer Electronics, vol. 48, No. 4, Nov. 2002, pp. 990-996.
Lee et al., "A New Control Protocol for Home Appliance LnCP" International Symposium on Industrial Electronics, 2001, Proceedings, ISIE 2001, Jun. 12-16, 2001 pp. 286-291.
Lee et al., "A New Home Network Protocol Controlling and Monitoring Home Appliance-HNCP," IEEE, 2002, pp. 312-313.
Lee et al., "Home Network Control Protocol for Networked Home Appliance and Its Application," IEEE, pp. 1-7, 2002.
Letter from Foreign Associate dated Jun. 26, 2008, with Official Translation of Communication issued in DE 10 2006 030 267.2, dated May 26, 2008, 3 pages.
Manner et al., "Evaluation of Mobility and quality of service interaction," The International Journal of Computer and Telecommunications Networking, vol. 38, No. 2, pp. 137-163, 2002.
Neptune 2 Ultra, Waste Management System, 2 pages; as viewed at http://www.stryker.com/stellent/groups/instruments/documents/web_prod/059445.pdf, Feb. 21, 2008, pp. 1-2.
Notice of Rejection issued in Japanese Application No. 2010-500951, dated Jan. 8, 2013, 4 pages.
Official Translation of Communication issued in DE 10 2006 030 267.2, dated Sep. 13, 2007, 4 pages.
Wang et al., "Towards Dependable Home Networking: An Experience Report," IEEE, 2000, pp. 43-48.
Written Opinion of the ISA issued in PCT/US2007/008371, 4 Pages.
"Check valve" Entry from McGraw-Hill Dictionary of Engineering,© 1997, p. 94, published by the McGraw-Hill Companies Inc.
Figures, Neptune 2 Ultra, Waste Management System, online [Retrieved on Feb. 21, 2008] Retrieved from the internet: pp. 1-2.
Ganz, A., et al., "Q-Soft software Framework for QoS Support in Home Networks," Computer Networks 2003, vol. 42, pp. 7-22.
International Search Report and Written Opinion for Application No. PCT/US2008/03818, dated Jul. 30, 2008, 12 pages.
International Search Report and Written Opinion for Application No. PCT/US2010/042145, dated Sep. 13, 2010, 8 pages.
International Search Report for Application No. PCT/US08/03817, dated Jun. 20, 2008, 1 page.
"New Surgical System from Stryker Installed in BCHS Operating Rooms," Battle Creek Health System. [Retrieved on Feb. 21, 2008] Retrieved from the internet: URL: http://www.bchealth.com/news/stryker.shtml, 2 pages.
Non-Final Office Action dated Aug. 31, 2015 for U.S. Appl. No. 13/908,752, filed Jun. 3, 2013.
"Supplementary European Search Report and Search Opinion for European Application No. 08742213.5, dated Aug. 8, 2012, 5 pages."

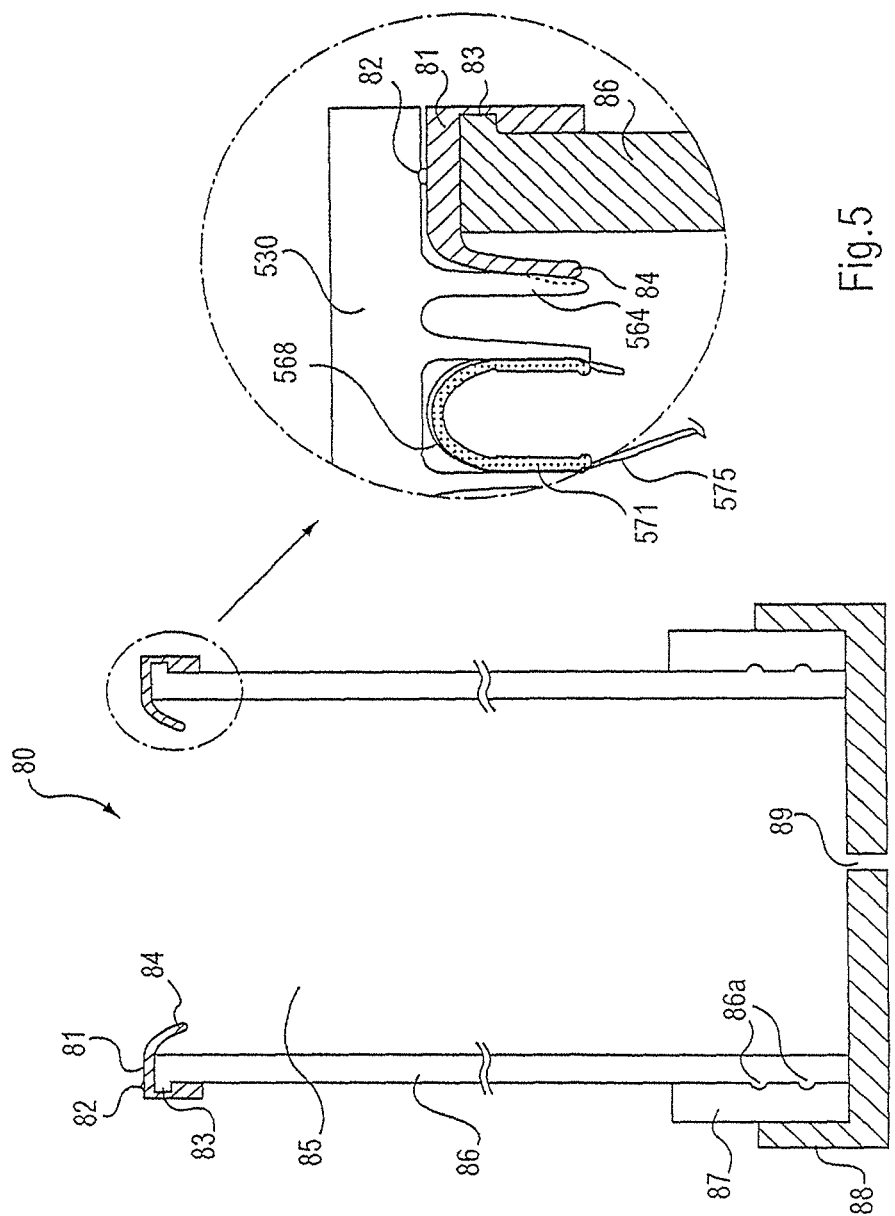

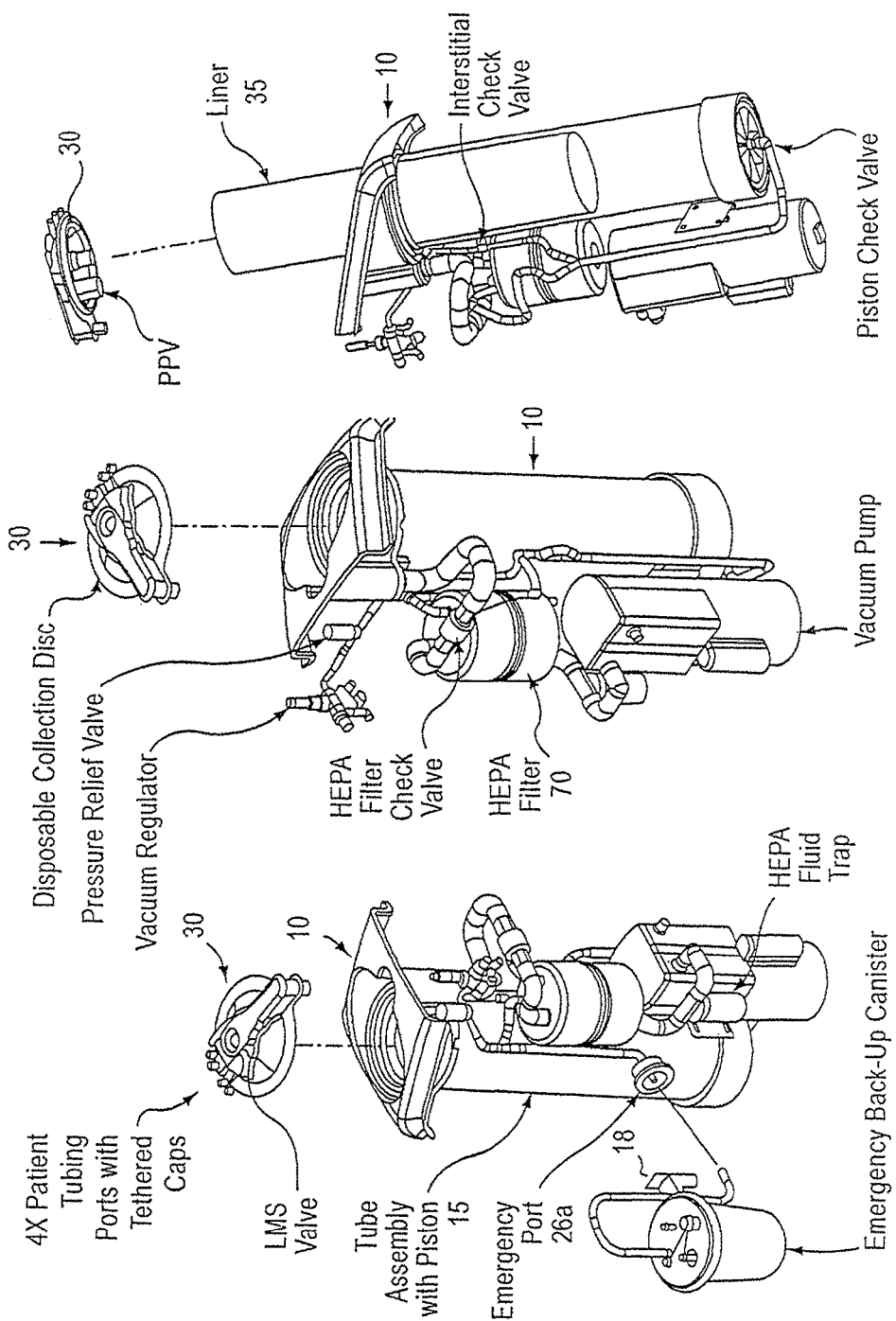

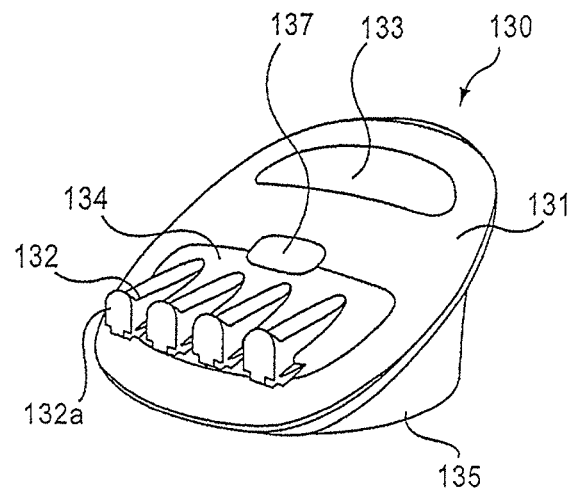
Fig.15
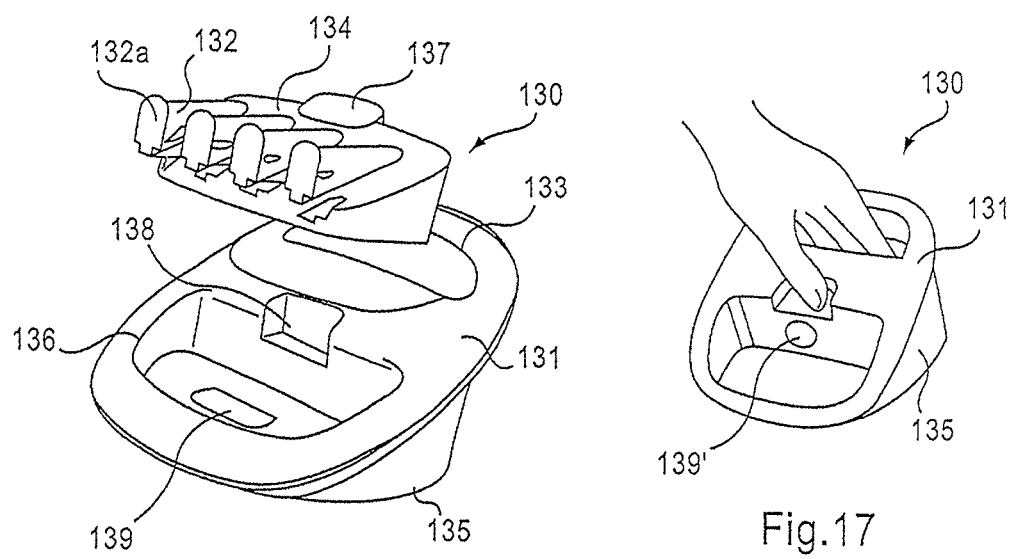
Fig.16
Fig.17

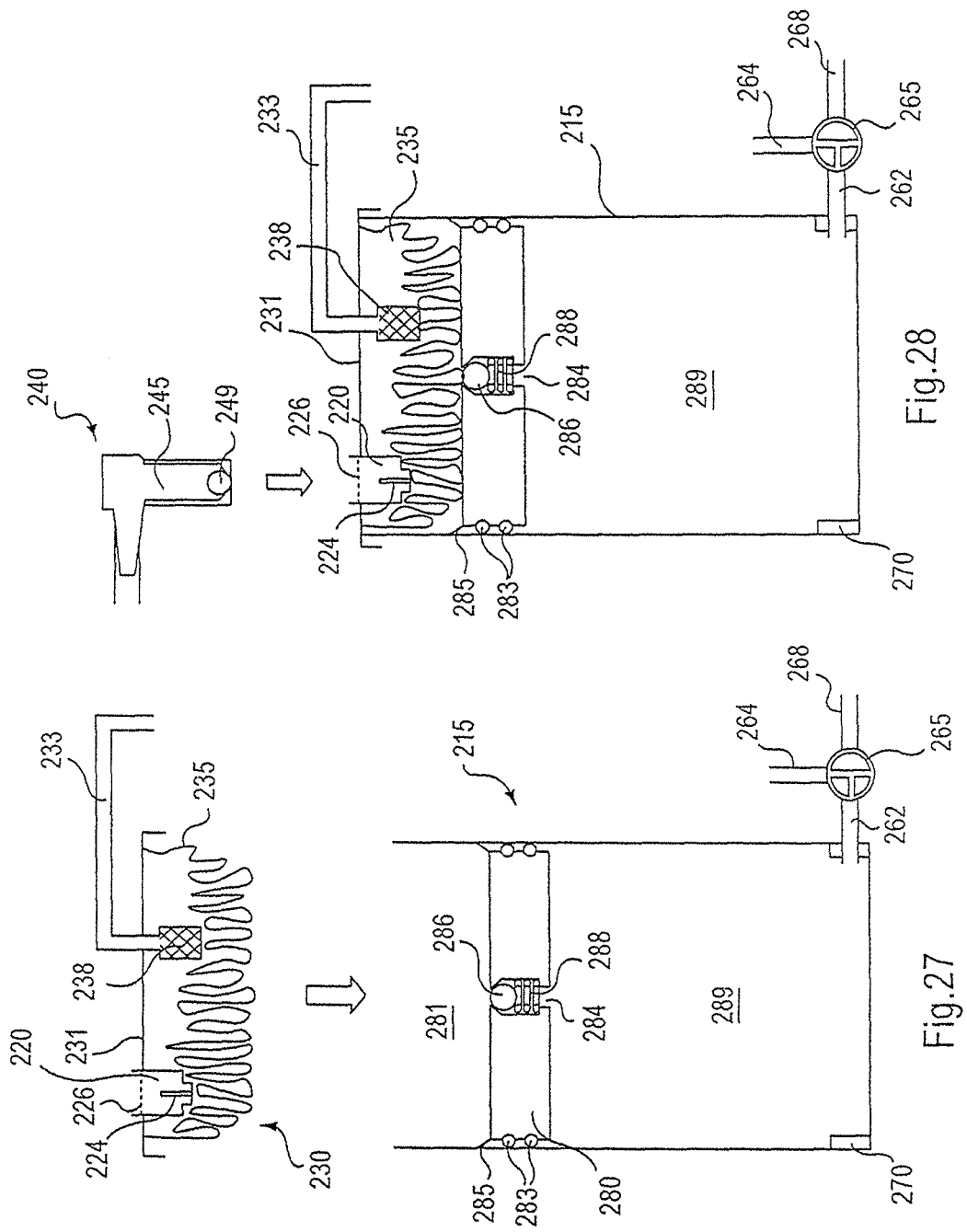

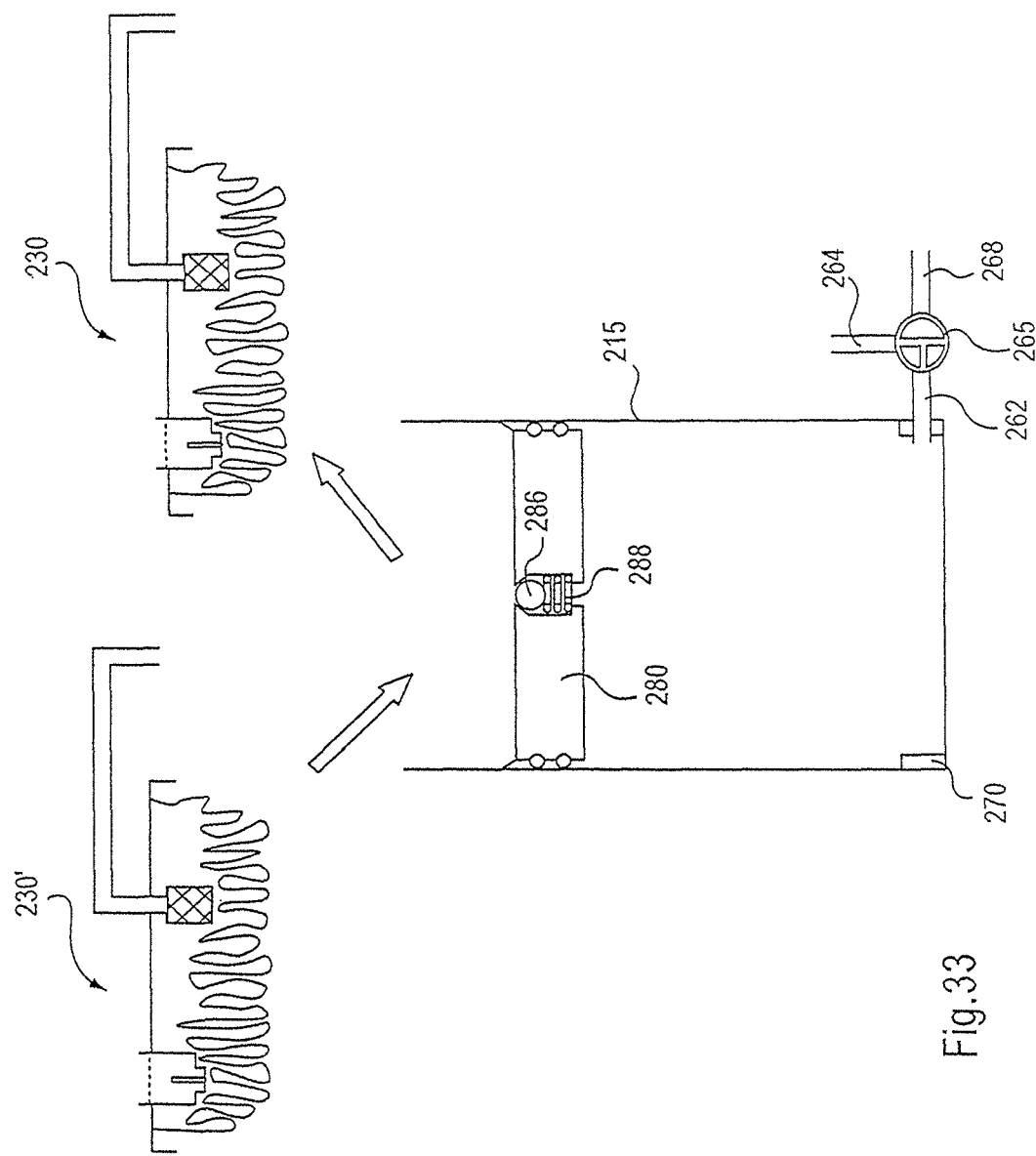

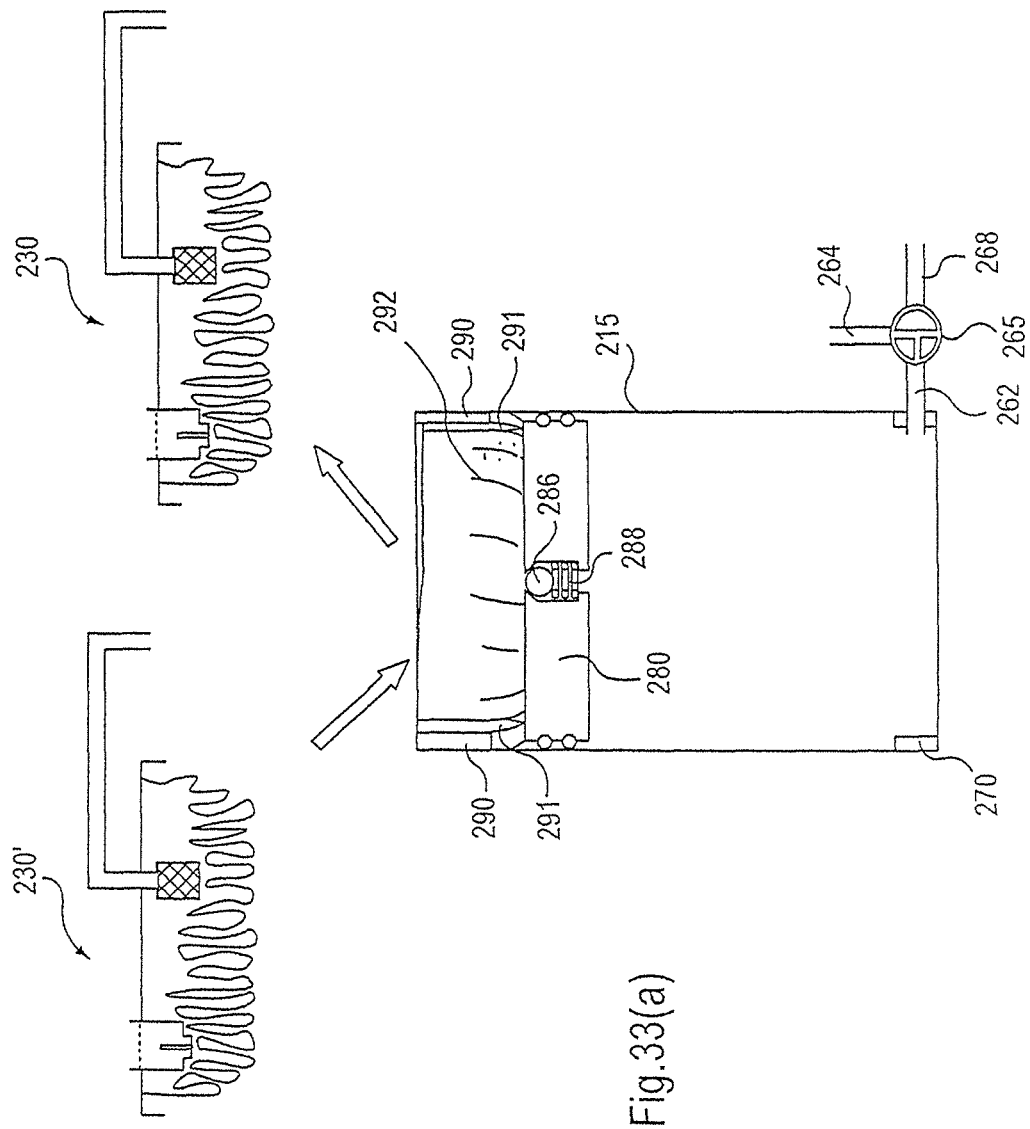

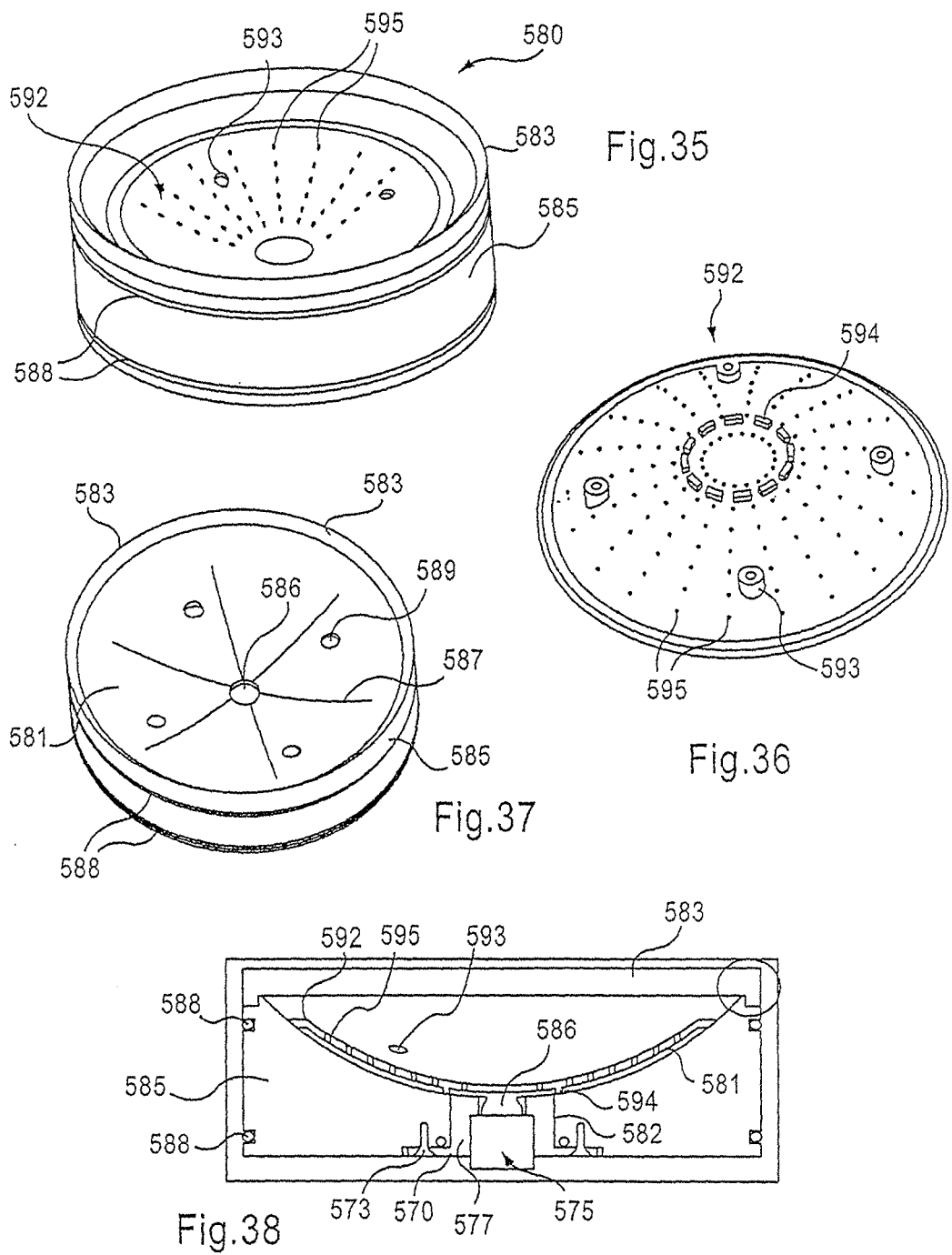

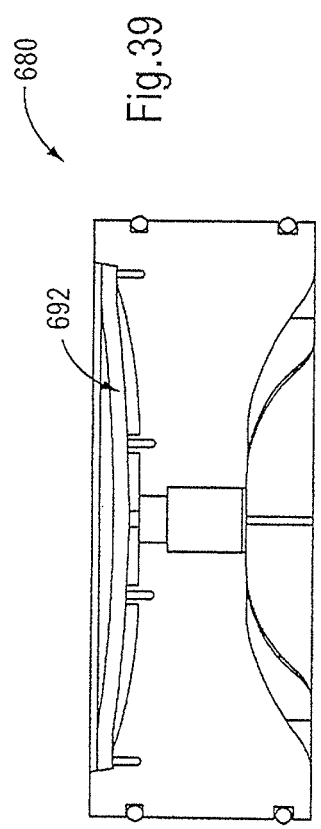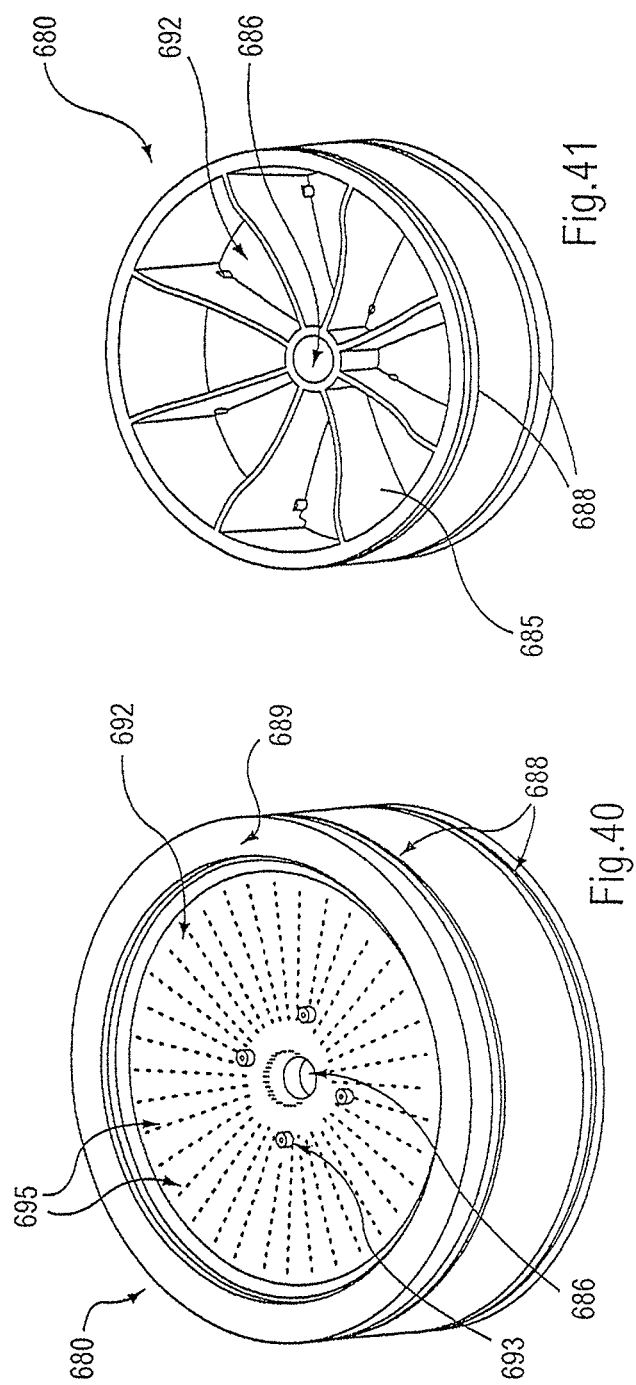

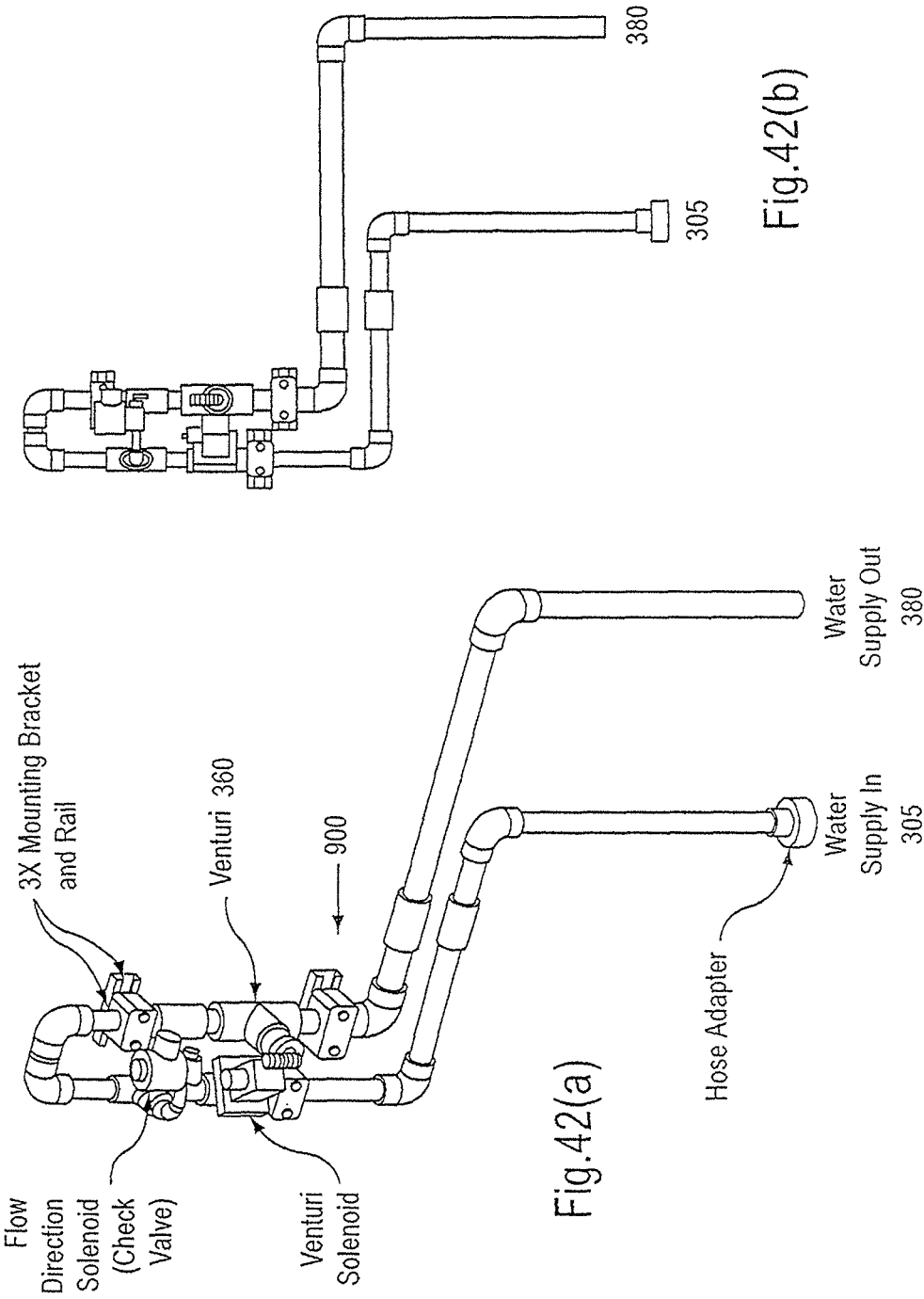

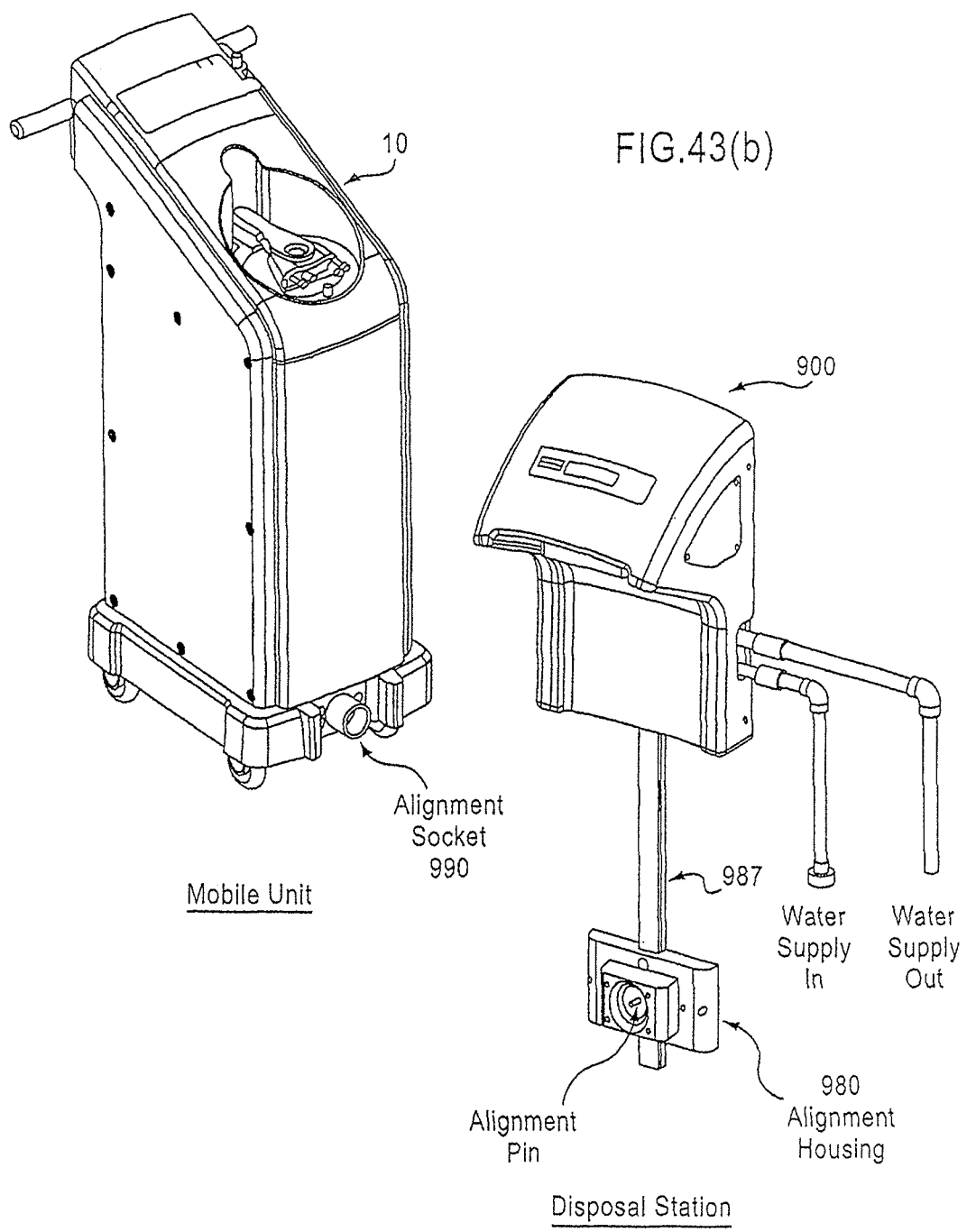

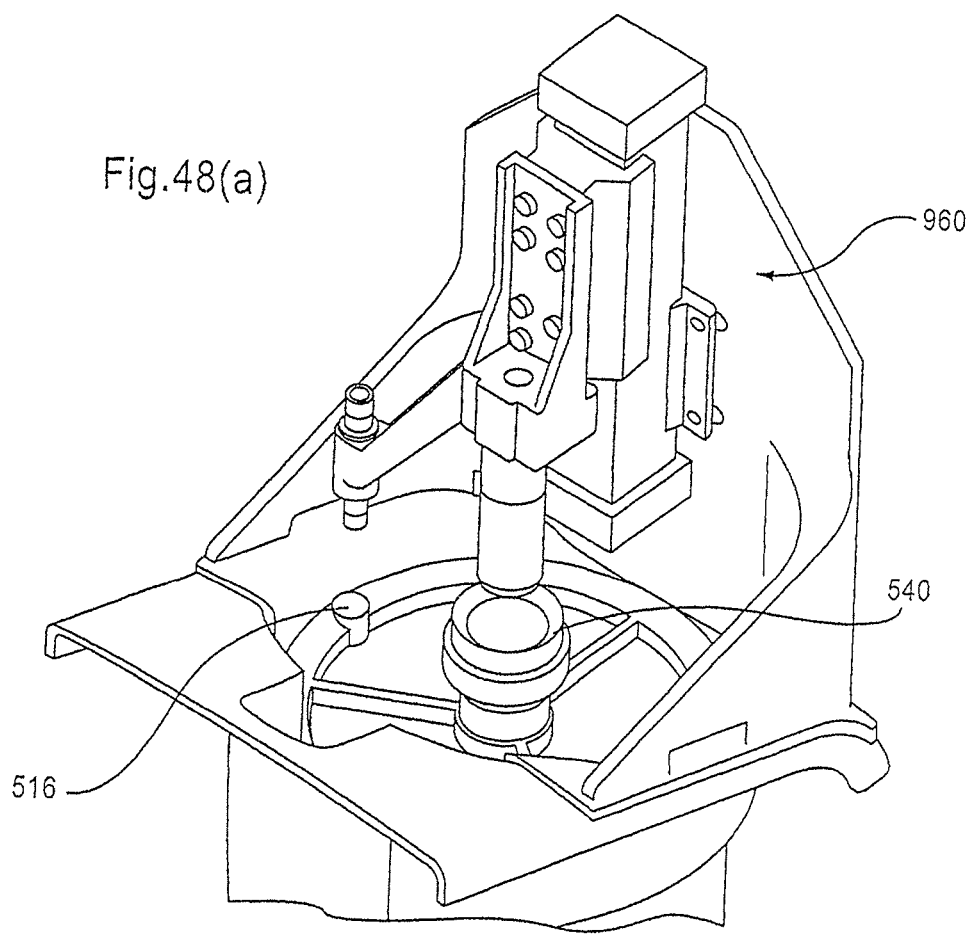

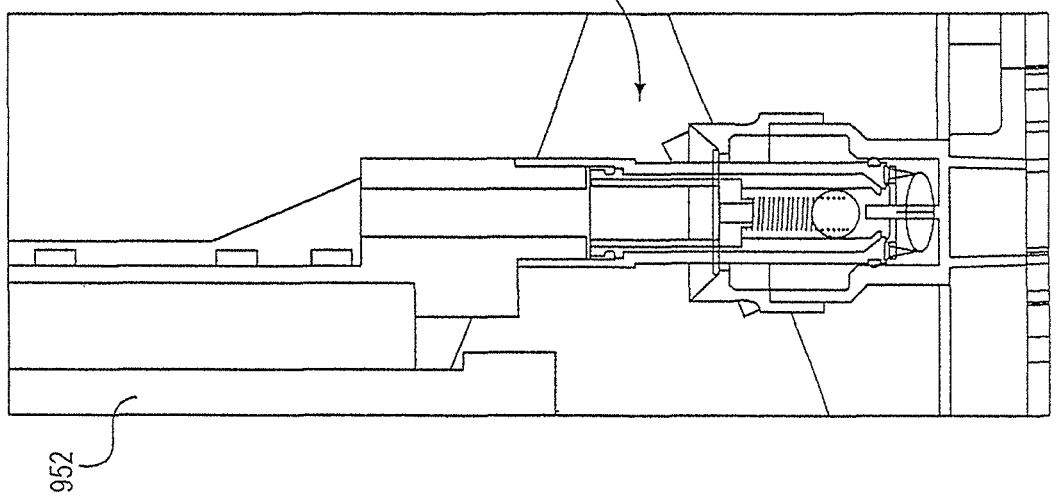
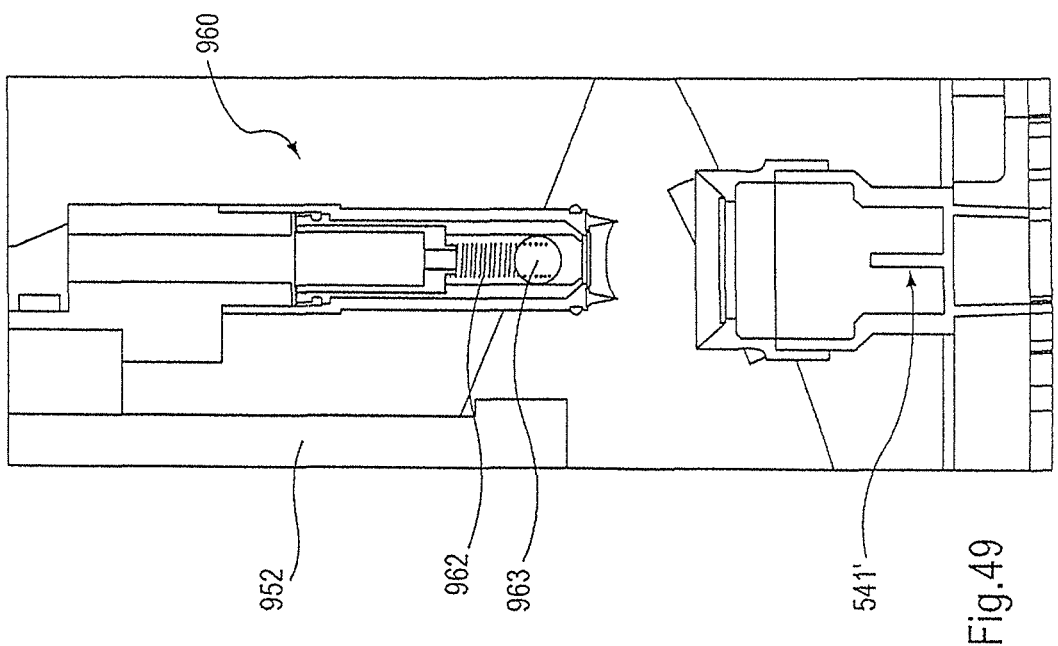

FLUID COLLECTION AND DISPOSAL SYSTEM HAVING INTERCHANGEABLE COLLECTION AND OTHER FEATURES AND METHODS RELATING THEREOF

CROSS REFERENCE TO RELATED APPLICATIONS

This application is a divisional of U.S. patent application Ser. No. 12/076,842, filed Mar. 24, 2008, titled FLUID COLLECTION AND DISPOSAL SYSTEM HAVING INTERCHANGEABLE COLLECTION AND OTHER FEATURES AND METHODS RELATING THERETO, now U.S. Pat. No. 8,500,706, which claims the benefit of priority from prior U.S. provisional application No. 60/919,607, filed on Mar. 23, 2007, titled LIQUID COLLECTION AND DISPOSAL SYSTEM AND RELATED METHODS and U.S. provisional application No. 60/963,325, filed on Aug. 3, 2007, titled LIQUID COLLECTION AND DISPOSAL SYSTEM AND RELATED METHODS, the entire contents of each of which are incorporated herein by reference.

U.S. patent application Ser. No. 12/076,842 is also related to applicants' co-pending U.S. patent application Ser. No. 12/076,841, filed on Mar. 24, 2008, now abandoned, titled FLUID COLLECTION AND DISPOSAL SYSTEM HAVING INTERCHANGEABLE COLLECTION AND OTHER FEATURES AND METHODS RELATING THERETO, the entire contents of which are incorporated therein by reference, and the entire contents of which are incorporated herein by reference.

BACKGROUND OF THE INVENTION

1. Technical Field of the Invention

Aspects of the present invention relate generally to fluid collection and disposal systems and related methods. More specifically, particular embodiments relate to liquid collection and disposal systems that utilize flexible liners and related methods of use thereof.

2. Brief Description of Related Art

Hospital operating rooms, emergency rooms, and other healthcare facilities generate a large volume of liquid waste, which may include irrigation liquids and secretions removed from a patient's body (e.g., blood and other bodily liquids). To collect and dispose of such liquid waste, suction canisters are typically used. A typical suction canister is a temporary storage container that uses suction to create a negative pressure inside the canister to drain liquids or secretions from the patients' body. After each medical procedure (e.g., surgery), the canister containing the liquid waste is transported to a utility area to be disposed of as red-bag waste or to be emptied, cleaned, and disinfected for reuse. A new or cleaned canister is then brought into the operating room for a next medical procedure. This process can be labor intensive and time consuming. Furthermore, since this process is performed following every medical procedure, the frequency of the process may increase the clinicians' risk of exposure to potentially hazardous waste.

Accordingly, there is a need for an improved waste collection and disposal system that may overcome one or more of the problems discussed above.

SUMMARY OF THE INVENTION

Among others, various aspects of the invention may include providing a fluid collection system that utilizes disposable flexible liners to reduce the volume of medical wastes. Another aspect may include providing a lid for a fluid collection system that automatically connects to a suction source. Also, certain aspects of the invention may provide a waste disposal system, for use with the fluid collection system that may improve labor efficiency, safety, and convenience of the medical personnel participating in a medical procedure. In particular, the fluid collection systems and waste disposal systems in accordance with aspects of the present invention may provide a clean and convenient interface between the source of waste and the waste disposal station, thereby reducing the risk of exposure to potentially hazardous waste.

While aspects and exemplary embodiments of the present invention will be described in connection with a particular medical waste collection and disposal process, various aspects of the invention may be used in other suitable medical and non-medical applications, such as medical or non-medical cleaning devices and processes.

To attain the advantages and other features of aspects of the present invention, as embodied and broadly described herein, one exemplary aspect may provide a fluid collection system having a flexible liner. The fluid collection system may include a container having a top opening, a lid configured to close the top opening, and the flexible liner attached to the lid. The liner may be interposed between the lid and the container when the lid closes the top opening. The liner and the lid may define a substantially sealed interior space therebetween. The lid may include an access port through which the interior space receives fluid. The flexible liner may also be configured to collapse into a substantially collapsed state as the fluid is removed from the interior space.

Additional objects and advantages of aspects of the present invention will be set forth in part in the description which follows, and in part will be obvious from the description, or may be learned by practice thereof. Such objects and advantages may be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

A better understanding of the invention will be had upon reference to the following description in conjunction with the accompanying drawings in which like reference numerals represent like parts.

FIG. 4 is a schematic illustration of a cavity for receiving a liquid collection bag, which is defined by a removable housing, according to an exemplary implementation in accordance with aspects of the present invention.

FIG. 5 is a partial exploded view of a portion (dotted circle) of the removable housing shown in FIG. 4, with an exemplary liquid collection bag attached.

FIGS. 11(a)-(c) are perspective views of an exemplary collection system, in accordance with aspects of the present invention.

FIGS. 15 and 16 are perspective views of a disposable, separable tube junction, in accordance with aspects of the present invention.

FIG. 17 is a perspective view of a liquid collection bag, in accordance with aspects of the present invention.

FIGS. 27-33 are schematic illustrations of a liquid collection and disposal system, in accordance with aspects of the present invention.

FIG. 35 is a perspective view of a piston, usable in accordance with aspects of the present invention.

FIG. 36 is a perspective bottom view of the raised bottom of the piston shown in FIG. 35.

FIG. 37 is a perspective view of the piston of FIG. 35, with the raised bottom shown in FIG. 36 removed.

FIG. 38 is a cross-sectional view of the piston shown in FIG. 35.

FIG. 39 is a cross-sectional view of a piston, in accordance with aspects of the present invention.

FIG. 40 is a perspective view of the piston shown in FIG. 39.

FIG. 41 is a perspective of the piston shown in FIGS. 39 and 40, as seen from a bottom view.

FIGS. 42(a) and 42(b) depict aspects of an exemplary disposal system, in accordance with aspects of the present invention.

FIGS. 43(a) and 43(b) are views of another exemplary liquid collection and disposal system, in accordance with aspects of the present invention.

FIGS. 48 and 48(a) are perspective views illustrating an exemplary engagement between a liquid disposal station and a lid of a liquid collection system, in accordance with aspects of the present invention.

FIGS. 49, 49(a), 49(b), and 50 are cross-sectional views illustrating the exemplary engagement of the devices of FIG. 48, as located between the disposal hose junction of the liquid disposal station and an evacuation port of the lid.

DETAILED DESCRIPTION

Reference will now be made in detail to aspects of the present invention, examples of which are illustrated in the accompanying drawings. Wherever possible, the same reference numbers will be used throughout the drawings to refer to the same or like parts.

Figure 1:
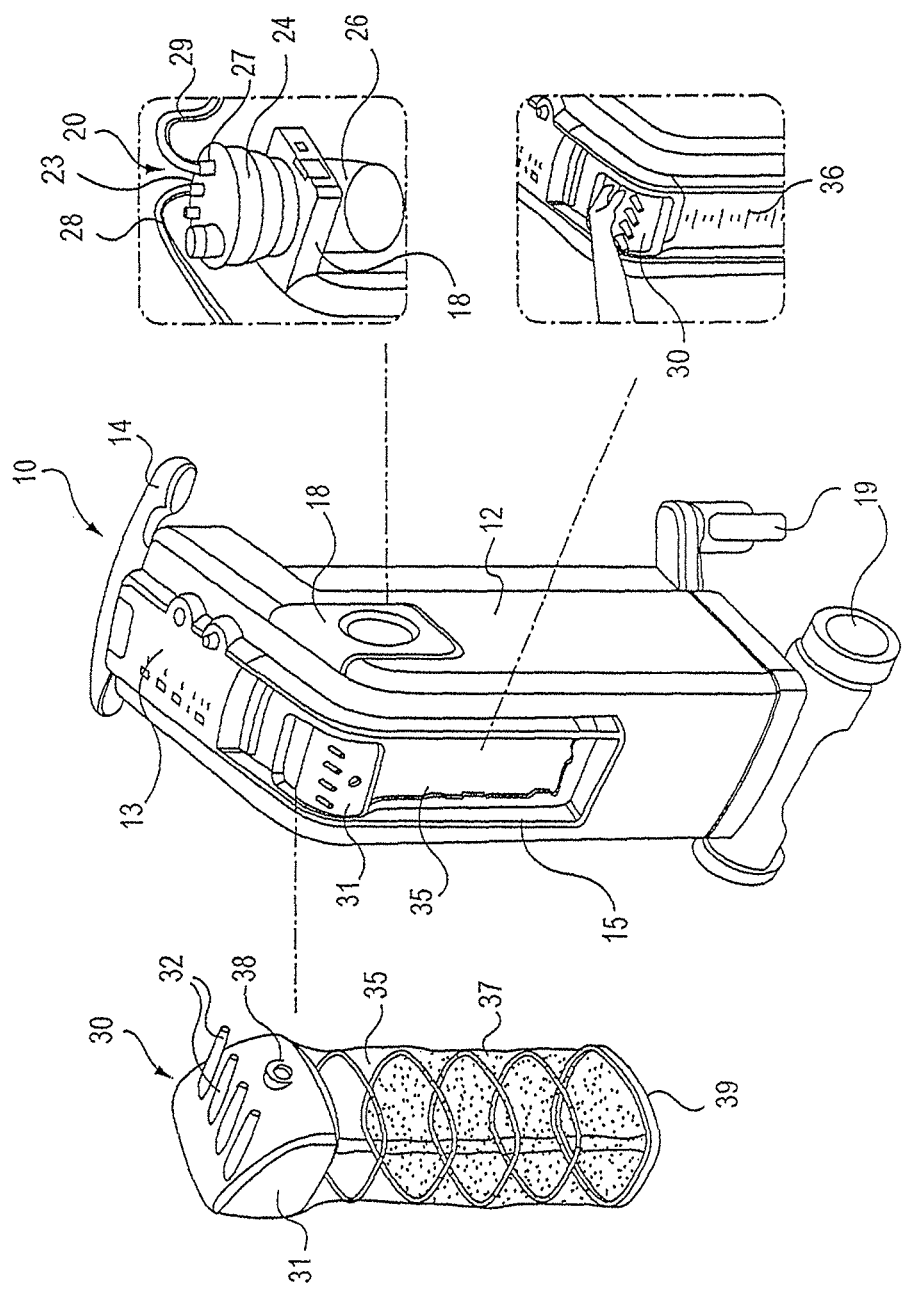
FIG. 1 is a perspective view of a liquid collection system, in accordance with exemplary aspects of the present invention, illustrating various components.
Figure 2:
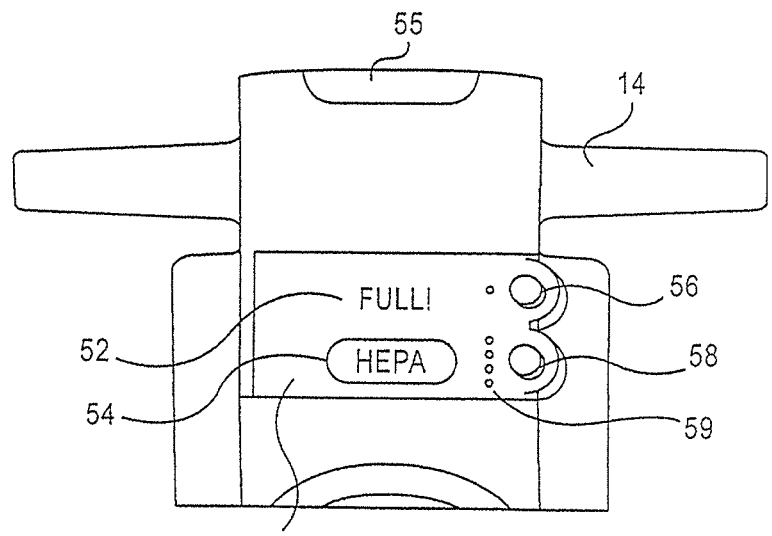
FIG. 2 is a partial perspective view of an exemplary embodiment of an interface board for the system shown in FIG. 1.
Figure 3:
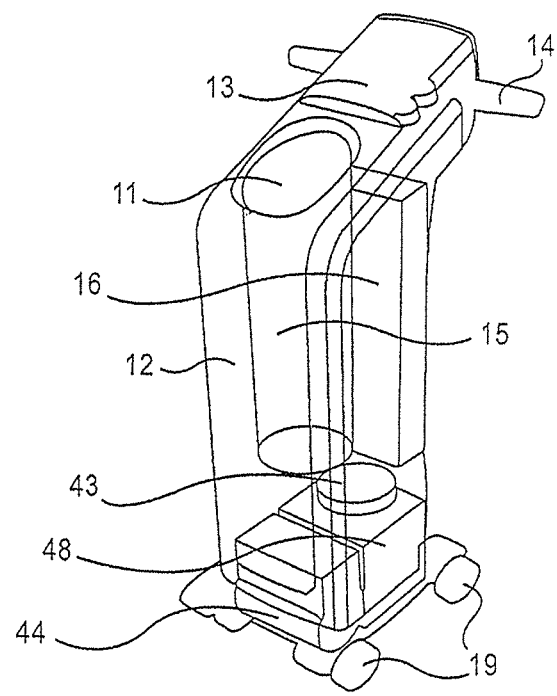
FIG. 3 is a schematic illustration of various components inside the liquid collection system of FIG. 1.

FIGS. 1-3 show a portable fluid collection system 10 (herein also referred to interchangeably as a liquid collection system), according to exemplary aspects of the present invention. The system 10 includes a main body, also interchangeably referred to herein as a container receiving housing, 12 defining a cavity 15 for receiving a fluid collection container 30 (also herein referred to interchangeably as a liquid collection container) shown in this figure as an exemplary fluid collection bag (also herein referred to interchangeably as a liquid collection bag). The liquid collection container is also interchangeably referred to herein as a "liquid collection bag." The system 10 may also include a handle 14 and wheels 19 to facilitate transport of the system 10. The wheels 19 may be permanently fixed to the main body 12 or, alternatively, to a support platform on which the main body 12 may be placed. The system 10 may also include a cord reel 43 for storing a power cable.

The term "liquid," as used herein, does not merely refer to a state of matter as defined in the thermodynamic and/or fluid mechanics art. Instead, the term "liquid" also includes any solid particles or gases that may incidentally flow with a liquid medium (e.g., irrigation fluid or blood) or that may be intentionally collected using a liquid medium. For example, when the fluid collection system 10 is used in a surgical procedure, the term "liquid" may refer to a combination of liquid medium (e.g., irrigation fluid, blood, and other bodily liquid from the patient) and any solid particles including, but not limited to, resected tissue removed from the patient's body or harmful particles mixed with smoke or other particulates and/or gases such as may occur in connection with laser, cauterization, and/or other medical procedures. The term "fluid," as used herein may also refer to a liquid medium, solid particles, smoke, gases, particulates, and combinations thereof.

The main body 12 may also include a container holder for receiving a back-up storage container 20, such as a suction canister. The holder may include a foldable mounting bracket 18 having an opening sized and configured to receive the container 20. When not in use, the bracket 18 may be folded substantially flush with a side surface of the main body 12, so as not to interfere with the normal use of the system 10. Alternatively, the holder may include a planar support structure (e.g., a flat structure without a hole) on which the container 20 may be rested. Alternatively still, storage container 20 may be affixed to the main body 12 by a sliding-type bracket, such as shown in U.S. Pat. No. 5,470,324, which is hereby incorporated by reference herein in its entirety. As a further modification, vacuum pressure may be supplied to the interior space of the container 20 directly through the bracket, such as via a connector provided on the sidewall of the main body 12.

As shown in FIG. 3, the main body 12 may include one or more storage units 16 for storing, for example, medical supplies associated with the system 10. In some exemplary embodiments, the storage units 16 may be configured to store multiple liquid collection bags 30.

The system 10 may include a vacuum pump 44 for supplying a suction force to the cavity 15 and to the liquid collection bag 30. Although not shown in FIG. 3, the system 10 may include appropriate suction conduits connecting the vacuum pump 44 to the cavity 15 and the liquid collection bag 30. In certain exemplary embodiments, instead of, or in addition to, providing the vacuum pump 44 in the main body 12, an alternative suction source may be separately supplied to the system 10. For example, suitable conduits, tubing, fittings, connectors, and/or other hookups may be provided on the main body 12 to allow connection to an external source of vacuum or suction force, such as a wall vacuum in a hospital setting. The availability of an alternative suction source may enable a continuous liquid collection process even when the vacuum pump 44 malfunctions or becomes otherwise unavailable, for example.

Figure 6:
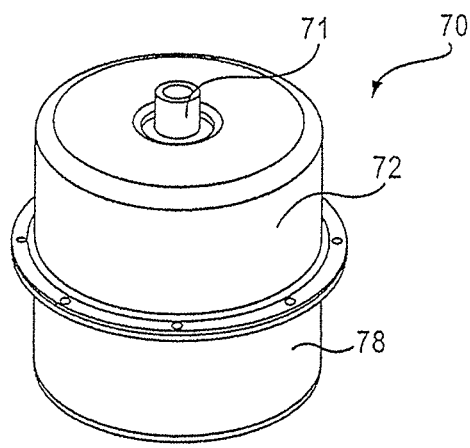
FIG. 6 is a perspective view of a filter, in accordance with exemplary aspects of the present invention.
Figure 8:
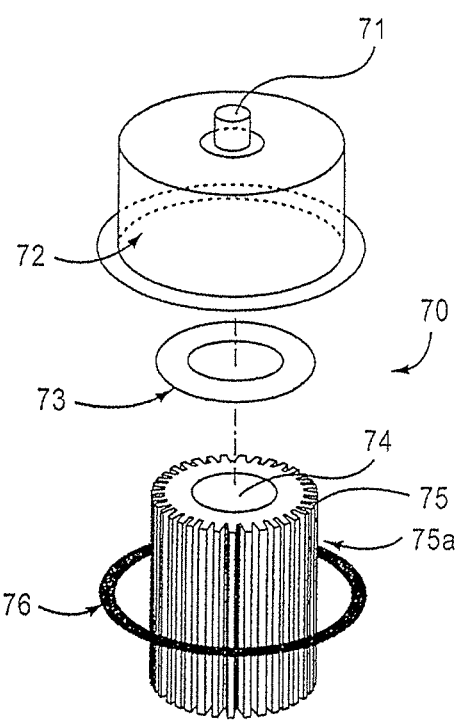
FIG. 8 is a perspective view of the filter of FIG. 6, illustrating various components.
Figure 7:
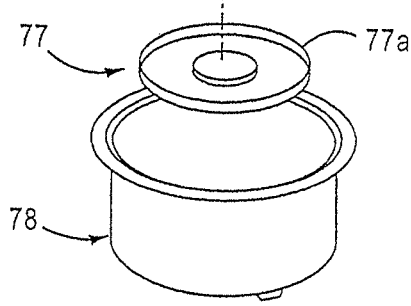
FIG. 7 is a bottom view of the exemplary filter of FIG. 6.
Figure 7A:
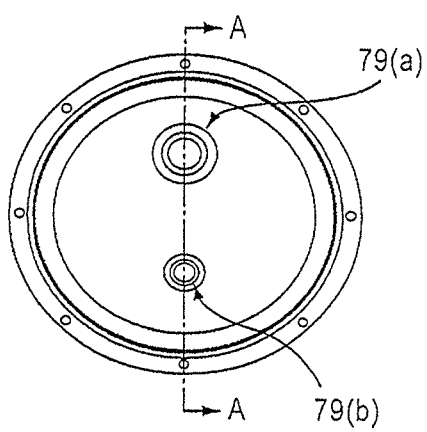
FIG. 7(a) is a bottom view of another exemplary filter in accordance with aspects of the present invention.
Figure 43:
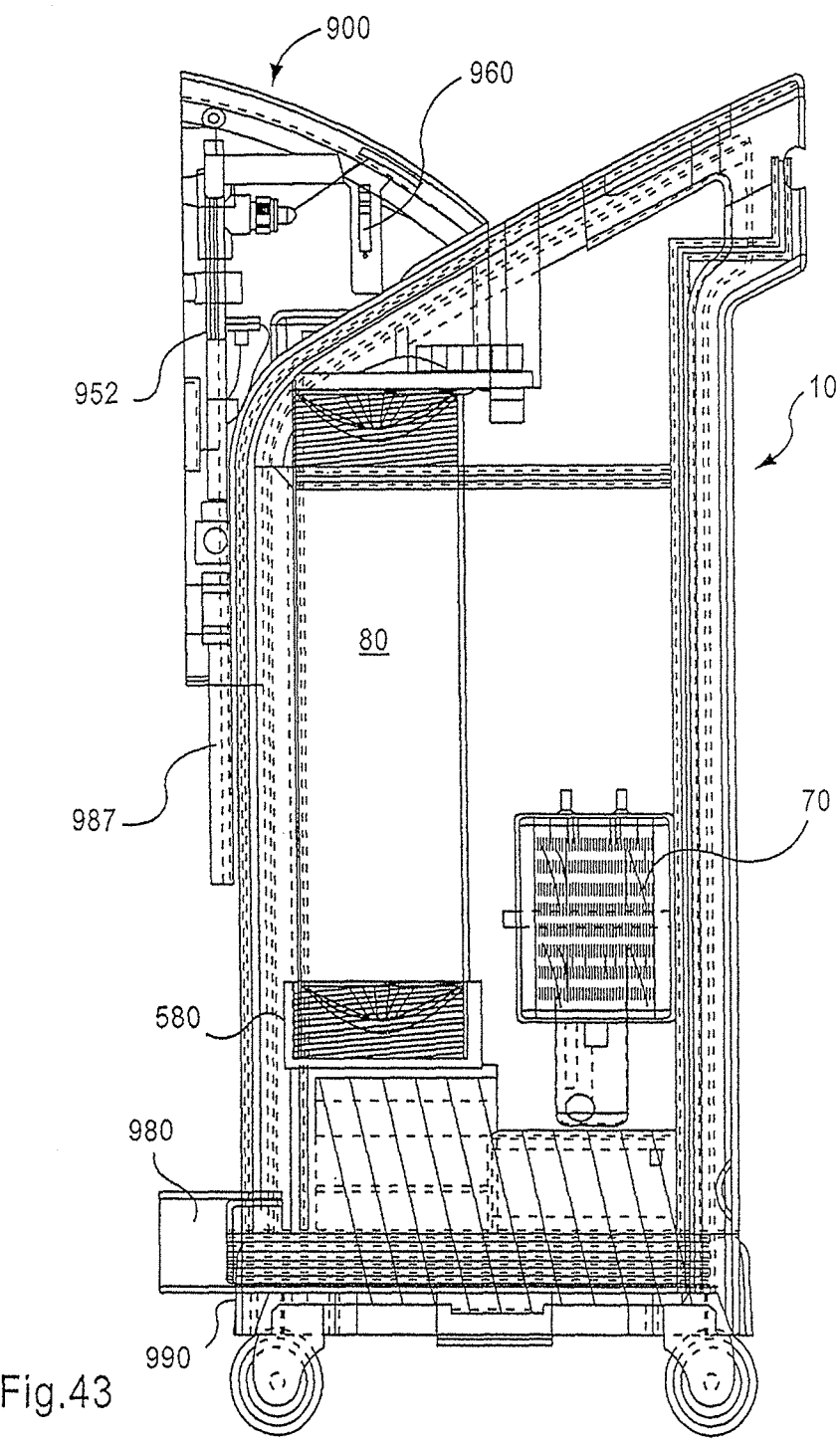
FIG. 43 is a see-through view of a liquid collection and disposal system, in accordance with aspects of the present invention.

In certain variations, the system 10 may include a filter unit 70 (e.g., a HEPA filter) to prevent relatively large particles from entering the vacuum pump 44. Referring to FIGS. 6-8, the filter unit 70 may include a filter housing comprised of an first housing portion 72 and a second housing portion 78 configured to mate with one another to define a substantially enclosed interior space for receiving a filter 75. Although FIGS. 6-8 show housing portion 72 on top and housing portion 78 on bottom, this may be reversed. For example, FIG. 43 depicts the filter 70 with housing portion 72 as a lower housing portion and housing portion 78 as an upper housing portion. In this description, housing portion 72 will be referred to as the first housing portion and housing portion 78 as the second housing portion, as shown in FIG. 43. The first housing portion 72 may define an outlet opening 71 for connection to a vacuum pump 44 (see also FIG. 23 for connection between HEPA filter unit 870 and vacuum pump 860), for example, and the second housing portion 78 may define one or more inlet openings 79a, 79b, 79c for connection to various components utilizing the suction force generated by the vacuum pump 44. In such applications, the number of inlet openings 79a, 79b, 79c may depend upon the number of components that require connection to the vacuum pump 44. For example, if the system 10 includes only one component that requires connection to the vacuum pump 44, the second housing portion 78 may include only one inlet opening 79a. If, however, the system includes multiple components that require connections to the vacuum pump 44 (e.g., similarly to the one shown in FIG. 23), the second housing portion 78 may include as many inlet openings 79a, 79b, 79c as needed by the system 10. For example, as shown in FIG. 7(a), the second housing portion may include two inlet openings.

The first housing portion 72 and the second housing portion 78 may be joined together via one or more screws, or other attachment features, such as a suitable snap-fastening or thread-fastening mechanism or any other suitable fastening mechanism. In the embodiment shown in FIG. 8, a sealing gasket 76 may be disposed between the first housing portion 72 and the second housing portion 78 to seal the interface therebetween. The first housing portion 72 and the second housing portion 78 may be readily separable to facilitate replacement of the filter 75 disposed therein.

The filter 75 may comprise a microporous (HEPA-grade) material. The filter 75 may have a generally cylindrical shape defining a hollow internal space 74 in fluid communication with the outlet opening 71 of the first housing portion 72. The filter 75 may be formed of a hydrophobic material, such as expanded PTFE on thermally fused polyester (e.g., Tetratex© ePTFE available from Donaldson Company, Inc. of Minneapolis, Minn.). The filter 75 may have hydrophobic characteristics that serve as a safety valve for preventing water from flowing into the vacuum pump 44, as will be described further herein with reference to FIG. 23, for example.

As shown in FIG. 8, the filter 75 may be positioned between an upper gasket 73 and an end cap 77. The upper gasket 73 may be made of polychloroprene material (e.g., neoprene) or microcellular urethane foam (e.g., Poron®), for example. The upper gasket 73 seals or partially seals the contact space between the top surface of the filter 75 and the first housing portion 72. In some exemplary variations, to enhance the sealing effect, the filter unit 70 may be configured such that, when the first housing portion 72 and the second housing portion 78 are joined together to compressibly enclose the filter unit 70, the filter 75 presses the upper gasket 73 so as to slightly compress the upper gasket 73.

The end cap 77 is configured to receive one end of the filter 75. The end cap 77 may define an annular groove 77a configured to receive the second end of the filter 75, for example, as shown in FIG. 8, for more securely holding the filter 75 in place. The end cap 77 is impermeable to fluid, thereby preventing any fluid from escaping via the first end of the filter 75. The space between the end cap 77 and the second housing portion 78 may define one or more flow paths (e.g., via reinforcement ribs extending radially). Thus, all of the fluid entering the filter unit 70 through the inlet openings 79a, 79b, 79c may flow around the end cap 77, pass through the side wall 75a of the filter 75, and exit the filter unit 70 through the internal space 74 and the outlet opening 71.

The system 10 may include an interface board 13 for enabling control of various features of the system 10. For example, as shown in FIG. 2, the board 13 may include a selection button 56 for controlling the power supplied to the system 10 and a selection button or variable control knob 58 for regulating suction power. The interface board 13 may also include one or more visual or audible indicators that provide various information relating to operational characteristics and/or status of the system 10. For example, the interface board 13 may include one or more light indicators 55, 52, 54 for indicating whether the system 10 is ready for operation, whether the storage bag 30 is full (or filled to an indicated level), or whether the filter 70 needs to be replaced. The board 13 may also include a vacuum level indicator 59 to provide visual feedback on the level of suction pressure as controlled by the variable control knob 58. An audio source may be provided to supply audio indicators alone or in conjunction with one or more of the visual indicators.

Another illustrative embodiment of an interface board 13 is shown in FIG. 2(*a*). In this variation, the interface board 13 may include a power light 150 that indicates that the system is connected to a power source, a selection button 151 for turning on/off the suction pressure, and a variable control knob 152 for regulating the level of suction provided. The interface board 13 may further include various visual and/or audible indicators that provide information regarding the operational characteristics and/or status of the system 10. For example, the interface board may include a plurality of lights 152a, 152b, 152c, and 152d that indicate the level of the suction pressure. In the example shown in FIG. 2(*a*), four lights are used, each indicating a 25% increase in the range of the control mechanism for the level of the suction pressure. When only one light 152a is lit, the device operates up to 25% of the range of the control mechanism. As the knob is turned, the suction pressure level increases. As the suction pressure increases beyond 25% of the range of the control mechanism, a second light 152b turns on, identifying that the device is operating between 25% and 50% of the range of the control mechanism for the level of suction pressure, and so on.

The interface board may also include any one or more visual indicator that the liquid collected in the liquid collection bag has reached a predetermined or selected level. The visual indicator may include a light or other visual indicator on the interface board. The visual indicator may also include a light or other display for projection onto a wall or ceiling of the room in which the system is located. For example, a visual indicator may show that the bag is "almost full" when the liquid collected in the bag reaches more than 80% of the capacity of the bag. This indication may also or alternatively occur at 85%, 90%, or 95%, for example.

In addition to a visual indicator that the liquid collection bag is almost full, an audible indicator may also be provided. The audible indicator may continue to notify a user that the liquid collection bag is nearly full at regular intervals, at preselected levels, etc. For example, an audible alarm may sound when the liquid collection bag reaches more than 80% of its capacity and may sound again at a predetermined time interval, such as every few seconds, up to every few minutes, following the 80% alarm. For example, the alarm may occur at a time interval between 20 seconds and three minutes. In another variation, the audible alarm may also be configured to sound when the liquid collection bag reaches 80% of its capacity, and again when it reaches 85%, 90%, and 95% of its capacity. The interface board may include a selection button 153 for enabling/disabling the audible alarm. The interface board may include additional visual indicators 154 to signal that the filter should be replaced, or that the bag is full.

The change filter visual indicator 154 may, in an exemplary implementation, indicate that the filter needs to be changed because the system has been in use for a predetermined number of hours. Thus, the change filter indication may function like a timer that tracks the amount of time that the system is actually used to collect liquid. Alternatively, the change filter indication may include a timer that indicates that a predetermined amount of time has passed, regardless of the amount of use, or may include a sensor that detects the state of the filter or the state of air flow through the filter, etc.

The liquid collection bag 30 may be a disposable unit. As shown in FIG. 1, the collection bag 30 may include a lid 31 and a flexible liner 35 attached to or integrally formed with the lid 31, such that the liner 35 and the lid 31 define a substantially sealed interior space therebetween. In some exemplary variations, such as the variation shown in FIG. 5, a lid 530 and a liner 575 may be manufactured separately, but include a suitable attachment mechanism, such as a snap ring 571 that secures the top perimeter of the liner 575 between the snap ring 571 and an annular groove 568 formed on an inner surface of the lid 530. That is, liner 575 is draped over an upper surface of the ring 571, and the ring 571 is then snapped into the annular groove 568, thereby retaining the liner 575 between the snap ring 571 and the annular groove 568. As shown, snap ring 571 is positioned "outside" the interior space of the liner 575 by draping the liner 575 over the snap ring 571 from the inside. Alternatively, snap ring 571 might be positioned "inside" the interior space of the liner 575 by draping the liner 575 inwardly over the upper surface of the ring 571 from the outside. Other suitable attachment mechanisms may be used alternatively or additionally. For example, the liner 575 may be hot melted to the lid 31.

Figure 10:
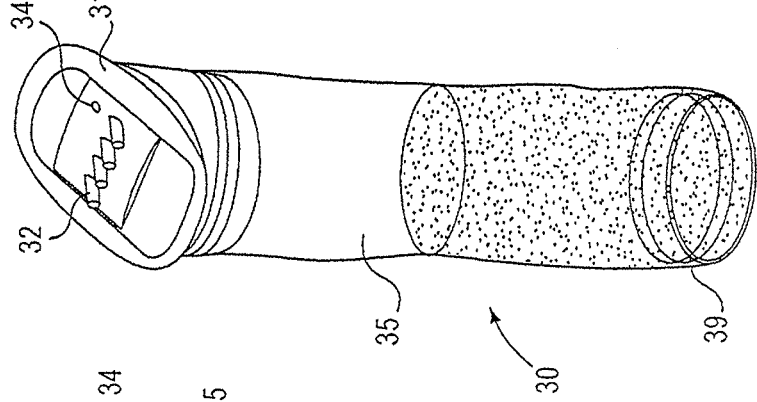
FIG. 10 is a perspective view of the liquid collection bag during a liquid collection stage.

The flexible liner 35 may comprise a sufficiently durable, yet collapsible material, so that, upon applying a negative pressure inside the interior space (e.g., during and/or after fluid is removed from the interior space), the liner 35 can collapse into a smaller volume. In some exemplary applications, the liner 35 may additionally include one or more support structures that guide the liner 35 to expand/extend and collapse/retract in a predetermined manner. For example, as shown in FIG. 1, the liner 35 may include a plurality of support rings or a spiral shaped support 37 (e.g., ribs or spirals made of flexible wires), spaced apart from one another along the length of the liner 35, so that the liner 35 may expand and collapse in a bellow-like manner. The term collapse as used herein, includes and is interchangeably referred to herein as actions in which the sides of the liner 35 fall in, cave in, retract, unextend, compress in, fold, or roll, among other things, and/or which may optionally be forced or otherwise collapsed via operation of a scraping or other squeegee type apparatus. Alternatively, as seen in FIG. 10, the liner 35 may not include such support rings 37. In either case, in variations the liner 35 extends and retracts along its longitudinal axis. Other variations may include other directions in which the liner 35 extends and retracts.

At least the front portion of the main body 12 may comprise a transparent or translucent material that allows visualization of the liquid being collected in the collection bag 30. In some exemplary implementations, the front portion of the main body 12, the liner 35 and/or the cylindrical body 86 (FIG. 4), may include gradation marks 36 to indicate the amount of liquid being collected in the collection bag 30, as shown in FIG. 1.

The lid 31 may include one or more collection ports 32 configured to connect to various medical devices that draw liquid into (or extract liquid from) the collection bag 30. The collection ports 32 may have various different sizes and shapes to accommodate various medical devices that may be used with the system 10. The lid 31 may also include a vacuum port 33 (see FIG. 12) for connecting to the vacuum pump 44 to supply suction force to the interior space of the collection bag 30.

Figure 9:
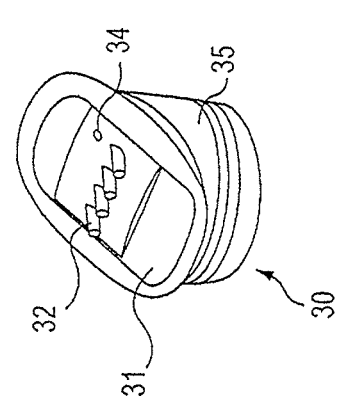
FIG. 9 is a perspective view of a liquid collection bag in a collapsed state, in accordance with aspects of the present invention.
Figure 11:
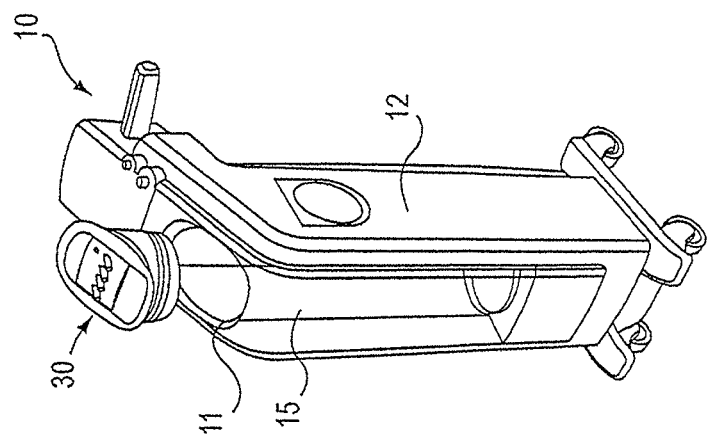
FIG. 11 is a perspective view of the collection system, illustrating a placement of the liquid collection bag into a cavity of the liquid collection system, in accordance with aspects of the present invention.

In an exemplary implementation, as shown in FIGS. 9-11, the lid 31 may also include a back-up vacuum port 34 for connecting to a back-up storage container 20 in case the collection bag 30 becomes full or inoperable during a liquid collection process. The back-up vacuum port 34 may be in communication with the vacuum port 33, such that the vacuum pressure supplied by the vacuum pump 44 can also supply vacuum pressure to the back-up storage container 20 via the backup vacuum port 34. Alternatively, the backup vacuum port 34 may be in communication with an alternate source of vacuum pressure (e.g., wall vacuum in a hospital setting). Alternatively or additionally, the backup storage container 20 may be connected to one or more of the collection ports 32 using, for example, conventional tubing so as to supply vacuum pressure to the backup storage container 20. In some alternative variations, the backup vacuum port 34 may be located on the main body 12, rather than on the lid 31, and connected either to the vacuum pump 44 or an alternate source of suction force. The operation of the back-up storage container 20 will be explained in more detail later with reference to FIGS. 13 and 14.

The lid 31 may also include a discharge port 38 for evacuating the collected liquid from the collection bag 30, such as after a medical procedure is completed. In an alternative variation, the lid 31 may not have any separate discharge port 38. Instead, one or more of the collection ports 32 may be used to empty the collection bag 30.

As mentioned above, the main body 12 defines a cavity 15 configured to receive the liquid collection bag 30. The cavity 15 may have various sizes and shapes. By way of example only, the cavity 15 may have a volume of approximately 12 L, 15 L, 20 L, etc. Alternatively, even very small volume bags 30 could be used. When having a relatively large volume, the liquid collection bag 30 may be used continuously over multiple medical procedures without emptying the collection bag 30.

In some exemplary embodiments, a cavity 85 may be defined by a receptacle 80 removably arranged within the main body 12, as shown in FIG. 4. In certain variations, the cavity 85 may be exposed to various chemicals and/or cleaning processes (e.g., when scrubbing), which may cause defects on the surface of the cavity 85. Such surface defects on the cavity 85 may reduce the visibility inside the cavity 85, and it may be desirable to replace the cavity 85 in such event. Thus, providing the removable receptacle 80 may enable easy replacement of the cavity 85 without replacing the entire liquid collection system 10.

As shown in FIG. 4, the receptacle 80 may include a generally cylindrical body 86 and an end cap 88 for closing the bottom end of the cylindrical body 86. Alternatively, other cross-sectional shapes may be used, such as hexagonal, rectangular, square, or triangular, curved, as well as other suitable shapes. Between the cylindrical body 86 and the end cap 88, an intermediate tubular member 87 may be disposed. By way of example only, the cylindrical body 86 may comprise a clear acrylic material, and the end cap 88 and the tubular member 87 may comprise a PVC material (or other suitable material, such as ABS). The tubular member 87 and the end cap 88 may be welded or otherwise adhered together (e.g., via a suitable adhesive material), and the cylindrical body 86 may be removably attached to the tubular member 87 via one or more annular projections 86a extending from the cylindrical body 86 receivable in corresponding annular grooves formed on the inner surface of the tubular member 87. In case the projections 86a are made of a material that is different from that of the cylindrical body 86, a two-shot molding process, generally known in the art, may be used to integrally form the projections 86a with the cylindrical body 86. In an alternative variation, one or more O-rings may be used in lieu of projections 86a. To separate the cylindrical body 86 from the tubular member 87, the cylindrical body 86 may be pulled away from the tubular member 87 using a predetermined level of force. The projections 86a or O-rings may then be resiliently deformed and released from the corresponding grooves of the tubular member 87. A piston, which will be described in detail later with reference to FIGS. 27-33 and 35-41, may be slidably disposed inside the receptacle 80.

One of the purposes of using the tubular member 87 and the end cap 88 arrangement is to allow replacement of the cylindrical body 86 only, so that the tubular member 87 and the end cap 88 may be reused with a new cylindrical body 86. Conversely, only the tubular member 87 and the end cap 88 may be replaced, while the cylindrical body 86 may be reused. If such replacement scheme is not desired, the receptacle 80 may be integrally formed as a single piece without any separate end cap 88 and the tubular member 87.

In certain variations, the receptacle 80 may be provided with an interface connector to facilitate engagement of the receptacle 80 with the lid of a liquid collection bag in a manner so as to enhance sealing therebetween. For example, FIGS. 4 and 5 show an exemplary interface connector 81 configured to be placed on the top portion of the cylindrical body 86 of the receptacle 80. The interface connector 81 may comprise a flexible material, such as a polymer, elastomer, or rubber. By way of example only, the flexible material may have a durometer ranging from about 50 to about 70. The interface connector 81 may include an annular member configured to removably engage with the top portion of the cylindrical body 86. For example, the top portion of the cylindrical body 86 may include a flange 83 extending circumferentially along its external side wall, and the interface connector 81 may have a corresponding snap-on structure configured to engage the flange 83.

As best shown in FIG. 5, the interface connector 81 may include a resilient seal flap 84 extending circumferentially downwardly at an angle. A lid 530 may include a rigid rib 564 configured to contact the seal flap 84 when the lid 530 is inserted into the top opening of the receptacle 80. As the lid 530 is inserted, the rigid rib 564 may press down on a surface of the seal flap 84, causing the seal flap 84 to resiliently deform from an unstressed state (e.g., indicated by a dotted line) to a stressed state. At this stressed state, the seal flap 84 exerts a counteracting force against the rigid rib 564, which enhances the sealing effect between the lid 530 and the receptacle 80. To further enhance the sealing effect, the interface connector 81 may include a pressure rib 82 extending from its top surface to contact with a bottom surface of the peripheral edge of the lid 530.

The collection bag 30 may be delivered to the medical facility in its fully-collapsed state, as shown in FIG. 9. The collapsibility of the collection bag 30 into a smaller volume may reduce not only the volume of the medical waste generated, but also the storage area required to store the collection bags 30 prior to their use. For example, in an exemplary implementation, instead of storing the collection bags 30 in a separate storage location, they may be stored inside the storage space 16 of the main body 12 for convenient access. Alternatively, the exterior of the main body 12 may have one or more attachment members to which extra collection bags 30 may be secured or otherwise attached.

During use, the liner 35 is extended to receive fluid, as shown in FIG. 10. As will be explained in detail herein, while the collection bag 30 is being emptied, the liner 35 may collapse again into a state that is substantially similar to its original fully-collapsed state. After an acceptable quantity of liquid is removed from the collection bag 30, it may be removed for disposal in its near-collapsed state.

To begin a liquid collection process, the collection bag 30 is positioned, in its collapsed state, on the mouth portion 11 of the cavity 15, as shown in FIG. 11. An unused, collapsed liquid collection bag may include a holding mechanism such as a strap or band that assists in maintaining the liner portion of the collection bag in a suitable collapsed position. This holding mechanism assists in maintaining the flexible liner in a suitable collapsed position and holds the flexible liner away from any seals on the lid. This feature allows the bag to be easily positioned at the mouth portion 11 of the cavity 15 and assists in preventing the flexible liner from being pinched between a seal on the lid and the mouth portion 11 of the cavity. The holding mechanism may be configured of a breakable material that breaks, for example, when suction pressure is applied to expand the bag into the interior of the cavity, or as collected liquid expands the bag. Thus, a user does not need to break the band prior to placing the collection bag 30 on the mouth portion 11 of the cavity 15. The holding mechanism may comprise, for example, paper, plastic, or other suitable material. Once positioned in place, the lid 31 of the collection bag 30 may sealingly engage the mouth portion 11 of the cavity 15, so as to form a substantially air-tight enclosure inside the cavity 15 and exterior to the collection bag 30. FIGS. 11(*a*), 11(*b*), and 11(*c*) show various features of an exemplary fluid collection system, in accordance with aspects of the present invention.

Figure 12:
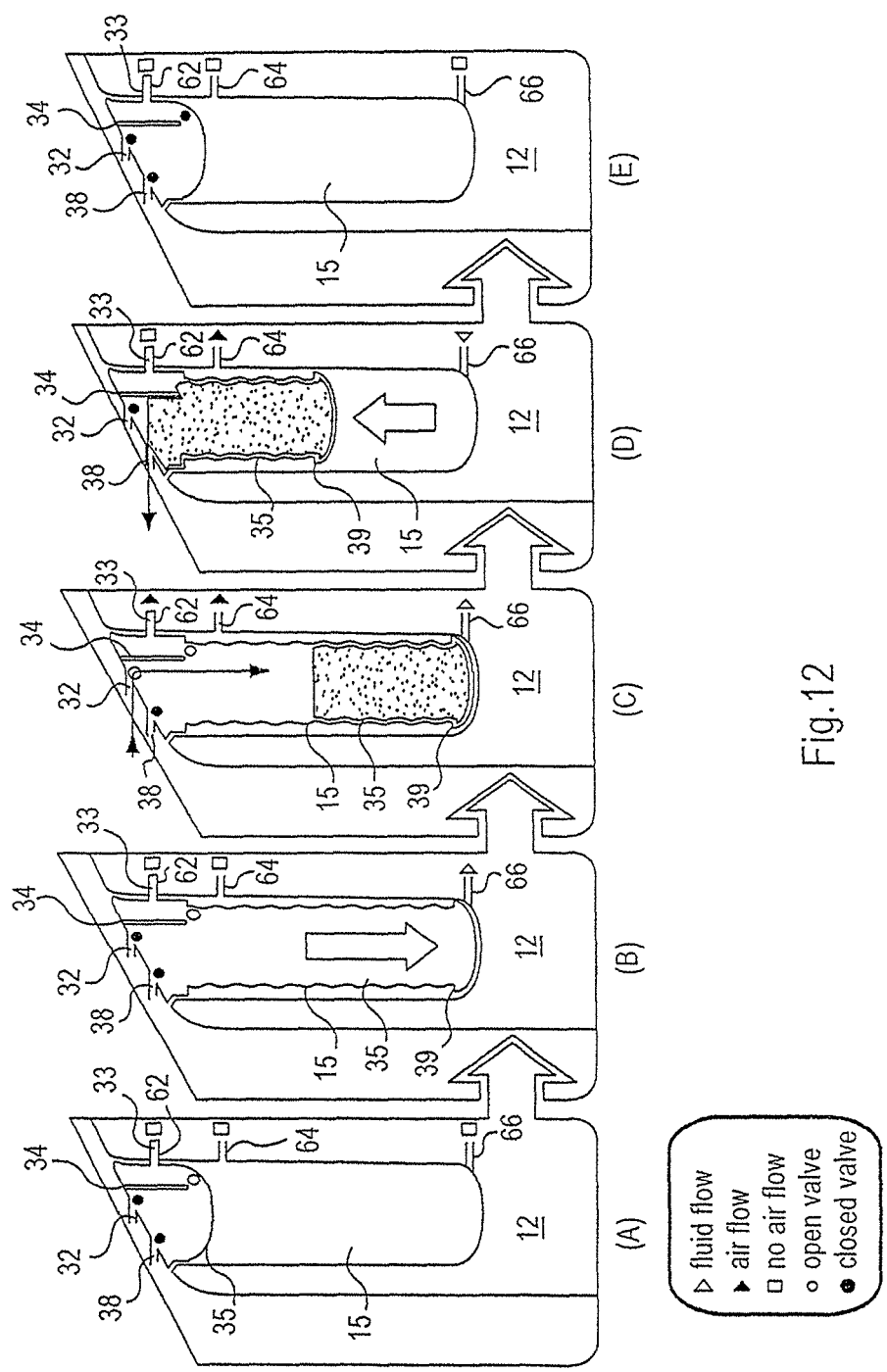
FIG. 12 is a schematic illustration of a liquid collection and disposal sequence, in accordance with aspects of the present invention.

FIG. 12 illustrates a fluid collection and disposal sequence, according to exemplary aspects of the present invention. As shown in FIG. 12, the cavity 15 may include three vacuum connectors: a first connector 62, a second connector 64, and a third connector 66, each of which may be connected to a vacuum pump 44 positioned at the lower portion of the main body 12, or alternatively may be connected to an external source of suction pressure. As discussed above, a filter (e.g., filter 70 shown in FIGS. 6-8) may be disposed between the vacuum pump 44 and at least one of those three vacuum connectors. When the collection bag 30 is placed in the cavity 15, the vacuum port 33 of the lid 31 may automatically connect to the first connector 62, so as to supply suction force to the interior space of the collection bag 30. This suction force, in turn, is communicated to the collection ports 32. Each of the vacuum connectors 62, 64, 66 may include a suitable valve to selectively open and close communication with the vacuum pump 44 or to an alternate source of vacuum pressure. In some exemplary variations, the valve associated with the third connector 66 may comprise a three-way valve that can selectively establish fluid communication between the cavity 15 (exterior to the bag 30) and atmosphere. As will be explained in greater detail below, this valve arrangement may allow the pressure inside the cavity 15 to reach atmospheric pressure during an evacuation process, so as not to interfere with the collapsing of the liner 35. Alternatively, the second connector 64 may be open to vacuum pressure or may be closed off entirely, so as to provide selective regulation of air pressure within the cavity 15 exterior to the collection bag 30.

The collection bag 30 may also include various valves associated with the collection ports 32 and the discharge port 38. The collection bag 30 may also include an overflow valve associated with the vacuum port 33. As will be discussed in greater detail herein, the overflow valve may be configured to close a passageway leading to the vacuum port 33 when the liquid level reaches the elevational position of the overflow valve or when the liquid level reaches some preselected cutoff elevational position spaced below the overflow valve by some distance. In addition, a sensor may be provided to detect when the level of the liquid has reached a preselected position, upon which the sensor may then provide visual and/or audio feedback to the operator to indicate that the level of liquid within the collection bag 30 is nearing the overflow valve position. These valves associated with the collection ports 32, discharge port 38, and vacuum port 33 are schematically shown in FIG. 12 with circles adjacent the corresponding ports. Solid circles represent closed valves, and open circles represent open valves.

Once the collection bag 30 is positioned within the cavity 15, the third connector 66 is opened to a suction force so as to be in fluid and/or pressure communication with the interior space of the cavity 15 external to the liner 35, thereby expanding the liner 35 into the cavity 15, as shown in FIG. 12(B). At this stage, although the figure shows that the valves associated with the collection ports 32 to be closed, at least one of the valves associated with the collection ports 32 and the discharge port 38 may be opened to allow air flow into the collection bag 30. This action draws the liner 35 into the cavity 15 without distorting the shape of the bag 30. Alternatively, some other vent may be provided, so as to allow ambient air to enter the interior space of the liner 35 as the liner is drawn down into the cavity 15. To draw the liner 35 into the cavity, the liner 35 may include a sealing member 39 (e.g., one or more sealing rings) positioned adjacent its bottom end.

In some exemplary variations, the sealing member 39 may include a more substantial structure, such as a molded plastic disc with sealing rings, as further described with reference to the embodiments shown in FIGS. 35-41. The sealing member 39 provides a substantially fluid-tight seal between the liner 35 and the surface defining the cavity 15. In an alternative implementation, the liner 35 may not be drawn into the bottom portion of the cavity 15 prior to receiving the liquid. Instead, as the liquid is being collected, the weight of the liquid may cause the liner 35 to expand into the cavity 15. Although the second connector 64 is shown in the figures to be located at a position vertically below the lowermost end of the collection bag 30, as shown in FIG. 12, it will be apparent to one of ordinary skill in the art that the second connector 64 may selectively not be opened to atmosphere until the lowermost end of the collection bag 30 is positioned vertically below the elevational position of the second connector 64.

Once the liner 35 is drawn into the cavity 15, communication with the first connector 62 is opened so as to supply suction force into the interior space of the collection bag 30 and, in turn, via the collection bag 30 to the collection ports 32. One or more medical devices, such as a suction catheter or patient tubing, may be connected to the collection ports 32 to draw liquid into the collection bag 30, as shown in FIG. 12(C). At this stage, the valves associated with the collection ports 32 may open to allow liquid to flow through the collection ports 32. During this liquid collection process, the second connector 64 may be opened to counterbalance the vacuum force applied to the interior space of the collection bag 30, so that the liner 35 may substantially maintain its normal shape. That is, opening the second connector 64 to a suction force thereby prevents the liner 35 from being drawn back up towards the lid 31 under the influence of the negative pressure within the interior space of the collection bag 30.

When the collection bag 30 is full and/or otherwise needs to be emptied, the collection system 10 may be transported to a disposal station to extract the collected liquid out of the collection bag 30, as shown in FIG. 12(D). At this stage, the valves associated with the collection ports 32 are closed, and the valve associated with the discharge port 38 opened. As mentioned above, as the collected liquid is drawn out of the collection bag 30, the second connector 64 is closed and the third connector 66 may communicate with atmosphere to increase the pressure inside the cavity 15 to atmospheric pressure. Maintaining the pressure inside the cavity 15 at atmospheric pressure may provide a sufficient pressure difference between the cavity 15 and the interior space of the collection bag 30, such that the liner 35 may collapse itself towards the lid 31 as the collected liquid is drawn out of the collection bag 30.

After an acceptable quantity of the collected liquid is removed from the collection bag 30, the liner 35 may return to a collapsed state, as shown in FIG. 12(E). For practical purposes, it may be sufficient for the liner 35 to compact itself enough so as to make subsequent handling and disposal thereof more efficient.

After the collected liquid is substantially removed from the collection bag 30, the valves associated with the collection ports 32, the discharge port 38, and the overflow valve are closed sufficiently to inhibit air from flowing into the interior space of the collection bag 30. Minimizing the amount of air flow into the collection bag 30 allows the collection bag 30 to remain in a substantially collapsed state for disposal. That is, large quantities of air will not be allowed to leak back into the interior space of the bag 30 once the vacuum pressure is removed therefrom. The used collection bag 30 may then be removed from the cavity 15 and, for example, placed in a red bag for disposal. Thereafter, a new collection bag 30 may be placed onto the cavity 15 and the fluid collection process described above may be repeated for the next series of medical procedures.

An additional safety feature is provided through at least one valve in the lid of the liquid collection bag 30. Implementations of such a valve are shown, for example, as valve 226 in FIGS. 27-28 and 31, valve 426 in FIG. 34, and valve 542 in FIG. 51. The valve may be an anti-drip check valve, such as a diaphragm valve, a biased valve, a two-way valve, such as any of a number of two-way valves manufactured by Liquid Molding Systems, Inc. (LMS) of Midland, Mich., etc., that also provides an access port to the collection bag. The valve provides a connection port, wipes the connector as it is removed, thereby preventing drips, and prevents liquid in the liquid collection valve from leaking out of the collection bag. For example, after an evacuation process, the valve prevents any remaining liquid in the collection bag from exiting the bag. Thus, a technician or other person involved in use of the system, including disposal of the liquid collection bag, is further protected from contact with the waste material collected in the liquid collection bag.

In certain circumstances, the collection bag 30 may become full or temporarily inoperable during a liquid collection process. To mitigate the negative effect this condition may have on a medical procedure, a back-up storage container 20 may be provided to temporarily store the liquid waste without interrupting the medical procedure. In the exemplary variation shown in FIGS. 13 and 14, the storage container 20 may have a frustoconical, generally tapering cylindrical body 26 and a cap 25 configured to close the top opening of the body 26 in a leak-tight manner. By way of example only, the storage container 20 may have a volume of approximately 3 L. Of course, the storage container 20 may have any other suitable shapes and sizes. The body 26 of the storage container 20 may be made of a material that is sufficiently strong to withstand the negative pressure applied thereto. In addition, the body 26 may comprise a sufficiently transparent material to allow visualization of the liquid being collected in the storage container 20.

Figure 13:
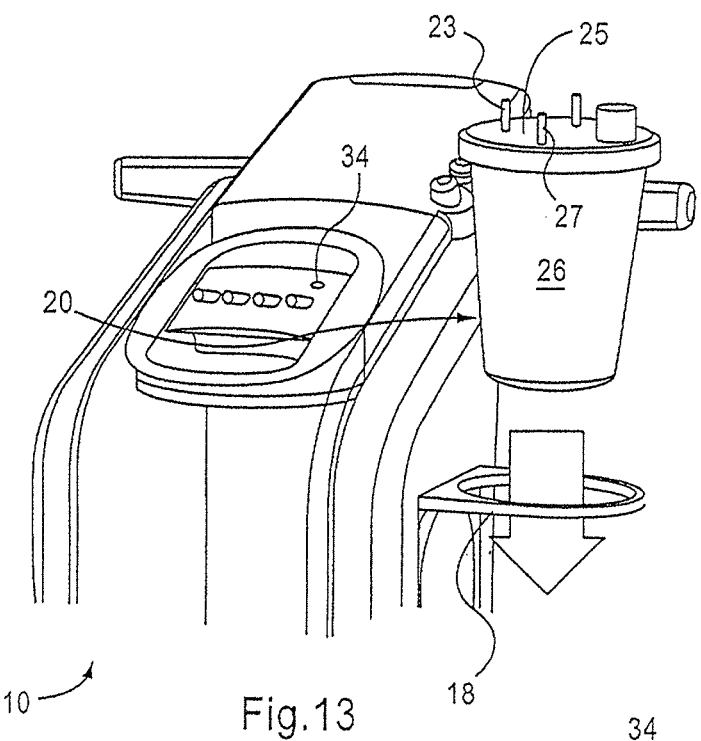
FIGS. 13 and 14 are schematic illustrations of a back-up storage container, in accordance with aspects of the present invention.
Figure 14:
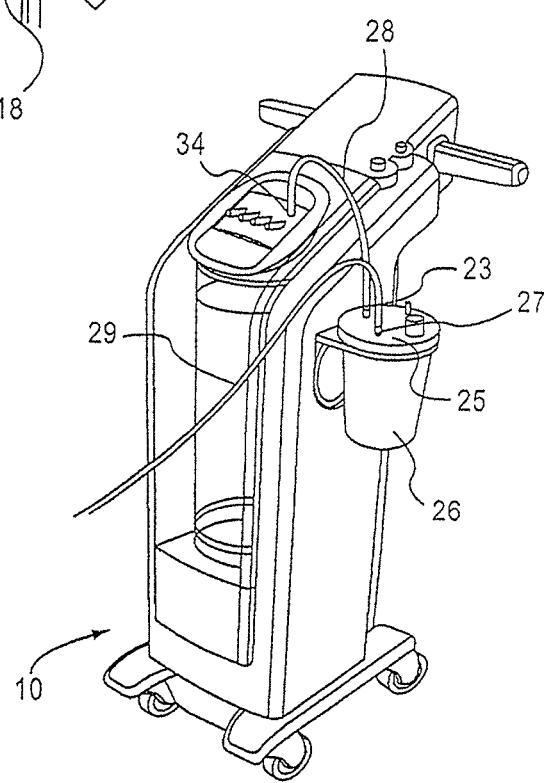

To engage the storage container 20 with the main body 12, the mounting bracket 18 may be extended laterally from the side surface of the main body 18. As shown in FIG. 13, the cylindrical body 26 of the storage container 20 may then be inserted into the opening of the bracket 18 to retain the container 20 in an upright position. In certain variations cap 25 may include at least two access ports: a vacuum port 23 and one or more collection ports 27. As shown in FIG. 14, the vacuum port 23 may communicate with the back-up vacuum port 34 of the collection bag 30 via a suitable suction conduit 28, and the collection port 27 may communicate with a proximal end of a suitable medical device attached to a collection tube (for the sake of illustration, both the suction instrument itself and the tubing used to connect to the suction instrument will be referred to using reference numeral 29) that is configured to draw liquid into the storage container 20. This arrangement allows the back-up storage container 20 to function as a separate, independent suction canister, thereby enabling continuous operation of the system 10, even when the collection bag 30 is full or inoperable. Sufficient valving and connections may be provided for either simultaneous operation of the main unit and the storage container 20, or independent operations thereof.

Although FIGS. 13-14 show a variation with a vacuum port 34 in the lid that provides for communication with the back-up storage container 26, in other variations, a vacuum port for the back up storage container may be provided in other locations on the main body. For example, FIGS. 1, 20, 22a, and FIGS. 53-55 illustrate variations of a collection container lid without a vacuum port for a back up storage container. For example, the lid may include an opening 546 configured to provide communication with an evacuation source. The opening may include a breakable member 544, a two-way check valve 542, and a pin 541, for example. The lid may also include an interstitial opening 516 for communicating atmospheric pressure, for example, with an interstitial space between the cavity and liner, wherein the interstitial opening is closed by a breakable member 514.

The lid may also include a plurality of ports 532, each configured to communicate with a suction instrument, through which fluid is drawn into the fluid collection container. Each port may include a tethered cap 132b. The lid may include a shelf 1510 located between the interior opening of the plurality of ports and the opening communicating with the vacuum source to divert collected fluids away from the vacuum source. The shelf may be shaped to direct entering fluid toward the liner walls and away from the shut off valve. The lid may also include a screen 1520 surrounding the opening to the evacuation opening. The screen may be shaped to prevent solids collected in the fluid from exiting the collection container during disposal. The lid may also include additional features illustrated in FIGS. 53-55.

Among other attachment mechanisms and methods, the liner may be attached to the lid via hot melt, for example at ridge 1530. Prior to use, the liner may also include a breakable band maintaining the liner in a collapsed position against the lid.

Instead of in the lid, a vacuum connection can be provided for the back-up container, for example, as a port 26a on the side of liquid collection system 10, as shown in FIG. 11(a). In this variation, the communication between the suction source and the back up storage container 26 bypasses the disposable lid 31, allowing the back up storage container 26 to directly connect to the vacuum source. Port 26a may be capped or may include a valve, and may be configured to accept tubing or other connecting devices. Bracket 18, which is configured to hold the back up storage container 26, in this exemplary implementation, may also be configured to control the opening/closing of port/valve 26a.

In addition to a separate vacuum port 34 or 26a, one of the plurality of ports 32 may provide communication with a back-up storage container 26. This enables the back-up container to be further used as a trap or specimen collection container.

Further variations of liquid collection containers, housings, and disposal devices, including additional variations of back-up storage containers and specimen collection containers are described in U.S. patent application Ser. No. 12/076, 842, filed Mar. 24, 2008, titled FLUID COLLECTION AND DISPOSAL SYSTEM HAVING INTERCHANGEABLE COLLECTION AND OTHER FEATURES AND METHODS RELATING THERETO, the entire contents of which are incorporated herein by reference.

The back-up storage container may be configured to require a manual connection before use. Alternatively, the back-up storage may be configured to automatically collect overflow liquid from the liquid collection bag once the liquid collection bag has reached its capacity. This automatic arrangement allows the back-up storage container to operate as an overflow canister rather than an independent canister, as described above. The back-up storage container 20 may also be configured to be attached to an independent suction source. Although a back-up storage container without a disposable bag is shown, other embodiments may incorporate a disposable liquid collection bag similar to the bag 30 used inside the cavity 35 of device 10.

FIGS. 15-19 illustrate another exemplary variation of a collection bag 130, according to one aspect of the present invention. This variation is different from the previous implementations shown in FIGS. 1 and 9-12, in that it includes a removable hose junction 134 and a safety valve 142, 144 that operates in connection with the hose junction 134. As shown in FIG. 15, the collection bag 130 includes a lid 131 and a liner 135 attached to the lid 131 to form a substantially sealed interior space therebetween. The liner 135 is substantially similar to the liner 35 of the variation described above and, therefore, a detailed description thereof is omitted herein.

As shown in FIGS. 15 and 16, the lid 131 includes a hose junction 134 removably engageable with a slot 136, located at the top of the lid 131. The hose junction 134 may include a latch 137 having a hook portion configured to releasably engage a corresponding indentation 138 formed inside the slot 136. When the hose junction 134 is pushed into the slot 136, the hook portion of the latch 137 engages the indentation 138, shown in FIG. 19, thereby securely attaching the hose junction 134 onto the lid 131. The hook portion may be sufficiently flexible to allow slight deflection when engaging the indentation 138. To remove the hose junction 134, the latch 137 may be depressed, for example, so as to release the hook portion from the indentation 138. Of course, other conventional methods of removably securing the hose junction 134 to the lid 131 may be employed. The lid 131 may also include a hand grip 133 to facilitate handling of the collection bag 130, as shown in FIG. 17.

Figure 18:
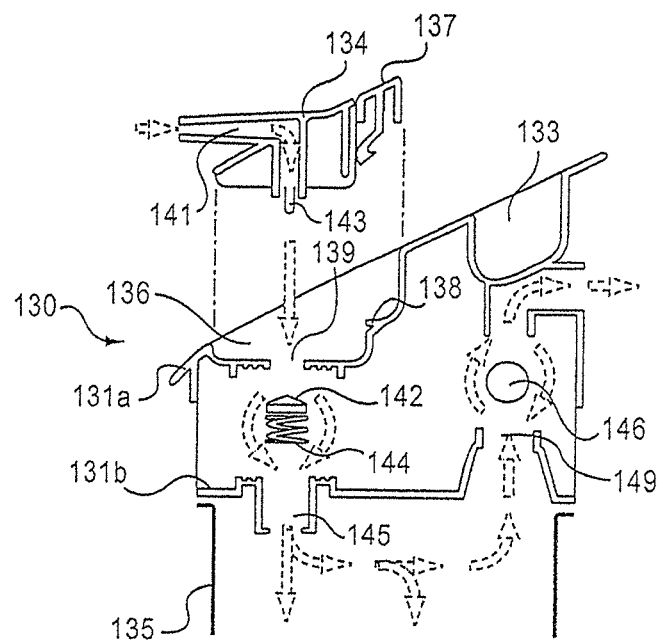
FIGS. 18 and 19 are cross-sectional views of the liquid collection bag shown in FIGS. 15 and 16, respectively.
Figure 19:
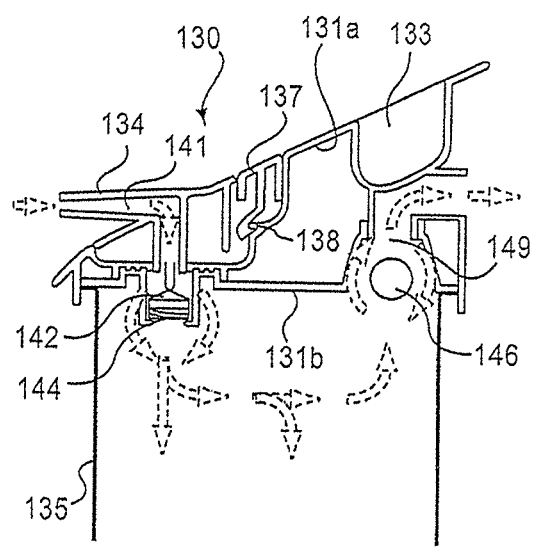

The hose junction 134 carries one or more collection ports 132, each configured to mate with one or more suction instruments or other devices (interchangeably referred to herein as "suction instruments") by way of suction tubings for the purpose of drawing liquid into the collection bag 130. Because the hose junction 134 provides a plurality of collection ports 132, a single collection bag 130 may be used to collect liquid simultaneously from multiple suction instruments. As best shown in FIGS. 18 and 19, the hose junction 134 defines one or more fluid passageways 141 via which liquid is transported from the individual (or multiple) suction instruments to the interior space of the collection bag 130. Thus, the hose junction 134 may function as an interface between the collection bag 130 and the suction instruments and tubings used to collect liquid in the collection bag 130. In addition, the hose junction 134 may include suitable valves (e.g., duckbill valves, check valves, spring loaded plungers) to prevent, or at least minimize, liquid dripping while the suction instruments and tubings are disconnected from the collection bag 130 and disposed of in a suitable disposal container (e.g., a red bag). Thus, the hose junction 134 may reduce the risk of the clinicians' exposure to potentially hazardous materials.

Each of the collection ports 132 may be covered with a flap 132a, which closes the respective collection port 132 when not in use. The flaps 132a may be spring-loaded or otherwise biased such that, when the suction devices and tubings are disconnected from the collection ports 132, the flaps 132a may automatically close the collection ports 132. The flaps 132a may include conventional sealing members so as to define a substantially fluid-tight seal when the flap 132a covers its respective collection port 132. Alternatively, conventional caps or plugs may be frictionally positioned relative to the open ends of the collection ports 132. For example, as shown in FIG. 22(a), the collection ports 132 may include a tethered cap 132b. Alternatively, flaps 132a may be biased to remain in an open position until an operator manually closes them, relative to the collection ports 132. Alternatively still, collection ports 132 may be closed by other devices, such as plugs that are sized and configured to frictionally engage the respective ports 132, in which case, the plugs may be tethered to any portion of the lid 131 (e.g. via a resilient, integrally-molded connector).

The hose junction 134 may enable an easier, cleaner, and faster disposal process since various suction instruments and tubings can be disconnected at once by removing the hose junction 134. These instruments and tubings then can be disposed of with, and while connected to, the hose junction 134. That is, multiple instruments may be connected in parallel to one another and to the hose junction 134, such that each instrument is connected to the hose junction 134 with its own tubing. Detaching the hose junction 134 from the lid 131 then allows for all of the attached instruments (and their individual connection tubes) to be disposed of together without individually detaching each medical instrument from the hose junction 134, such as would be required with conventional suction/irrigation devices. Because the hose junction 134 and the lid 131 may include a non-drip or low-drip valve 142, 144 (as described in greater detail below), such an arrangement minimizes the risk of drippage occurring when the hose junction is disengaged and/or disassembled following a medical procedure.

The lid 131 may also include a non-drip valve 142, 144 to prevent any dripping or splashing of liquid from the interior space of the collection bag 130 when the hose junction 134 is removed from the lid 131. For example, in the exemplary variation shown in FIG. 18, the lid 131 may include two separate components: an upper lid 131a and a lower lid 131b. As shown in FIG. 18, the upper lid 131a defines an inlet opening 139 located at the bottom of the slot 136. The opening 139 is configured to communicate with the individual fluid passageways 141 of the collection ports 132 provided in the hose junction 134. In an alternative arrangement, the inlet opening 139' may be formed on a side surface of the slot 136, as shown in FIG. 17. To facilitate a fluid-tight connection between the fluid passageways 141 and the inlet opening 139, 139', at least one of the fluid passageways 141 and the inlet opening 139, 139' may include a suitable sealing member, such as a sealing ring to provide a sealing fit between the hose junction 134 and the upper lid 131a.

The lower lid 131b defines a valve housing 145 configured to receive the valve 142, 144. The housing 145 defines an opening (e.g., located at its bottom end), which extends into and is open to the interior space of the collection bag 130. The valve 142, 144 may be interposed between the upper lid 131a and the lower lid 131b. The valve 142, 144 may be in the form of a spring-loaded or otherwise suitably biased plunger. The spring 144 may be seated in the housing 145 and the plunger 142 depressed against the inlet opening 139 to close the opening 139, for example. The hose junction 134 may include a projection 143 such that, when the projection 143 engages the slot 136, the projection 143 displaces the plunger 142, thereby establishing fluid communication via opening 139 between the fluid passageway 141 of the hose junction 134 and the interior space of the collection bag 130. Conversely, when the hose junction 134 is removed from the slot 136, the projection 143 releases the plunger 142, and the plunger 142 returns to its biased position to close opening 139. It should be understood that, instead of the spring-loaded plunger 142, 144, any other suitable valve mechanism may be employed. For example, the positioning of the spring 142 and the plunger 144 may be inverted, and these features placed within the tube junction 134, rather than in the lid 131. Alternatively, a ball or flap may be substituted for the plunger 144. In some exemplary implementations, elastomeric or other self-sealing valves may be used.

The lid 131 may also include an overflow valve 146 positioned in a vacuum passageway 149 defined by the upper lid 131a and the lower lid 131b, as shown in FIG. 19. In an exemplary variation, the overflow valve 146 may comprise a floating check valve. As the liquid level in the collection bag 130 reaches the elevational position of the valve 146, the valve 146 rises to close the vacuum passageway 149 thereby preventing the liquid from flowing into the vacuum pump 44. In this manner, the overflow valve 146 may form part of an auto shut-off feature that prevents filling of the bag 130 beyond its capacity or beyond reasonable safety limits. Although FIG. 19 depicts the elevational position of the overflow valve 146 as being vertically above the elevational position of the valve 142, 144, one of ordinary skill in the art will appreciate that the overflow valve 146 may be placed at an elevational position below that of the valve 142, 144.

Figure 20:
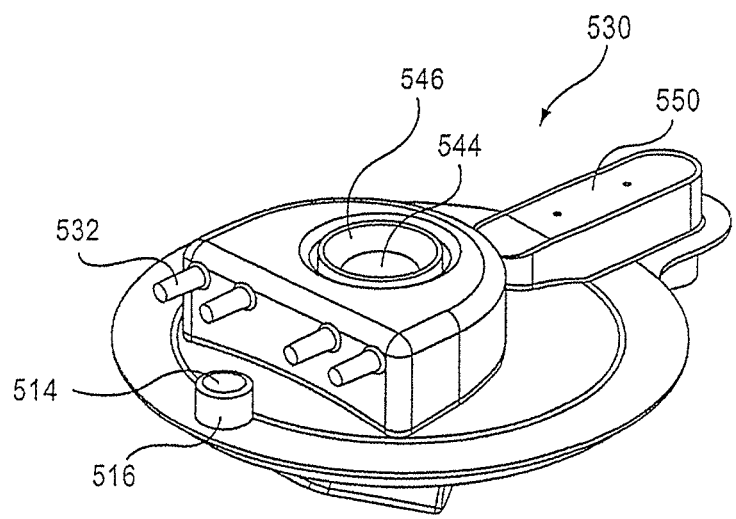
FIGS. 20 and 21 are perspective views of a lid for a liquid collection bag, in accordance with aspects of the present invention.
Figure 21:
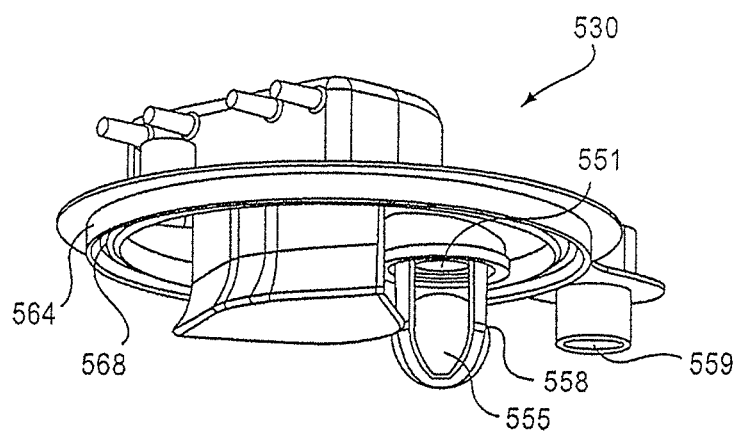
Figure 22:
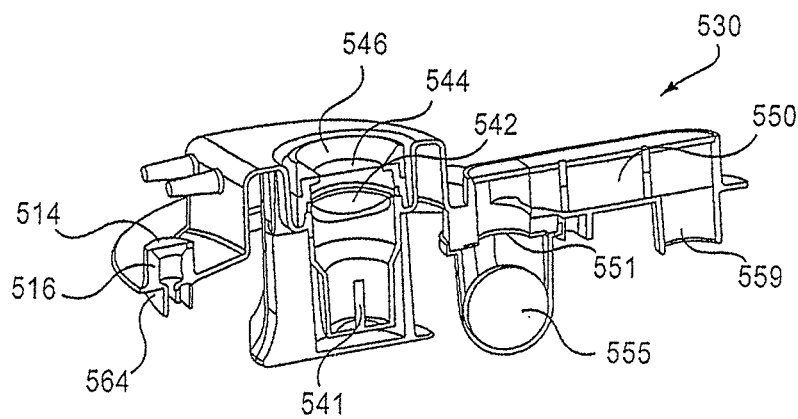
FIG. 22 is a perspective cut-away view of the lid shown in FIGS. 20 and 21.
Figure 22A:
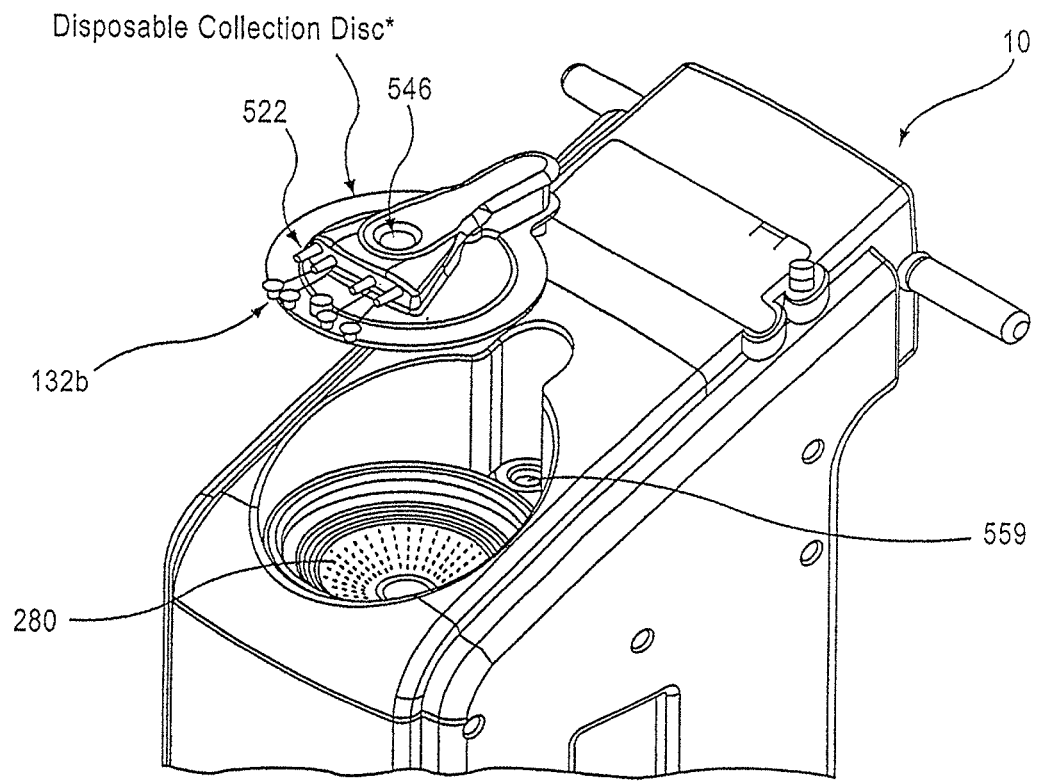
FIG. 22a is an illustration of a lid and system in accordance with aspects of the present invention.

According to other exemplary aspects of the present invention, the lid 530 may be integrally formed (e.g., molded) as a single piece, as shown in FIGS. 20-22. Forming the lid 530 as a single piece may lower the manufacturing cost and also simplify the fluid collection process by eliminating the need for a removable hose junction 134, described above with reference to FIGS. 15-19.

The lid 530 illustrated in FIGS. 20-22 differs from the lids 31, 131 depicted in FIGS. 9-12 and 15-19, in that, among other things, it includes a breakable closure member 544 (e.g., a foil, plastic film, rubber) for closing an evacuation port 546 of the lid 530, as shown in FIG. 22. FIG. 22(a) shows a variation of the lid for a liquid collection bag in which the exterior of the passageway providing communication between the liquid collection bag 30 and the suction source 559 is configured as a gripping member 501 on the exterior of the disposable lid. This gripping member 501 provides an area removed from the collection ports 532 and from the disposal port 546 by which a user can grip the disposable lid to attach and remove the disposable lid. This gripping member 501 both enhances the ease of installation and removal of the liquid collection bag, while allowing the user to avoid contact with the port areas through which waste material is collected and evacuated.

Unlike the collection ports 32 shown in FIG. 9-12, and the inlet openings 139, 139' of the embodiments shown in 15-19, which are used to both collect and remove liquid for the collection bag 30, 130, the evacuation port 546 of FIGS. 20-22 is not used during liquid collection operation and remains sealed by the closure member 544 until the collection bag is full and/or otherwise needs to be emptied. Structural features of the evacuation port 546 and operational characteristics associated with a disposal station (herein referred to interchangeably as a "docking station") will be described in more detail with reference to FIGS. 48-52. Although one variation described herein refers to a breakable closure member, such as foil, other sealing mechanisms may be used in place thereof. For example, a sliding or pivoting door may be configured to rest over the evacuation port 546 when access thereto is not required, and further configured to move away therefrom, either manually or automatedly, when access to the evacuation port 546 is desired.

The lid 530 of FIGS. 20-22 also differs from the lids 30, 130 of FIGS. 9-12 and 15-19, in that it forms an interstitial opening 516 in the lid 530 for supplying a source of suction pressure (e.g., see the eductor 350 shown in FIGS. 31, 32, and 42) to a space between the rigid receptacle defining a cavity and the collection bag during an evacuation process. The source of suction pressure may be used to equalize the pressures inside and outside of the collection bag during an evacuation process, so that the collection bag may substantially maintain its normal shape during that process. The interstitial opening 516, like the evacuation port 546, is closed off during the liquid collection process by a breakable closure member 514. Structural features of the opening 516 and operational characteristics associated with the disposal station will be described in more detail with reference to FIGS. 48-52.

In the suction pressure shown in FIG. 20-22, the lid 530 defines a vacuum passageway 550 having a U-shaped configuration. The first end 551 communicates with an interior space of the collection bag, and the second end 559 communicates with a vacuum source. Near the first end 551 of the vacuum passageway 550, in one exemplary suction pressure the lid 530 includes an overflow valve having a floating ball 555 housed in a cage-like structure 558. Other exemplary lids 530 may include a hydrophilic valve, such as a porous plastic valve (PPV), as shown and described in connection with FIGS. 27-33. When the liquid level in the collection bag reaches the elevational position of the floating ball 555, the ball 555 rises along the longitudinal axis of the cage-like structure 558, thereby closing the first end 551 of the vacuum passageway 550. The operational characteristics of the floating ball 555 are substantially similar to those of the overflow valve 146 of FIGS. 18 and 19 and, therefore, a detailed description thereof is omitted herein.

Figure 23:
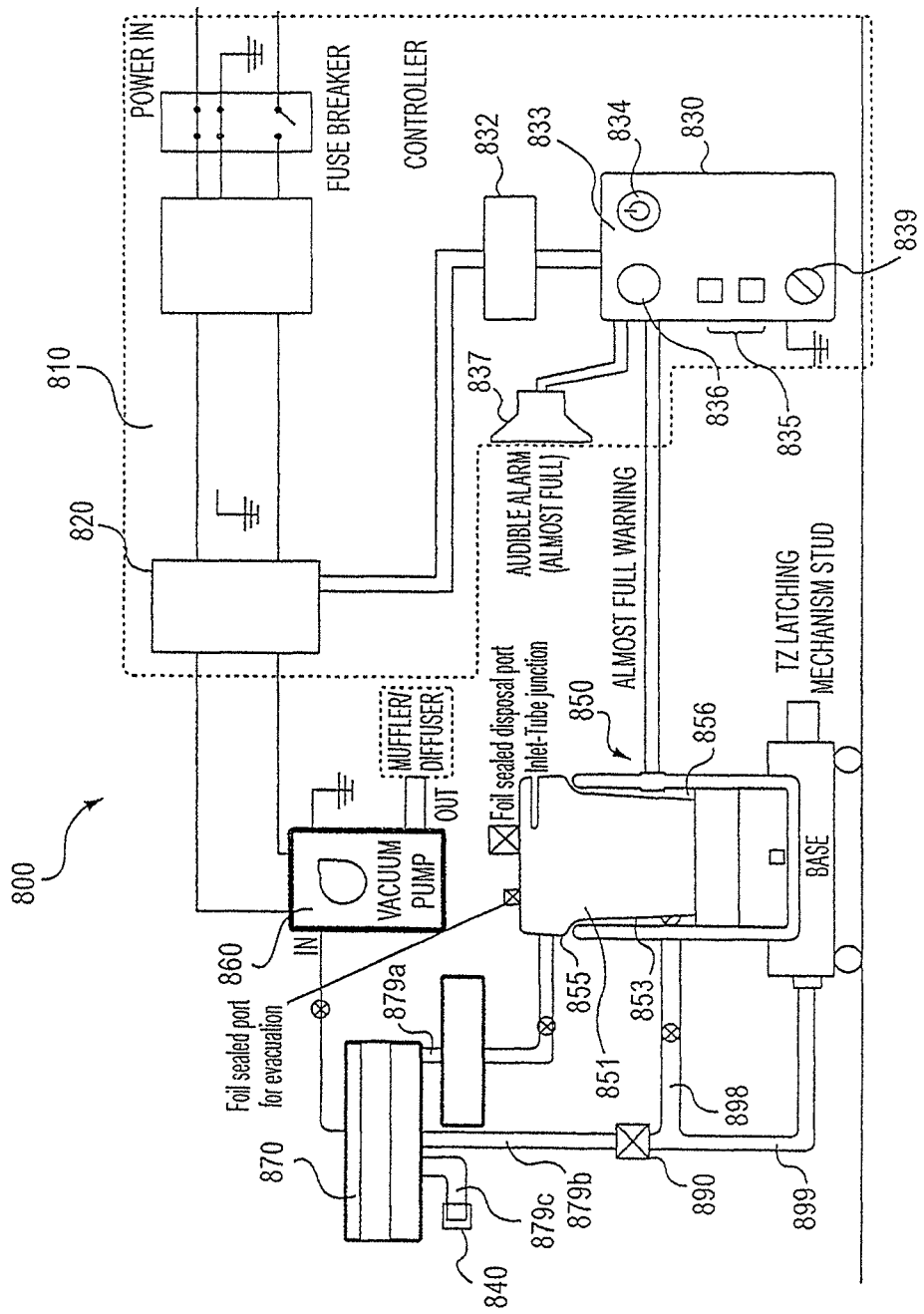
FIG. 23 is a block diagram of one variation of a liquid collection system illustrating various components and their operational characteristics thereof, in accordance with aspects of the present invention.

FIG. 23 shows a block diagram of a liquid collection system 800, illustrating various components and corresponding operational characteristics, according to certain exemplary aspects of the present invention. Many features applicable to the illustrated system 800 have been already described in detail above. The liquid collection system 800 includes a controller 810 for controlling operation of various components of the system 800. For example, the controller 810 may include a motor controller 820 configured to control the vacuum pump 860. The motor controller 820 may be coupled to an interface board 830 configured to display the status of the system 800 and/or provide an input signal to the motor controller 820 for controlling various components of the system 800. For example, the interface board 830 may include a selection button 834 for controlling the power supply to the system 800 and a vacuum regulator 836 (e.g., variable control knob) for regulating the vacuum level created by the vacuum pump 860. The interface board 830 may also include one or more visual or audible indicators 833, 835, 837 for providing various information relating to operational characteristics and/or status of the system 800. For example, the one or more indicators may include a vacuum level indicator 833 (e.g., a Light Emitting Diode "LED" light bar), light indicators 835 for indicating whether the filter needs to be replaced and/or whether the storage bag is almost full. Audible alarms 837 may also provide audio warnings or indicators of the status of the system 800. The audio warnings or indications provided by the audible alarms 837 may be redundant to, or independent from, those provided by the visual indicators 833, 835. The interface board 830 may also include a switch 839 (e.g., toggle key) for disabling the audible alarms 837. The interface board 830 may be powered by an isolated power supply 832 (e.g., a battery).

The system 800 may include a filter unit 870 disposed between the vacuum pump 860 and various components requiring connection to the vacuum pump 860. The filter unit 870 may be substantially similar to that described above with reference to FIGS. 7 and 8. As mentioned above, the filter unit 870 may include a filter made of a hydrophobic material, so as to function as a safety shutoff valve. For example, an overflow shutoff valve 851 in the collection bag 855 may malfunction when the liquid collection bag 855 is full, causing the liquid collected in the bag 855 to flow into the filter unit 870 through the first suction line 879a. Also, the liquid collection bag 855 may be defective, causing leakage of liquid collected therein to flow into the cavity 856. The leaked liquid in the cavity 856 may flow into the filter unit 870 via the interstitial line 898, the base vacuum line 899, and the second suction line 879b, for example. When the liquid enters the filter unit 870 and makes contact with the filter, the hydrophobic material blocks the pores of the filter, for example using surface tension, and shuts off the filter unit 870, thereby preventing the liquid from flowing to the vacuum pump 860.

Figure 24:
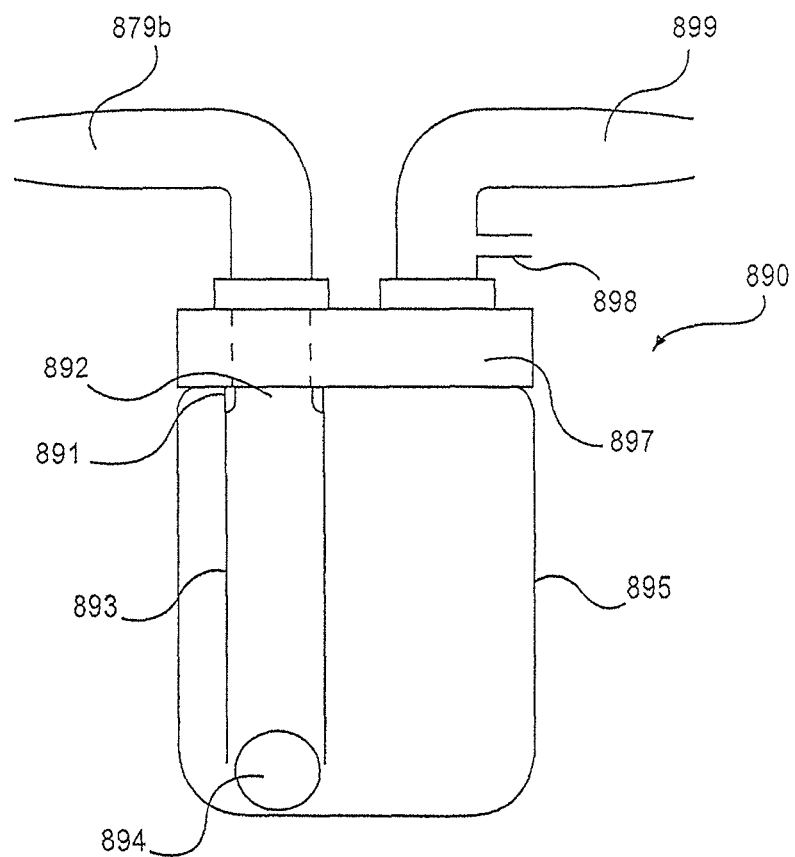
FIGS. 24 and 24(a) are a schematic illustrations of exemplary variations of a fluid trap, in accordance with aspects of the present invention
Figure 24A:
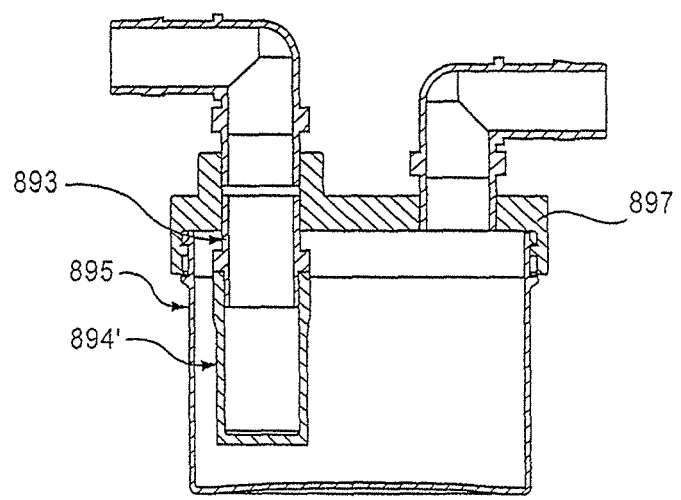

The system 800 may also include one or more additional safety features. For example, the system 800 may include an optional fluid trap 890 disposed between the filter unit 870 and the interstitial and base lines 898, 899 shown in FIG. 23. The system may also include a fluid trap or a vacuum check valve located between the vacuum pump 860 and the HEPA housing 870. The optional fluid trap 890 may operate under a similar principle to that of the overflow valves 146, 555 disposed inside the liquid collection bag. For example, FIGS. 24 and 24(a) illustrate exemplary variations of a fluid trap 890, according to exemplary aspects of the present invention. The fluid trap 890 may include a container 895 defining an internal volume in fluid communication with one or more inlets (e.g., the interstitial and base lines 898, 899 connected to the cavity 856) and an outlet (e.g., the second suction line 879b leading to the filter unit 870). The container 895 may include a removable cap 897, to which the one or more inlets and the outlet may be secured. Although the interstitial line 898 is shown in the figure branch out from the base line 899, the interstitial line 898 may alternately be separately and independently connected to the container 895. The container 895 may include a conduit 893 (e.g., a tube) extending from the outlet 879b into the container 895, with a PPV or other hydrophobic valve 894' or floating ball 894 (e.g., a polypropylene ball) being attached to or otherwise interacting with the conduit 893. The floating ball 894 rises inside the conduit 893 as the liquid level inside the container 895 rises. When the liquid level rises above the top of the conduit 893, the floating ball 894 presses against the opening 892 defined by the top of the conduit 893, thereby shutting off the outlet 879b leading to the filter unit 870. To ensure a tight seal between the floating ball 894 and the opening 892, an O-ring 891 may be provided in the opening 892. The PPV or other hydrophilic valve comprises a hydrophilic material that blocks the pores of the material, for example using surface tension, and thereby prevents liquid from flowing past the material. A similar valve is shown as element 238 and described in connection with FIGS. 27-33. By way of example only, the container 895 may have a volume of about 16 oz.

The system 800 may also include an emergency backup tube 879c, which is normally closed by an end cap or valve. The backup tube 879c may be configured to connect to an alternate source of suction force 840 (e.g., a wall vacuum), such that, when the vacuum pump 860 becomes inoperable or otherwise unavailable, for example, or when the filter unit 870 shuts off, the system 800 can continue to operate with the alternate source of suction force, without interrupting an on-going medical procedure. In addition, the backup tube 879c may function as a vacuum supply line for a backup storage container. For example, when the collection bag 855 becomes full or temporarily inoperable during a liquid collection process, the backup tube 879c may be connected to a backup storage container to supply suction force to the storage container, so that the storage container may function as a suction canister to temporarily store the liquid being collecting during the liquid collection process.

Figure 25:
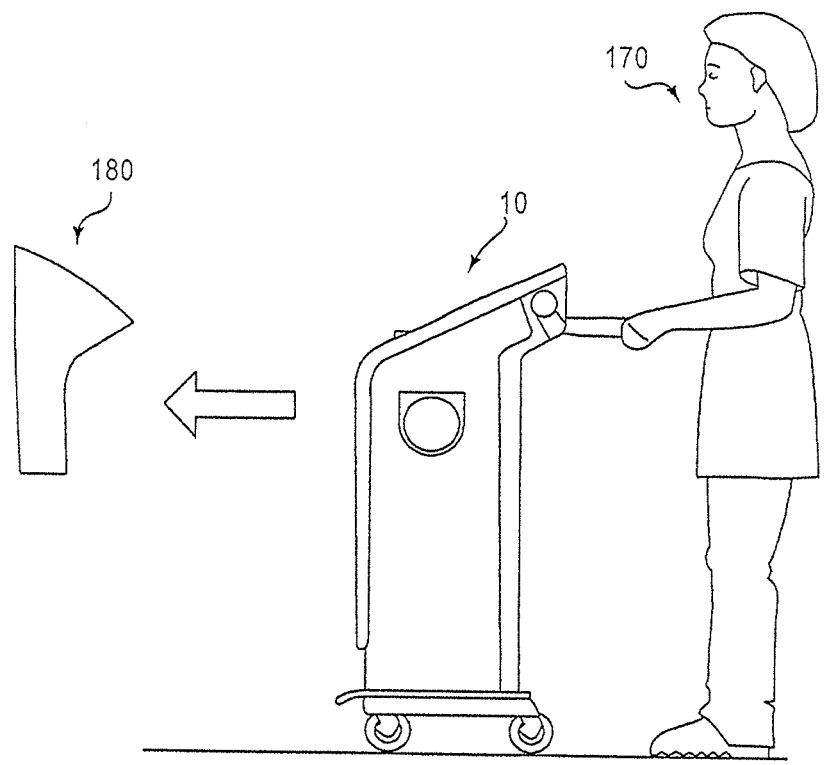
FIG. 25 is a schematic illustration of a liquid disposal process, in accordance with aspects of the present invention.

Once the collection bag 30, 130 is full or otherwise needs to be emptied, the portable liquid collection system 10 may be transported to a disposal station by, for example a clinician 170 to evacuate the collected liquid from the collection bag 30, 130, as shown in FIG. 25. Although evacuation of the collection bag 30, 130 is not necessary for disposal thereof (e.g., a filled collection bag 30, 130 may be disposed of with liquid still present within the interior space thereof), one aspect of the present invention allows for the evacuation of the collection bag 30, 130 to reduce the volume of red-bag waste produced by disposal thereof.

In some exemplary variations, the disposal station may comprise a docking station 180 having a fluid connector configured to automatically (or manually) connect to the discharge port 38 (for the implementation shown in FIG. 1), the inlet port 139, 139' (for the variations shown in FIGS. 15-19), or the evacuation port 546 (for the embodiment shown in FIGS. 20-22) of the collection bag 30, 130. For the variations shown in FIGS. 15-19, prior to engaging the system 10 into the docking station 180, the hose junction 134 may be removed. The docking station 180 may include a suitable indicator 185 for indicating that the collection system 10 is properly engaged and/or the evacuation process is being performed.

Figure 26:
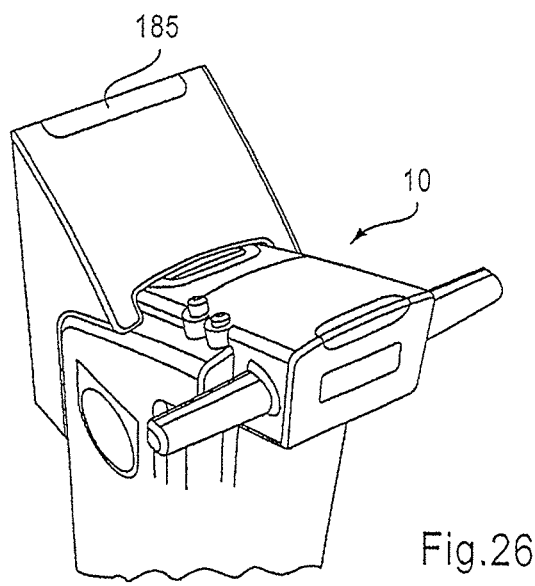
FIG. 26 is a perspective view of the liquid collection system of FIG. 1, engaged with a liquid disposal station, in accordance with aspects of the present invention.
Figure 26A:
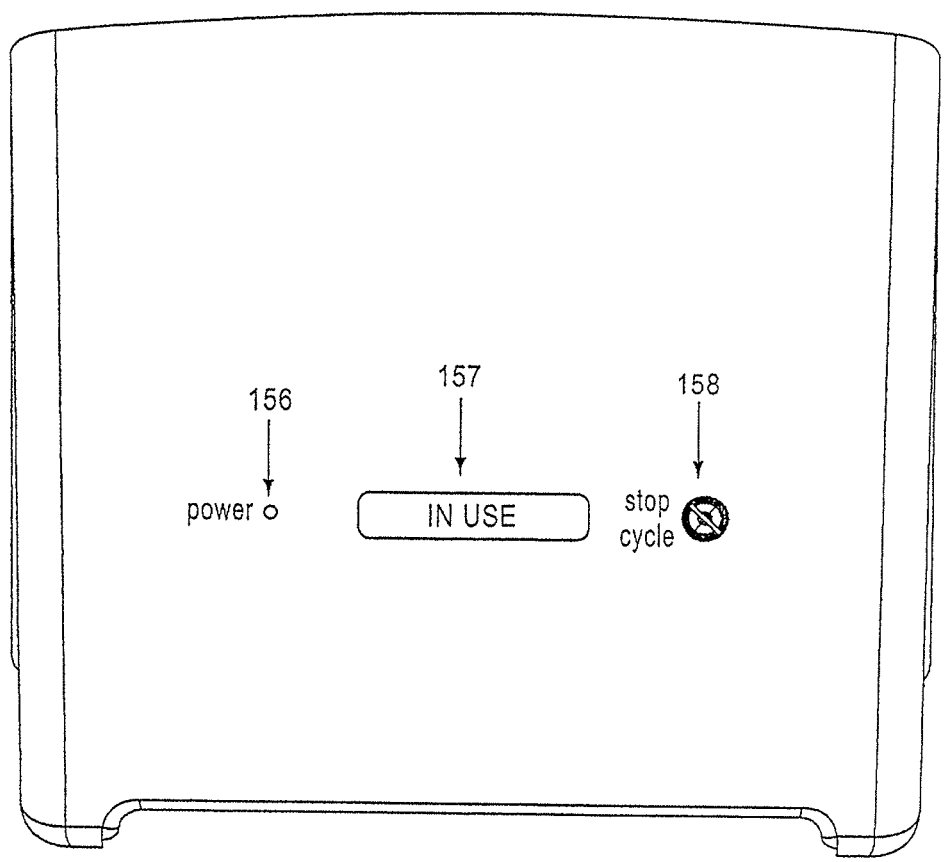
FIG. 26(a) is a perspective view of an exemplary user interface for a liquid disposal station, in accordance with aspects of the present invention.

FIG. 26(a) shows an interface board for a disposal station, in accordance with aspects of the present invention. The interface board may include a light 156 indicating a connection to a power source and a visual indication 157 that the disposal station is in use. The interface board may also include a switch 158 that allows termination of the evacuation cycle. The button 158 may stop the cycle completely or only temporarily.

To evacuate the collected liquid from the collection bag 30, 130, in some exemplary embodiments, the docking station 180 may utilize an eductor of the type described in U.S. Patent Application Publication No. 2005/0183780, entitled "Method and Apparatus for the Disposal of Waste Fluids" and published on Aug. 25, 2005, the entire disclosure of which is incorporated herein by reference. Alternatively or additionally, the disposal station may include a movable connector (not shown) that can be manually connected to the collection bag 30, 130 to evacuate the collected liquid therefrom.

FIGS. 27-33 illustrate another exemplary embodiment of a liquid collection and disposal system. As shown in FIG. 27, the system includes a liquid collection bag 230 and a rigid container 215 configured to receive the collection bag 230. The collection bag 230 may include a lid 231 and a collapsible liner 235 attached to the inner surface of the lid 231 to form a substantially sealed interior space therebetween. When the collection bag 230 is placed on the top of the rigid container 215, the lid 231 may substantially seal the opening of the container 215. As shown in FIG. 27, the collection bag 230 may include a suction conduit 233 for connecting the interior space of the collection bag 230 to a suitable suction source (e.g., vacuum pump 44 shown in FIG. 1). The suction conduit 233 may be arranged such that, when the collection bag 230 is placed on the container 215, the suction conduit 233 automatically connects to the suction source, although the suction source may be configured to be manually connected to the suction conduit 215 by the operator.

The collection bag 230 may include a suction shutoff device 238 positioned at one end of the suction conduit 233. As will be described in more detail, the shutoff device 238 may close the suction conduit 233 when the liquid level inside the collection bag 235 reaches a predetermined level, so as to prevent the collected liquid from flowing into the suction source. In one exemplary embodiment, the shutoff device 238 may comprise a filter that prevents liquid from passing therethrough, which may be, for example, similar to the device 894' shown in FIG. 24(a). The filter may be positioned at a proximal end of the suction conduit 233, located inside the collection bag 230, such that, when the liquid level in the collection bag 230 rises above the filter and submerges the filter, the filter may close the suction conduit 233, thereby shutting off the supply of suction force and terminating the liquid collection process. Alternatively or additionally, the shutoff device 238 may include a hydrophilic material, which may swell and seal the suction conduit 233 upon contact with liquid. In certain implementations, the shutoff device may comprise a buoyant article (which may be coated or otherwise covered with a hydrophobic material) disposed within a cage extending from the lid, such that the buoyant article may close off the suction conduit when the level of the liquid rises beyond an acceptable elevational position.

The lid 231 may define an access port 220 normally closed by a flexible valve 226, such as an elastic slit valve. As will be described in more detail later, the access port 220 may be configured to receive a hose junction 240 and an evacuation connector 340. When the hose junction 240 or the evacuation connector 340 is inserted into the access port 220, the flexible valve 226 may be deflected to open the access port 220. The access port 220 may also include an actuation rod or pin 224 to open a valve associated with the hose junction 240 and/or the evacuation connector 340, which will also be described in more detail herein.

The rigid container 215 may have an elongate tubular shape, similar to the receptacle 80 shown in FIG. 4. The rigid container 215 may constitute the cavity 15 of the liquid collection system 10 described above. The container 215 may include a piston 280 (much like a syringe) slidably positioned inside the container 215. The piston 280 may include one or more sealing members, such as O-rings 283 attached to an outer peripheral edge of the piston 280. Thus, the piston 280 may separate the internal space of the container 215 into an upper space 281 and a lower space 289. The piston 280 may also include a piston scraper 285 to prevent the liner 235 from being pinched between the inner wall of the container 215 and the piston 280 during a piston movement. The O-rings 283 and the piston scraper 285 may be coated with a suitable material (e.g., parylene) to enhance lubricity and/or durability.

The piston 280 may include a through-hole 284 in the middle portion, which enables a vacuum communication between the upper space 281 and the lower space 289. The through-hole 284 thus supplies a vacuum force into the upper space 281, which may counterbalance vacuum force applied inside the interior space of the collection bag 230 to prevent collapse of the liner 235 during a liquid collection stage. The piston 280 may include a check valve 286 positioned inside the through-hole 284. The check valve 286 is biased against an opening of the through-hole 284 by a spring 288 to normally close the through-hole 284. In some exemplary variations, the check valve 286 may be disposed in a modular check valve insert, which may be inserted into the through-hole 284.

Figure 29A:
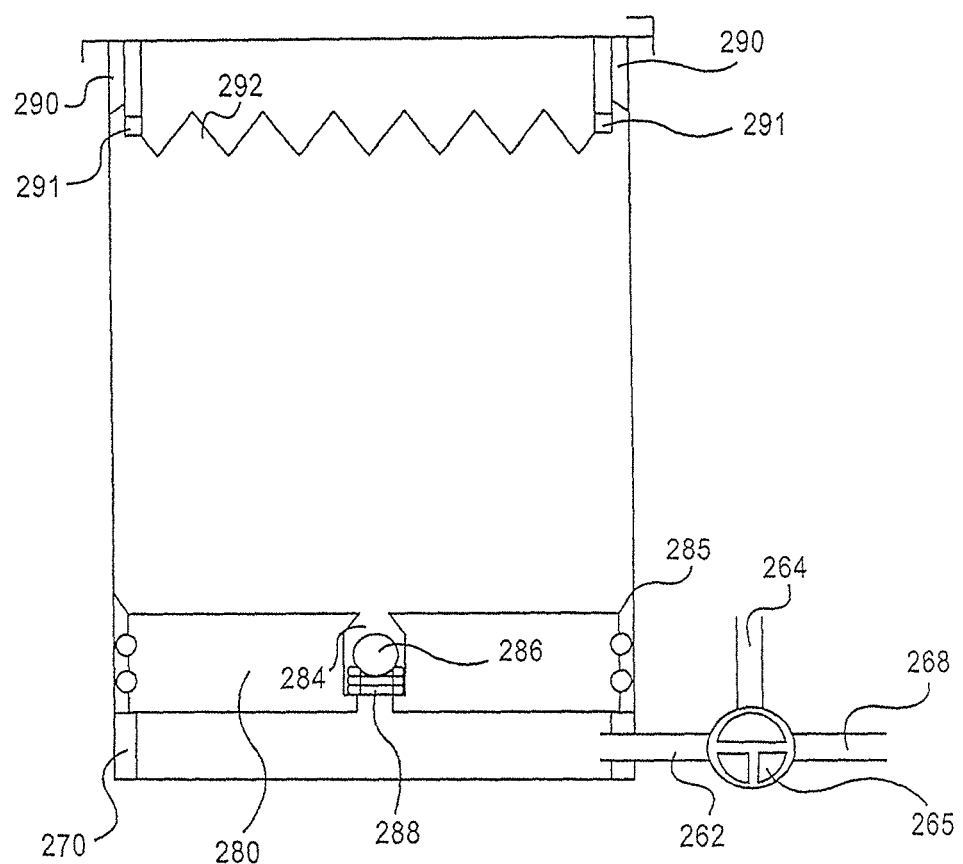

The container 215 may also include a stopper 290 that interacts with the piston scraper 285 near the top of the container 215, as shown in FIG. 29(a). In addition to stopper 290, the container may further include a pinch prevention mechanism 291 that prevents the collection bag from being caught between the piston scraper 285 and stopper 290 as the piston moves upward during evacuation of the collection bag. One variation of the pinch prevention mechanism may include a flexible collar 291 located between the inner walls of the container 215. For example, if the container is cylindrical, the flexible collar may include a flexible cylindrically shaped collar. The flexible collar 291 may include grooves 292, as shown in FIG. 29(b), and may comprise a flexible material such as plastic or rubber. As the piston 280 moves up in the container, the flexible collar 291 flexes toward the interior of the container and compressibly pushes the collection bag 235 away from the walls of the container, while closing the grooves therein as shown in FIG. 32(a). This prevents the collection bag from being caught between the piston scraper 285 and the stopper 290, as the bag collapses during disposal.

As shown in FIG. 27, the container 215 may include an optional three-way valve 265 to selectively connect the lower space 289 to either a vacuum source or atmosphere. The container 215 may also be configured without the optional three-way valve, for example when the vacuum source is vented. For example, the three-way valve 265 may have three connections: a first connection 262 communicating with the lower space 289; a second connection 264 communicating with atmosphere; and a third connection 268 communicating with a suction source. The operational characteristics of the three-way valve 265 will be described in detail with reference to FIGS. 28-32. The container 215 may also include a stopper 270 near its bottom, as shown in FIG. 27, to prevent the piston 280 from descending below the level of the first connection 262. Alternately, valve 265 may be eliminated, for example, when reverse venting (to atmosphere) might be accomplished naturally, for example, when the pump (not shown) is turned off.

As shown in FIG. 27, the piston 280 is initially positioned near the top of the container 215 to receive the collection bag 230. After the collection bag 230 is emplaced, in its collapsed state, within the container 215, the hose junction 240 may be inserted into the access port 220, as shown in FIG. 28. The hose junction 240 is similar to the hose junction 134 shown in FIGS. 15, 16, 18, and 19, except that it includes a normally-closed valve 249 (e.g., a duckbill valve, a check valve, a spring-loaded valve, a poppet valve) to open and close its fluid passageway 245. The valve 249 may be opened from its normally-closed position by the actuator pin 224 positioned inside the access port 220. That is, upon insertion into the access port 220, the actuator pin 224 pushes the valve 249 so as to open the passageway 245. The hose junction 240 may be inserted in the access port 220 before the collection bag 230 is placed onto the container 215.

Once the collection bag 230 is placed in the container 215 and the hose junction 240 is securely positioned in the access port 220 of the collection bag 230, the optional three-way valve 265 may be rotated to align the first connection 262 with the third connection 268 to communicate such pressure within the lower space 289. The suction pressure applied to the lower space 289 draws the piston 280 down into the container 215, which in turn draws the liner 235 into the cavity, as shown FIG. 29. In one variation, the interior space of the liner 235 is open to atmosphere (or is under some pressure greater than the suction pressure supplied to the lower space 289), so as to facilitate the downward movement of the piston 280. The suction force applied to the lower space 289 may be greater than the opening pressure of the check valve 286, so as to open the through-hole 284 and evacuate any excess air in the upper space 281, which may enhance the seal between the lid 231 and the container 215.

However, it may be preferred for the check valve 286 to remain in a closed position during downward movement of the piston 280, so as to further enhance the pressure differential between the lower space 289 and the upper space 281, thereby further facilitating the downward movement of the piston 280 within the cavity. The sensitivity of the check valve 286 may be selected in view of the suction pressure supplied to the lower space 289, any suction pressure supplied to the upper space 281 and the atmospheric (or positive) pressure supplied to the interior space of the liner 235. In the selection of the check valve sensitivity, an efficient pressure differential and/or balance on both sides of the piston 280 can be utilized to facilitate downward movement thereof, as described further herein.

Figures 29, 30:
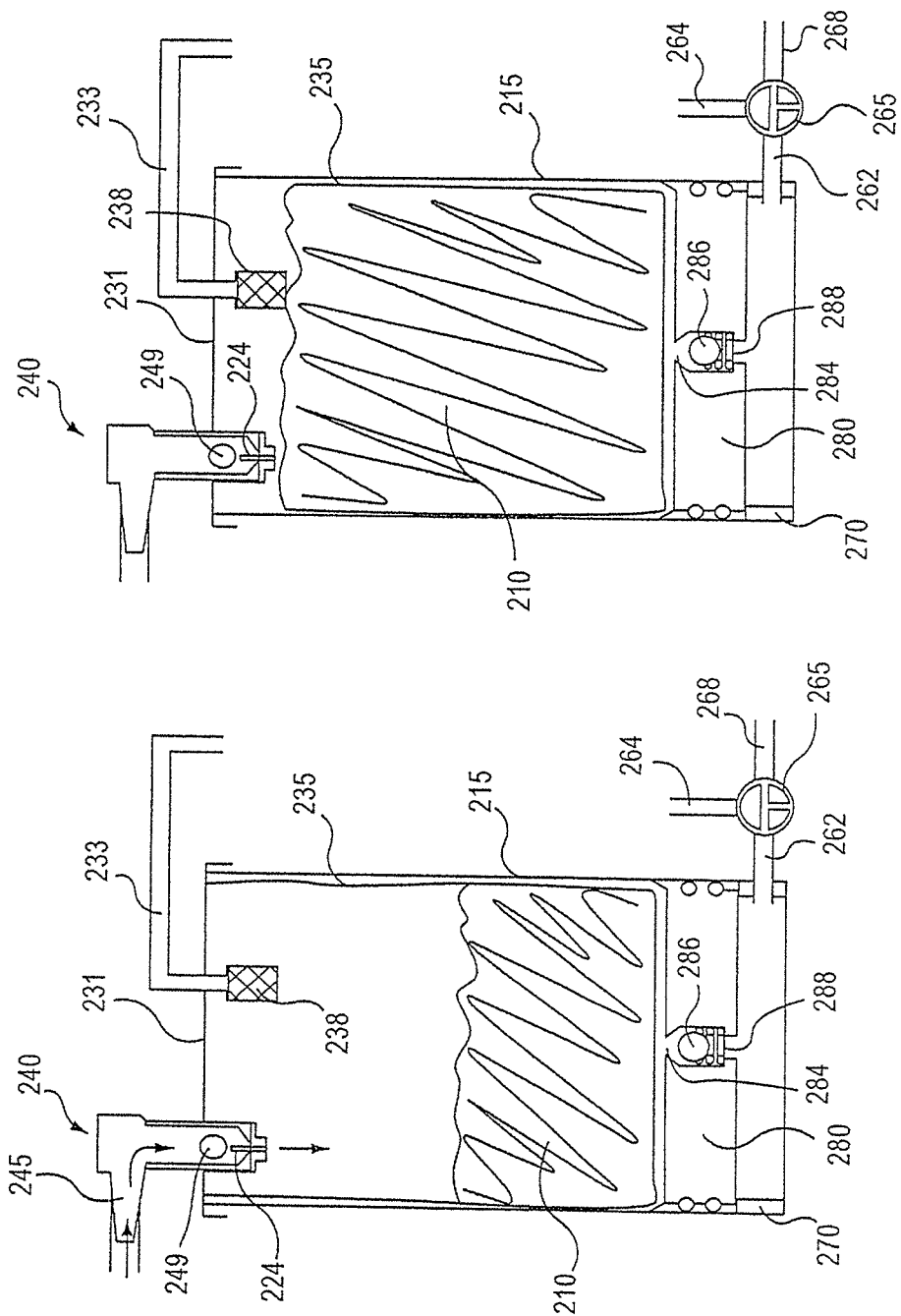

Thereafter, liquid may be drawn into the collection bag 230, as shown in FIG. 29. The liquid collection process is substantially similar to the process described above with reference to FIG. 12 and, therefore, a detailed description thereof is omitted at this point. As mentioned above, during the liquid collection process, the continuously applied suction force in the lower space 289 may cause the check valve 286 to open, so as to communicate the suction pressure with the upper space 281, which may counterbalance the suction force applied inside the interior space of the collection bag 230 to prevent or reduce collapse or deformation of the liner 235 during the liquid collection process.

The liquid collection process may thereafter end because the medical procedure is completed, for example. This action may also end as a result of suction pressure shutoff, which may occur, for example, when the liquid level rises to the level of the shutoff device 238. For example, when the liquid level reaches the level of the shutoff device 238, the shutoff device 238 may automatically shut off the conduit 233 to stop the liquid collection process, as shown in FIG. 30. Should the liquid collection process be continued, a back-up storage container 20, for example, described above with reference to FIGS. 13 and 14 may be used to continue the process.

Figure 31:
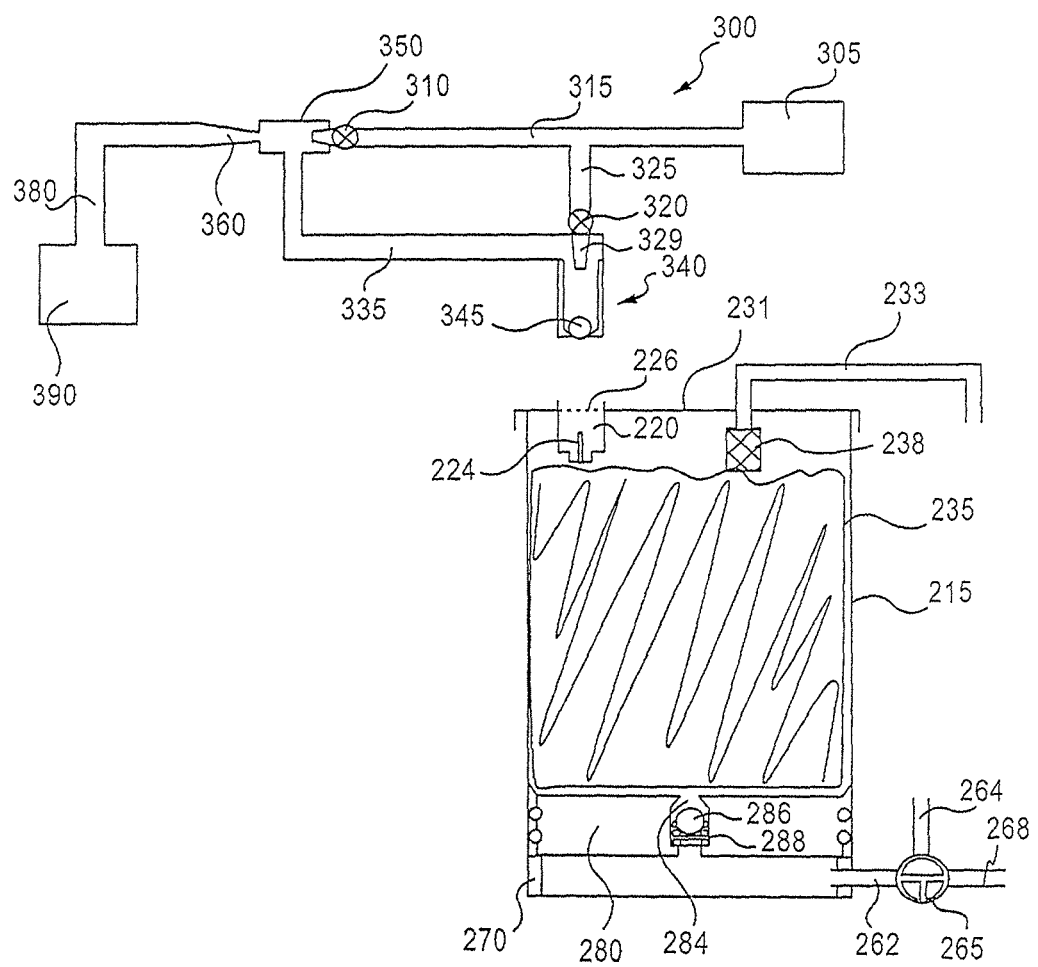

To empty the collection bag 230, the container 215 carrying the collection bag 230 may be transported to a disposal station 300 (e.g., a pump assembly), as shown in FIG. 31. Prior to connecting the collection bag 230 to the disposal station 300, the hose junction 240 carrying one or more medical devices may be removed and placed in a red bag for disposal, for example. The anti-drip valve 249 of the hose junction 240 closes the fluid passageway 245 upon removal from the access port 220 (e.g., the actuator pin 224 no longer holds the valve 249 open). Also, upon removal of the hose junction 240, the flexible valve 226 may return to its original shape to close the access port 220. The closure of the access port 220 may keep the collected liquid in the collection bag 230 for transport to the disposal station. The flexible valve 226 may also provide a wiping function on the hose junction 240 during removal from the access port 220. This wiping function may aid in making the hose junction 240 drip free during its removal and disposal.

As shown in FIG. 31, the disposal station 300 may include an eductor 350 that provides a source of vacuum sufficient to draw the collected liquid out of the collection bag 230. In addition to the eductor 350 depicted in FIG. 31, other vacuum or suction sources may be used to draw the fluid out of the collection bag 230 to the disposal station. For example, a pump such as a rotary pump or piston pump or other suitable device (e.g., a flexible membrane device), may be used to evacuate the contents of the collection bag 230. To connect the collection bag 230 to the disposal station 300, the disposal connector 340 may be inserted into the access port 220 of the collection bag 230 in a similar manner to how the hose junction 240 is inserted into the access port 220. Similar to the hose junction 240, the disposal connector 340 may include a drip-free connector valve 345, which is biased to close the distal end of the disposal connector 340. Inserting the disposal connector 340 may cause the connector valve 345 to open, so as to establish fluid communication between the access port 220 and the eductor 350.

The eductor 350 may be positioned between a source of water or other rinse fluid 305 and a sanitary sewer 390 to create a pumping force sufficient to draw liquid out of the collection bag 230. Rinse fluid may consist of water, another wash fluid (e.g. a detergent or other fluid), or a mixture of water and another wash fluid. As noted above, the term "fluid" may refer to a combination of a liquid medium along with solid particles, gases and/or particulates. As shown in FIG. 31, the eductor 350 may be connected to the source of water 305 and the sewer 390 via a water conduit 315 and a discharge conduit 380, respectively. The water conduit 315 may include a water valve 310, which may be controlled manually or by other control, such as electric switch. In addition, a venturi 360 may be suitably positioned, (e.g., adjacent the eductor 350 in the discharge conduit 380) so as to create a greater pumping force. The disposal connector 340 may be then connected to the eductor 350 via an evacuation conduit 335.

Figure 32:
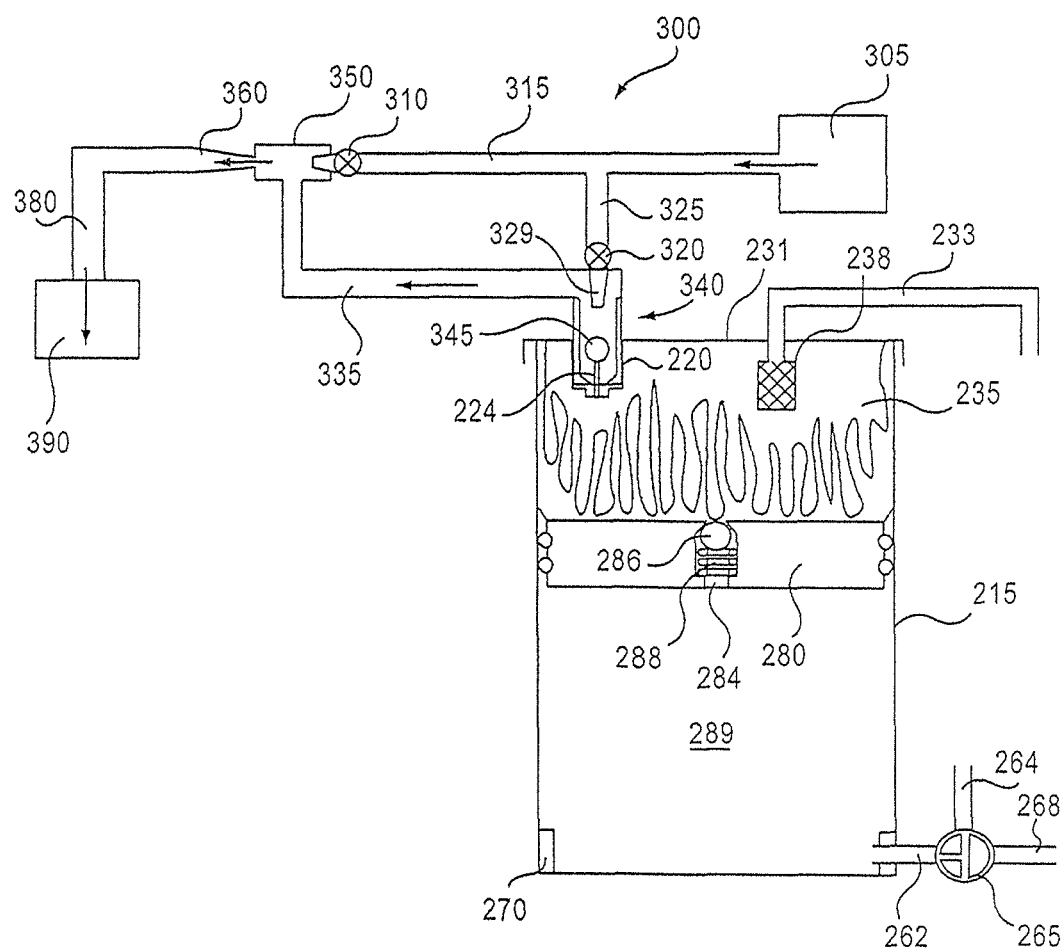
Figure 32A:
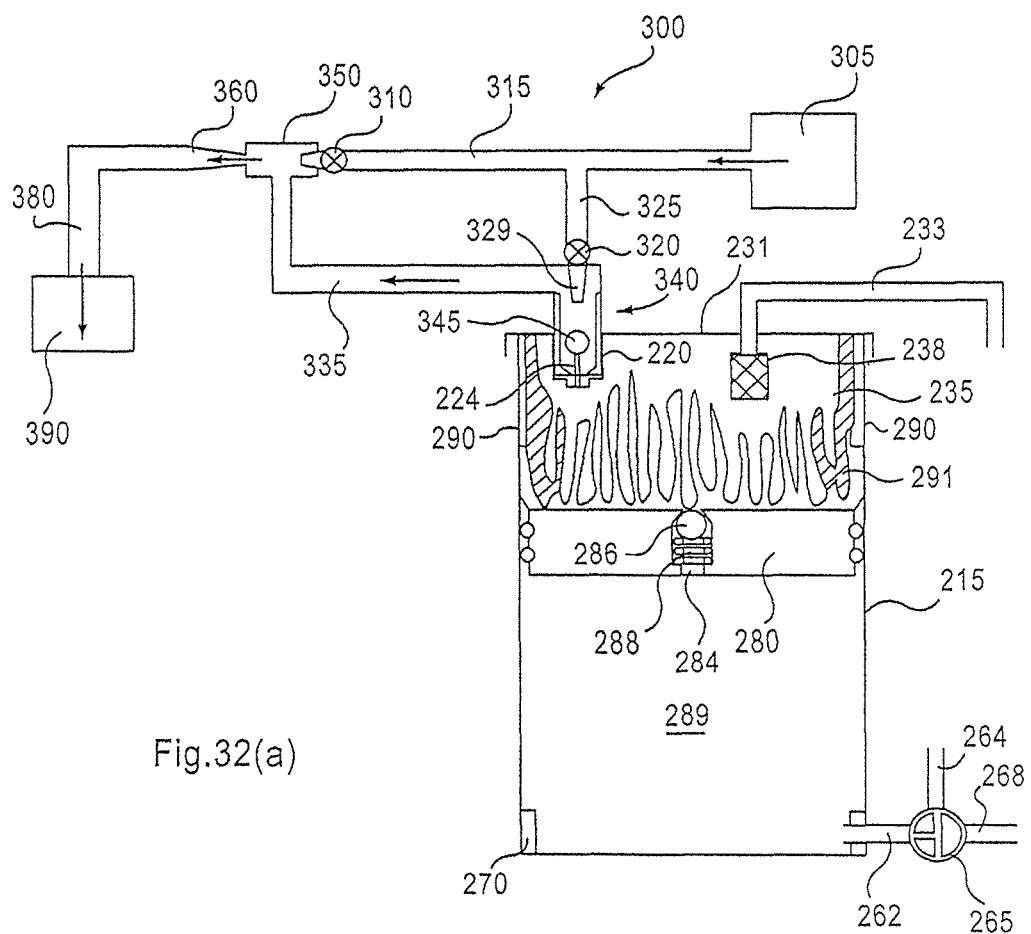

In operation, as shown in FIG. 32, opening the water valve 310 causes the water from the source of water 305 to flow into the eductor 350 to create a pumping force in the eductor 350. This pumping force causes the liner 235 to collapse and then liquid collected in the collection bag 230 to flow into the eductor 350 and then into the sanitary sewer 390 via the discharge conduit 380. To control the collapse geometry of the liner 235 in a manner that does not occlude and prevent the desired discharge liquid flow, check valve 286 may be set in a closed position. The closed position of the check valve 286 prevents air from flowing into the space between the liner 235 and the container 215. Because of the relatively limited air in the space outside of the liner 235, the walls of the liner 235 will not be pulled away from the walls of container 215 and therefore will not close off the passage of liquid within the liner 235. At this stage, the optional three-way valve 265 may be aligned to communicate the lower space 289 with atmosphere via the first and second connections 262, 264, as shown in FIG. 32. This selection allows the pressure inside the lower space 289 to reach atmospheric pressure during the evacuation process, so as not to interfere with the collapse of the liner 235. For example, maintaining the pressure in the lower space 289 at atmospheric pressure allows the piston 280 to rise during the evacuation process, due to a differential pressure between the upper space 281 (which is subject to a suction pressure) and the lower space 289 (which is open to atmosphere). Because the piston 280 moves up as the liner 235 collapses, the collapse of the liner 235 takes place primarily near the piston 280, and occlusion of the sidewalls of the liner 235 during the evacuation process may be effectively prevented.

The disposal station 300 may include a pipe conduit 325, that branch from the water conduit 315 to supply cleaning water to the disposal connector 340. The pipe conduit 325 may include a valve 320 (e.g., an electric solenoid valve, or a ball valve) that controls the water flow into the interior of the disposal connector 340. After liquid is removed from the collection bag 230, clean water from the source of water 305 may flow into the interior of the disposal connector 340, which can be cycled on and off one or more times for rinsing or flushing purposes, and as preventive maintenance for the disposal connector 340. The operation may occur before the discharge connector 340 is removed from the access port 220, for example, so that cleaning water may flow to the exterior of discharge connector 340 and then be suctioned back through the interior of discharge connector by the suction of the eductor.

Thus, the disposal connector 340 may communicate with two channels: one channel that supplies clean, rinse fluid and a second channel that evacuates contaminated fluid. The second channel, for example, may be situated within the first channel, as shown in FIG. 32 and as similarly shown and described with respect to FIG. 51. A valve, such as a ball valve, is located within one of the channels. After the collected contents of a liquid collection container have been evacuated, rinse fluid flows from the first channel into and around the valve, flushing the entire surface of the valve. If the valve is a ball valve, the rinse fluid flows in a cylindrical path around the valve housing so that the valve is completely rinsed with the rinse fluid. Via the valve, the rinse fluid enters the second channel and is evacuated, similar to the contents of the liquid collection container. Thus, the second channel is also flushed with rinse fluid. This approach allows the disposal connector to automatically clean both itself and the connection with the liquid collection container. Among other things, this automatic rinse feature prevents a user from coming into contact with liquid collected in a medical procedure.

According to one aspect of the present invention, conduit 325 (which supplies cleaning water to the disposal connector 340) is in fluid communication with discharge conduit 380, which is used to "charge" the eductor 350, and to thereby suction fluid from the collection bag 30 (as described above). In this manner, cleaning fluid will not be supplied to the disposal connection 340 unless the eductor is suctioning fluid from the collection bag 30, thereby preventing unintended flooding of the collection bag 30 with cleaning water.

Once an acceptable quantity of the liquid is removed from the collection bag 230, and the collection bag 230 is collapsed, the discharge connector 340 is removed from the access port 220. The flexible valve 226 then closes the access port 220, so as to seal the collection bag 230 and to maintain the bag 230 in the collapsed state. The collection bag 230 is then removed from the container 215 and placed in a red bag for disposal, for example. A new collection bag 230' may be placed onto the container 215 for the next series of medical procedures, as shown in FIG. 33.

Figure 34:
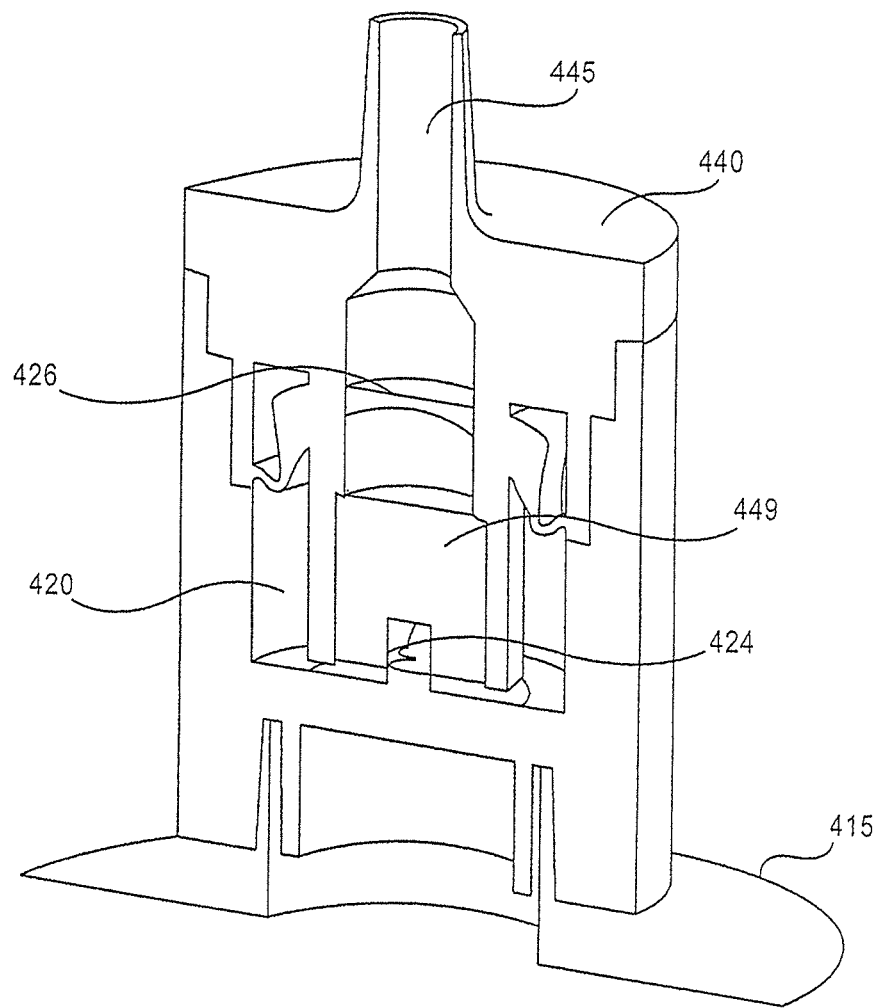
FIG. 34 is a schematic illustration of a hose junction associated with an access port of a collection bag, in accordance with aspects of the present invention.

FIG. 34 illustrates one exemplary variation of a interface 440 (or a discharge connector 340) associated with an access port 420 of a collection bag 415. The interface 440 may define a fluid passageway 445 and have a poppet valve 449 positioned at the distal end of the passageway 445, for example. The access port 420 includes a normally-closed, flexible slit valve 426 and an actuator pin 424. The exemplary slit valve 426 shown in FIG. 34 is a flexible, anti-drip, check valve. This valve may be made of a flexible material such as plastic, rubber, or other suitable material. In addition, to serving as an opening for interface 440, the valve 426 acts as a normally closed two-way check valve. The valve resists back pressure, such that it assists in maintaining vacuum pressure within the liquid collection bag. This approach assists in maintaining a previously used, evacuated bag in a substantially collapsed state. This approach further provides a safety feature by inhibiting waste in the collection bag from dripping from or exiting the bag. Thus, an evacuated collection bag will not leak waste if it is turned upside down or squeezed. When the interface 440 engages the access port 420, the actuator pin 424 engages the poppet valve 449, so as to open the fluid passageway 445 of the interface 440. Also, the distal end of the interface 440 engageably opens the slit valve 426 when the interface 440 engages the access port 420.

FIGS. 35-38 show another exemplary embodiment of a piston 580, in accordance with aspects of the present invention. As shown in FIG. 37, the piston 580 may include a main body 585 having a generally convex top surface 581. The main body 585 defines a through-hole 586 near its center, which enables a communication between the spaces above and below the piston 580. Underneath the top surface of the main body 585, the main body 585 may form a recess 582 for receiving a check valve assembly 570. The check valve assembly 570 may include a check valve 575 encased in a support structure 577. The support structure 577 may be fastened to the main body 585 via, for example, screws 573, or other attachment or adhesive features, as shown in FIG. 38.

Under certain circumstances, the liner of a liquid collection bag contained in the device may block the through-hole 586, thereby interfering with a supply of suction to the space within the cavity above the piston 580. To prevent or reduce such interference, a raised bottom 592 having a plurality of vent holes 595 may be formed or placed on the top surface 581 of the main body 585. The raised bottom 592 may be fixed to the top surface 581 via one or more screws, for example. For that purpose, as shown in FIGS. 36 and 37, the raised bottom 592 may include a plurality of screw holes 593, and the main body 585 includes a plurality of corresponding screw holes 589 aligned with the screw holes 593 of the raised bottom 592. The raised bottom 592 may also include a plurality of spacer ribs 594 extending substantially perpendicularly from its bottom surface to maintain a desired separation from the top surface 581 of the main body 585, as shown in FIG. 38. The structures in the raised bottom 592 that define the plurality of screw holes 593 may extend downwardly from the bottom surface of the raised bottom 592 and serve as additional spacers. Once the raised bottom 592 is fixed to or formed on the top surface 581 of the main body 585, the plurality of vent holes 595 communicate with the through-hole 586 of the main body 585. To uniformly supply the vacuum force to the plurality of vent holes 595, the top surface 581 of the main body 585 may define a plurality of grooves 587 extending laterally from the through-hole 586.

The piston 580 may also include one or more sealing members, such as O-rings 588 attached to an outer peripheral edge of the main body 585. The main body 585 may form one or more circumferential grooves to receive the sealing members. The piston 580 may also include a scraper ring 583 configured to prevent a liner of a liquid collection bag from being pinched between the inner wall of the cavity and the piston 580. As discussed above with reference to FIGS. 27-33, the O-rings 588 and the scraper ring 583 may be coated with a suitable material (e.g., parylene) to enhance lubricity and/or durability. In some exemplary variations, the scraper ring 583 may be pinned to or otherwise attached or adhered to the peripheral edge of the main body 585, as shown in FIG. 38. The piston and scraper ring may also comprise one continuous piece. In an alternative embodiment, the O-rings 588 and/or the scraper ring 583 may be molded into the main body 585 via, for example, a two-shot molding process, to simplify the assembly. The operational characteristics of the piston 580 are similar to those of the piston 280 described above with reference to FIGS. 27-33 and, therefore, further detailed description thereof is omitted at this point.

FIGS. 39-41 illustrate another exemplary implementation of a piston 680, consistent with aspects of the present invention. The piston 680 includes a main body 685 having a through-hole 686 and a central recess for receiving a valve assembly 675. Arrangement of the valve assembly 676 in relation to the through-hole 686 and the central recess is substantially similar to that of the variation shown in FIGS. 35-38 and, therefore, further detailed description thereof is omitted at this point.

As shown in FIG. 39, the main body 685 may include a top recess 681 having a generally convex shape. The top recess 681 may be configured to receive a sheet of material, constituting a false bottom 692, which may structurally support a liner of a liquid collection bag and maintain the liner at a desired spacing from the surface of the top recess 681. Similar to the raised bottom 592, the false bottom 692 may prevent the liner from interfering with a supply of vacuum to the space within the cavity above the piston 680. In some exemplary implementations, the false bottom 692 may be fixed onto the top recess 681 via one or more screws 693 or other attachment or adhering feature. For screw use purposes, the main body 685 may define a plurality of screw holes 684.

In the variation shown in FIG. 40, the false bottom 692 may be formed of a plastic or other suitable material mesh screwed down onto the main body 685 of the piston 680. The mesh may include a plurality of projections 695, which may collectively support the liner of a liquid collection bag. In an alternative variation, the false bottom 692 may be formed of monofilament fibers (e.g., nylon, polyester, polypropylene, PEEK, PTFE) woven into a mesh. In still another alternative variation, the false bottom 692 may be formed of a perforated sheet having a variety of perforation patterns (e.g., straight or staggered hole pattern). By way of examples only, the perforated sheet may be made of polypropylene or high strength PVC.

In one exemplary implementation, the main body 685 may be formed with a plurality of ribs extending radially from the structure delimiting the through-hole 686. The main body 685 may form a bottom recess 687. Among other things, forming the main body 685 with the plurality of ribs and the bottom recess 687 may reduce not only the amount of material for the main body 685 (thereby reducing the manufacturing cost), but also reduce the overall weight of the piston 680, which may enhance operability of the piston 680.

Figure 42:
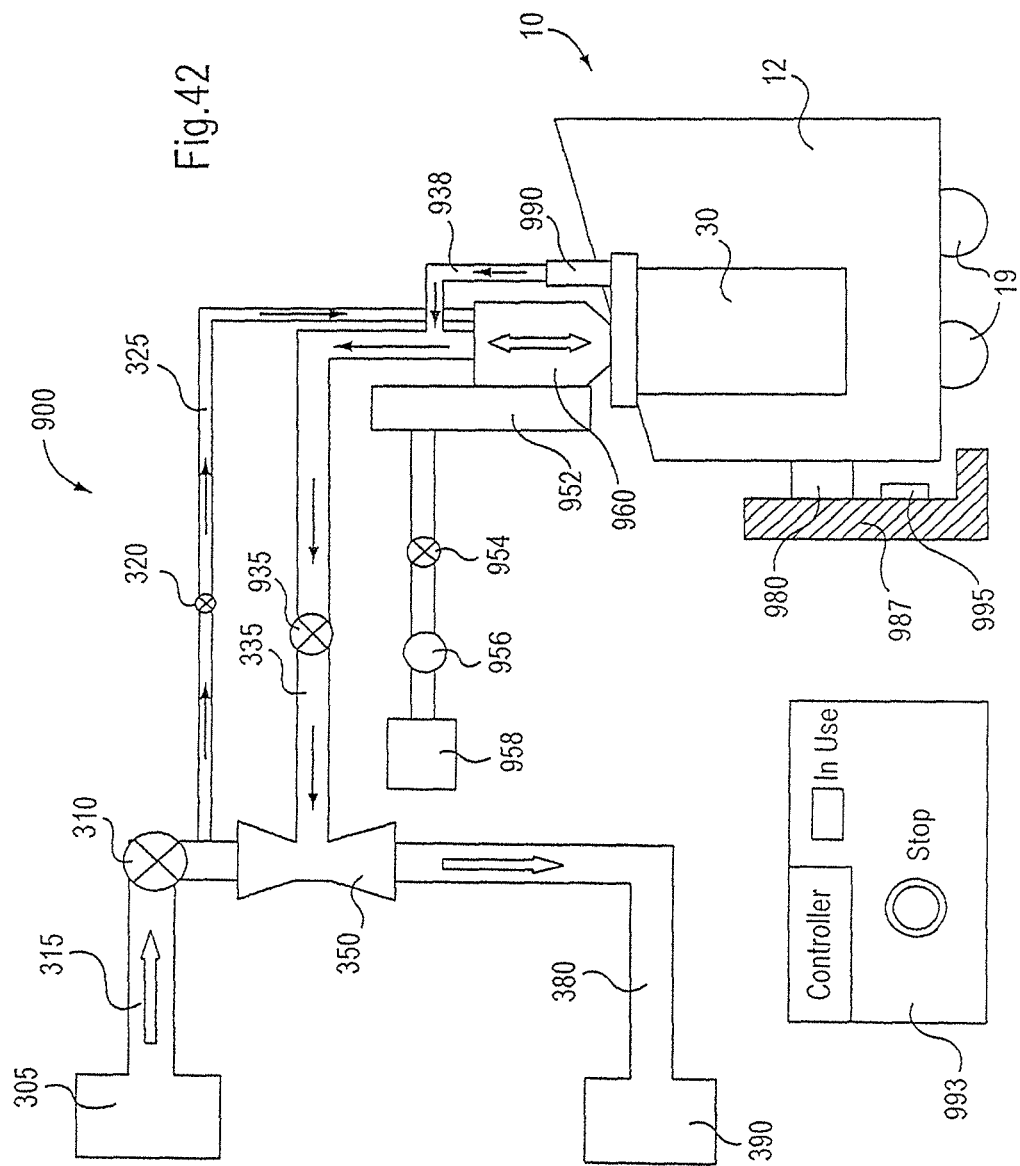
FIG. 42 is a schematic diagram of a liquid disposal station, illustrating various components and their operational characteristics associated with a liquid collection system, in accordance with aspects of the present invention.
Figure 44:
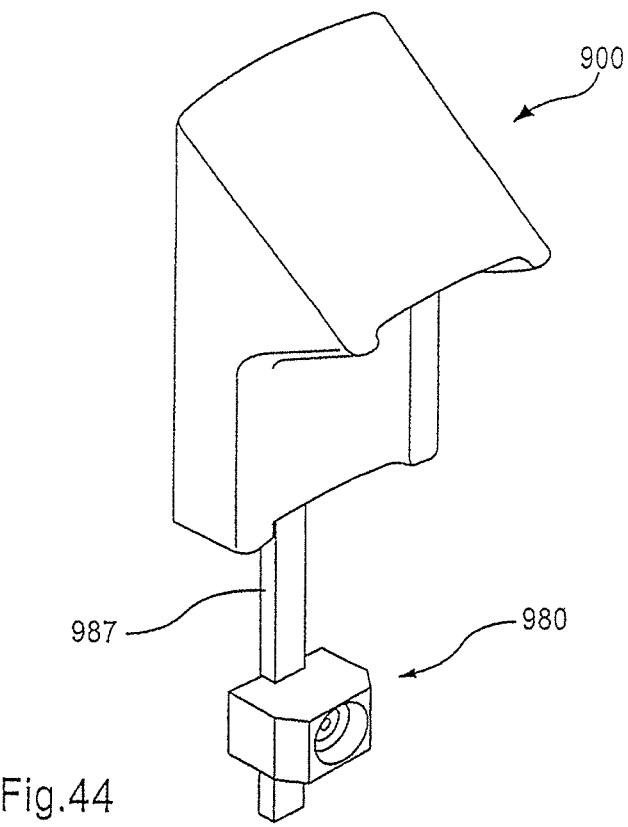
FIG. 44 is a perspective view of a liquid disposal station having a latching member (inside rectangular box) configured to engage a corresponding latching member of a liquid collection station, in accordance with aspects of the present invention.
Figure 45:
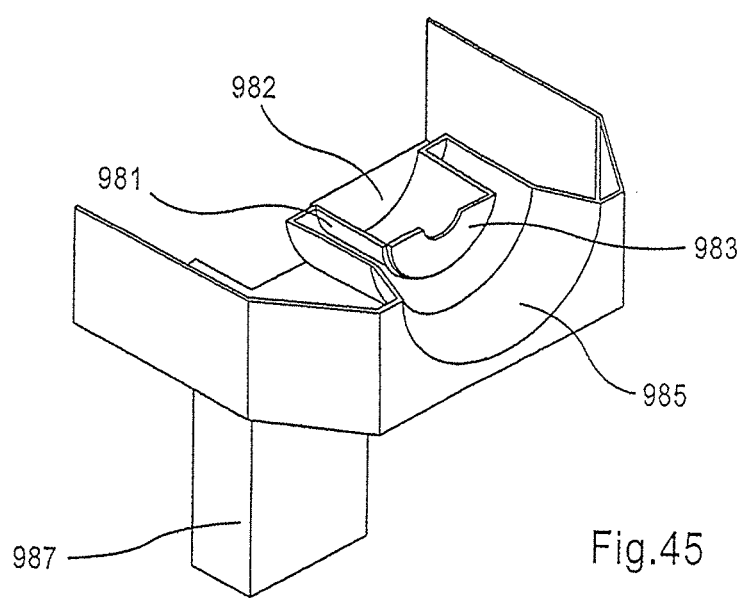
FIG. 45 is a perspective, cut-away view of the latching member of FIG. 44.

FIG. 42 is a schematic diagram of a liquid disposal station 900, illustrating various components and their operational characteristics associated with a liquid collection system 10. When the liquid collection bag becomes full or otherwise needs to be emptied, the portable liquid collection system 10 is transported to the disposal station 900, similarly to as described above with reference to FIG. 25. The disposal station 900 may include a reference structure 987 (see also FIGS. 44 and 45) and a latching member 980 fixed to the reference structure 987 for engaging a corresponding latching member 990 (see FIGS. 46 and 47) of the liquid collection system 10. Among other things, this approach allows the liquid collection system 10 to be securely and accurately positioned at a predetermined location relative to the disposal station 900. As best shown in FIG. 45, the latching member 980 of the disposal station 900 may define an internal space 982 sized and configured to receive a mechanical lock 986 (see FIG. 46) for releasably locking the latching member 990 of the liquid collection system 10. The mechanical lock 986 may include a part protruding through an opening 983 (FIG. 45). The part protruding through the opening 983 may be held by a holding member 987. The structure defining the internal space may be surrounded by an annular space 981. The latching member 980 may also include a guide structure for facilitating engagement with the latching member 990 of the liquid collection system 10. The guide structure may extend in a direction facing the liquid collection system 10 and have a generally tapered inner surface 985 and a generally tapered outer surface 984.

Figure 46:
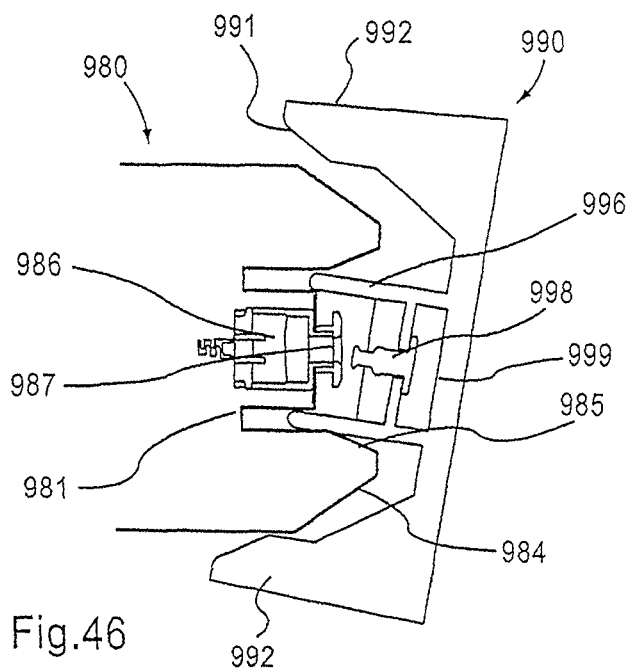
FIGS. 46 and 47 are schematic illustrations of an exemplary engagement between the latching member of the liquid disposal station and the corresponding latching member of the liquid collection system, in accordance with aspects of the present invention.
Figure 47:
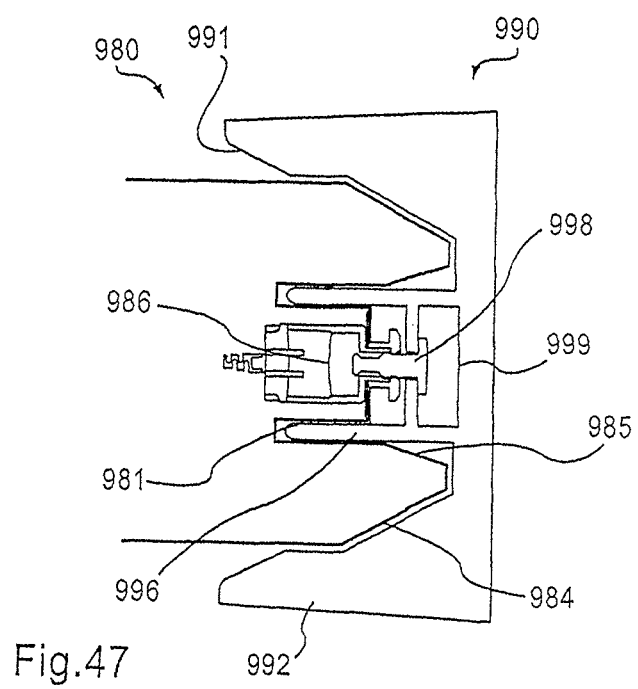

The latching member 990 of the liquid collection system 10 may include a primary lead-in structure 992 configured to receive the guide structure of the latching member 980 of the disposal station 900. The lead-in 992 may have a shape generally conforming to the shape of the guide structure. As mentioned above, the generally tapered inner and outer surfaces 984, 985 of the guide structure may facilitate alignment between the primary lead-in structure 992 and the guide structure. The lead-in structure 992 may also have an angled surface 991 for easy alignment with the guide structure. As shown in FIGS. 46 and 47, the tapered inner and outer surfaces 984, 985 of the guide structure and/or the angled surface 991 of the lead-in structure 992 may allow a greater tolerance of initial misalignment.

Figure 42C:
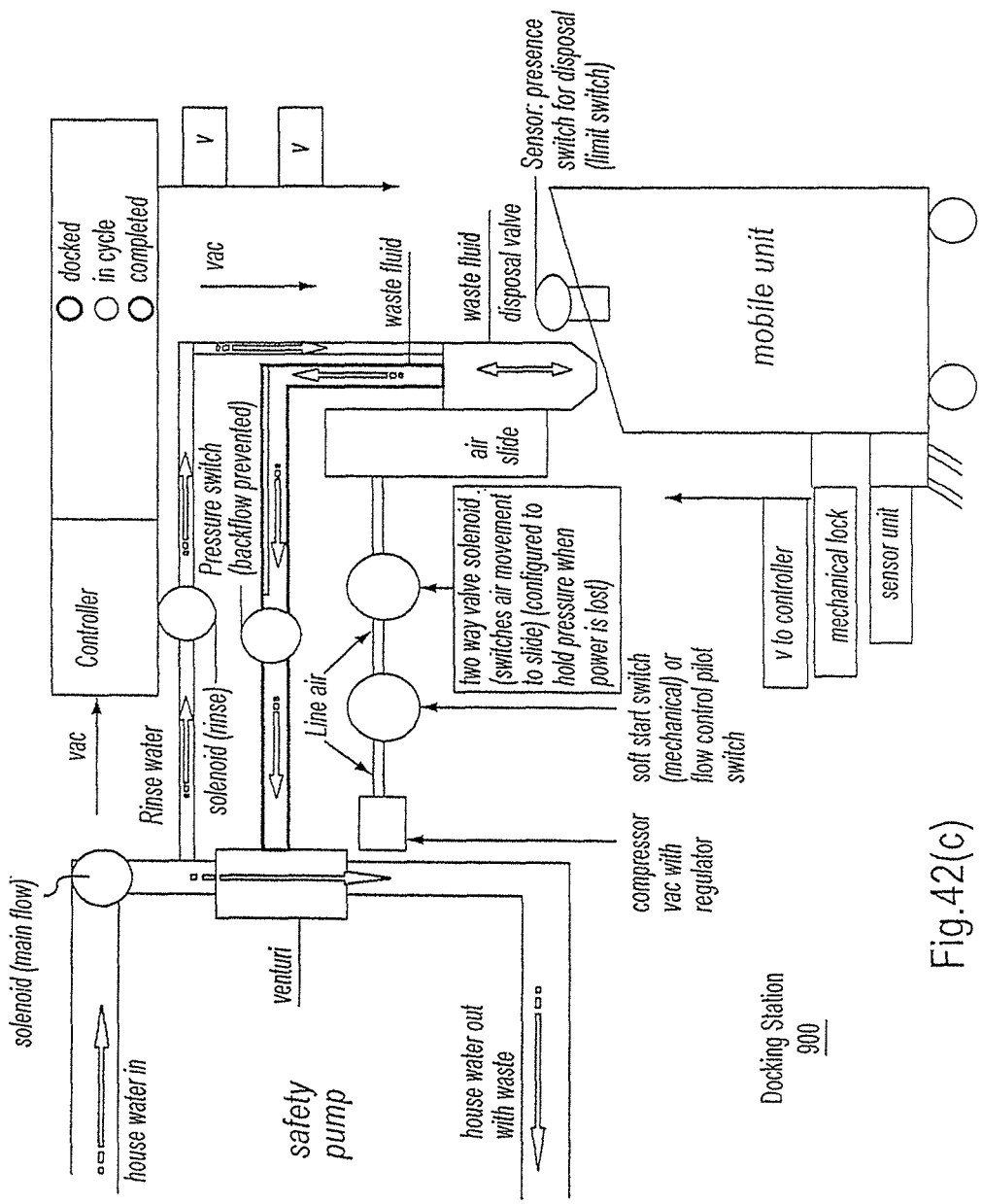
FIG. 42(c) depicts exemplary aspects of a disposal system, in accordance with aspects of the present invention.

The latching member 990 may also include a shroud 996 extending from a base of the latching member 990. A transverse wall 999 may extend across the shroud 996, and a latching post 998 may be attached to the transverse wall 999. Once the primary lead-in structure 992 is aligned with the guide structure of the disposal station 900, a further movement of the liquid collection system 10 towards the disposal station 900 causes the shroud 996 to engage the annular space 981 of the latching member 980. By the engagement with the annular space 981, the shroud 996 may guide the liquid collection system 10 into precise alignment with the disposal station 900. When the shroud 996 is fully inserted into the annular space 981, the latching post 998 may engage with the mechanical lock 986 via the opening 983, so as to securely affix the liquid collection system 10 to the disposal station 900. FIGS. 42(a) and 42(b) show an exemplary implementation of sections of the disposal station 900. FIG. 42(c) depicts exemplary features and actions of a disposal station 900.

Figure 43A:
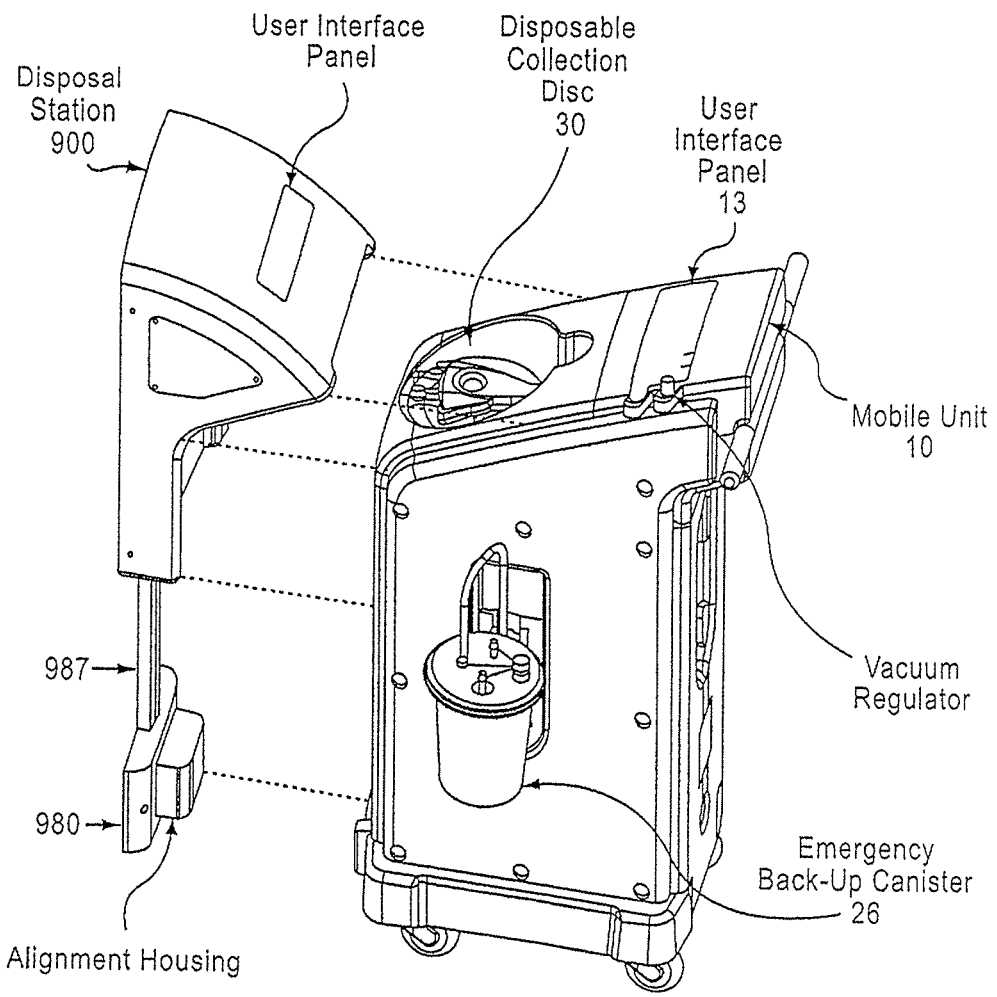

FIG. 43 shows the liquid collection system 10 fully engaged with the disposal station 900. FIGS. 43(a) and 43(b) show an exemplary implementation of a liquid collection system separated from the disposal system. In certain exemplary variations, the process for evacuating liquid from the liquid collection system 10 may be automatically initiated upon engagement between the latching stud 998 and the mechanical lock 986, although the system may be configured such that an operator is required to manually initiate the evacuation process after the system 10 has been operatively engaged with the disposal station 900.

The disposal station 900 may include a sensor unit 995 affixed to, for example, the reference structure 987 and configured to detect the presence of a liquid collection system 10 in the vicinity of the disposal station 900. The disposal station 900 may be configured such that the presence of a liquid collection system 10 in the disposal station 900 is confirmed by the sensor unit 995 prior to initiation of a liquid evacuation process. Thus, the sensor unit 995 may be used as a safety measure against a false initiation of a liquid evacuation process in the disposal station 900.

Figure 48:
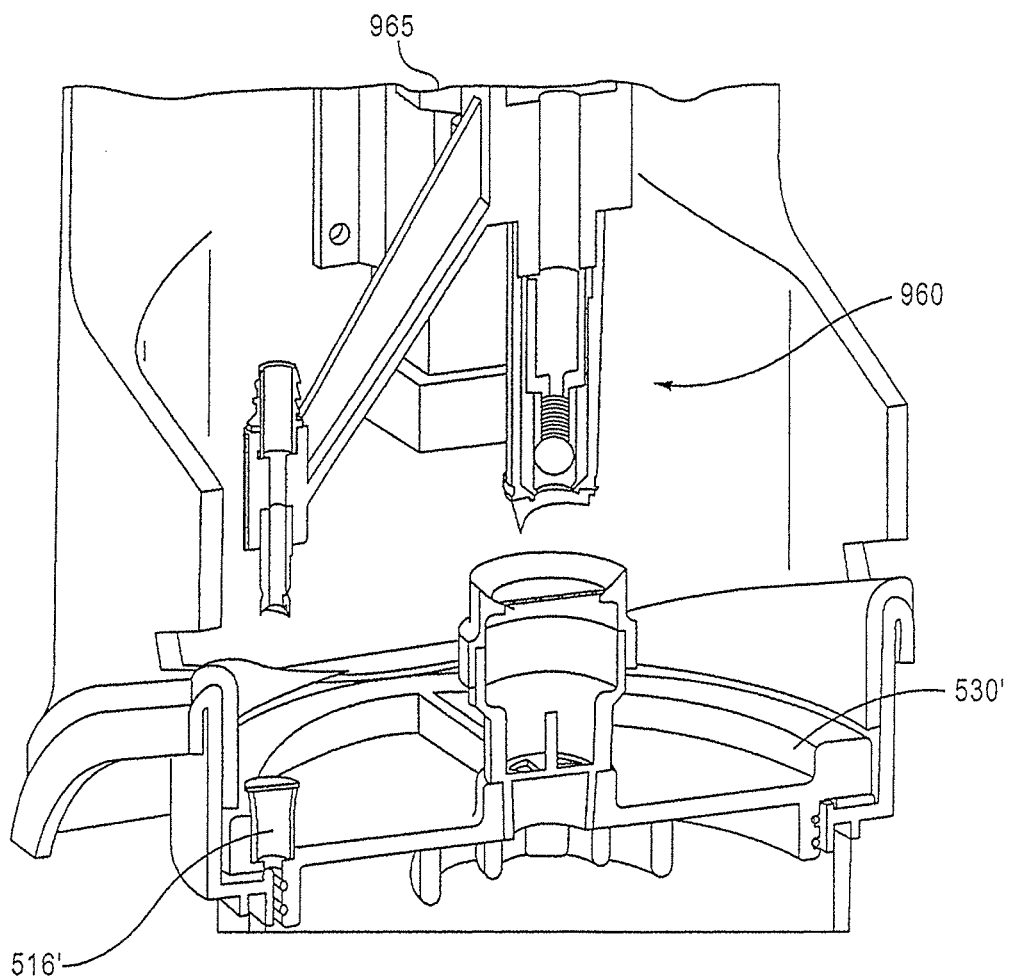

When the liquid collection system 10 is securely positioned in the disposal station, an evacuation interface 960 and an interstitial interface 970 may align with the evacuation port 540' and the interstitial port 516', respectively, of the liquid collection system 10, as shown in FIG. 48. Use of an interstitial interface is optional. The disposal station may also be configured to function without any interstitial connection or interstitial suction. In an exemplary implementation, the interstitial interface 970 may be connected to the evacuation interface 960 via a rigid support 965. The evacuation interface 960 and the interstitial interface 970 may be connected to a suitable draining system for evacuating the liquid from the liquid collection system. In some exemplary variations, the draining system for the disposal station may include an eductor 350 that provides a source of suction pressure sufficient to draw the collected liquid out of the collection bag of a liquid collection system 10, as shown in FIG. 42. The eductor 350 and the associated flow connections for evacuating the collected liquid may operate similarly to those described above with reference to FIGS. 31 and 32, for example.

Figure 52:
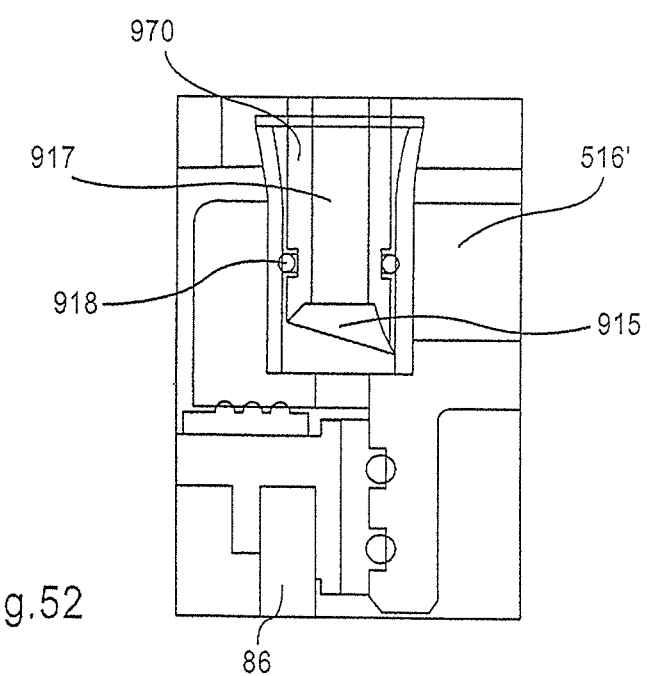
FIG. 52 is a cross-sectional view of the interstitial hose junction of FIG. 48 in engagement with an interstitial port of the lid.

The flow connection between the eductor 350 and the liquid collection bag 30 in the disposal station may differ from that shown in FIGS. 31 and 32, in that this variation includes a side conduit 938 branching from the evacuation conduit 335 for supplying suction force to the interstitial interface 970. The interstitial interface 970 is configured to connect to an interstitial port 516' formed on a lid 530' of a liquid collection bag 30, as shown in FIGS. 48 and 52. As noted above, the interstitial interface is optional, and the disposal system may be configured to function without any vacuum pressure from an interstitial vacuum. For example, when the interstitial hose junction 970 is inserted into the interstitial port 516', the passageway 917 of the interstitial interface 970 may communicate with the interstitial space, as shown in FIG. 52. A suitable sealing member 918 (e.g., an O-ring) may be provided to seal the gap between an interior surface of the interstitial port 516' and an exterior surface of the interstitial interface 970. As mentioned above with reference to FIGS. 20-22, the interstitial port 516' of the lid 530' may be in fluid communication with an interstitial space within a cavity external to a liquid collection bag, and the supply of a suction force to the interstitial space may equalize the pressure inside and outside of the collection bag during an evacuation process, so that the collection bag may remain substantially uncollapsed during the evacuation process. Providing the interstitial port 516' in the lid 530' may eliminate the need for a power supply in the liquid collection system 10 during the evacuation process, which may otherwise be required to supply suction source to the interstitial space, similarly to the function of the second vacuum connector 64 in FIG. 12. In other variations, a seal between the lid of the liquid collection bag and the top 11 of cavity 15 and at least seal between the piston and the inner walls of the cavity maintain vacuum pressure on the outside of the collection bag by preventing air from entering the interstitial space so that the sides of the bag do not collapse during an evacuation process. By limiting air flow into the interstitial space between the bag and the inner walls of the cavity, communication between a suction source and the interstitial space is unnecessary/optional during an evacuation process. In addition, air flow into the interstitial space may be controlled via the check valve 575 in the piston. These seals assist in equalizing the pressure inside and outside of the collection bag during a collection process and continue to maintain that pressure up through at least part of an evacuation process.

In exemplary variations, air flow may be allowed into the interstitial space near the end of an evacuation process in order to fully collapse the liquid collection bag 30 by allowing communication between the atmosphere and interstitial space. For example, air may be allowed into the interstitial space at a predetermined time in the disposal cycle, such as during approximately the last 30 seconds of an evacuation cycle. In an exemplary implementation, the interstitial space may be accessed by establishing communication with the interstitial port 516' and the atmosphere. For example, the disposal station may pierce the breakable piece in the interstitial port 516' in order to allow air to flow into the interstitial space near the end of the evacuation process. The docking station may include a timer that times the evacuation process and establishes communication with the interstitial space at a predetermined amount of time before the end of the evacuation cycle.

In other variations, a valve, such as a solenoid valve or electric valve, may be employed to provide air flow into the interstitial space near the end of an evacuation process. However, using the docking station to establish atmospheric communication with the interstitial space enables a disposal cycle to run on an unpowered liquid collection container and mobile unit.

According to certain exemplary embodiments, the disposal station may include a linear slide 952, along which the evacuation interface 960 and the interstitial hose junction 970 may slidably engage the evacuation port 540' and the interstitial port 516', respectively. Movement of the evacuation interface 960 and the interstitial interface 970 relative to the linear slide 952 may be controlled, for example, pneumatically by a compressor 958 or other suitable movement mechanism, a flow control pilot 956, and a flow control valve 954 (e.g., a two-way solenoid valve), similarly to as shown and described in FIG. 42. The flow control valve 954 may be configured to maintain pressure when power is lost. Alternatively, junction 960 and junction 970 may be controlled, either automatically or manually, by any other linear actuation device.

As best shown in FIGS. 48 and 48(*a*), the evacuation port 540' and the interstitial port 516' may remain closed by breakable closure members 544', 514' during the liquid collection process. These breakable closure members 544', 514' may be pierced or broken when the evacuation interface 960 and the interstitial interface 970 engage the evacuation port 540' and the interstitial port 516'. To facilitate such piercing, the evacuation interface 960 and the interstitial interface 970 may each include a sharp distal edge 966, 915.

Figure 49A:
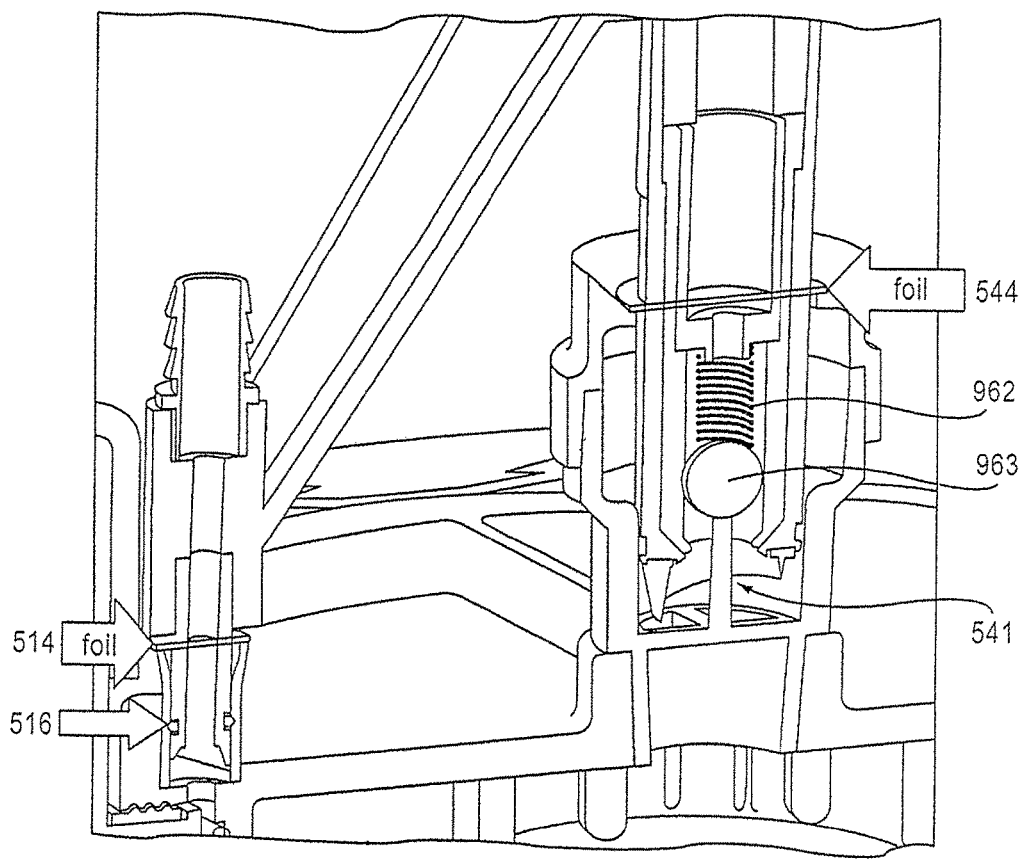
Figure 49B:
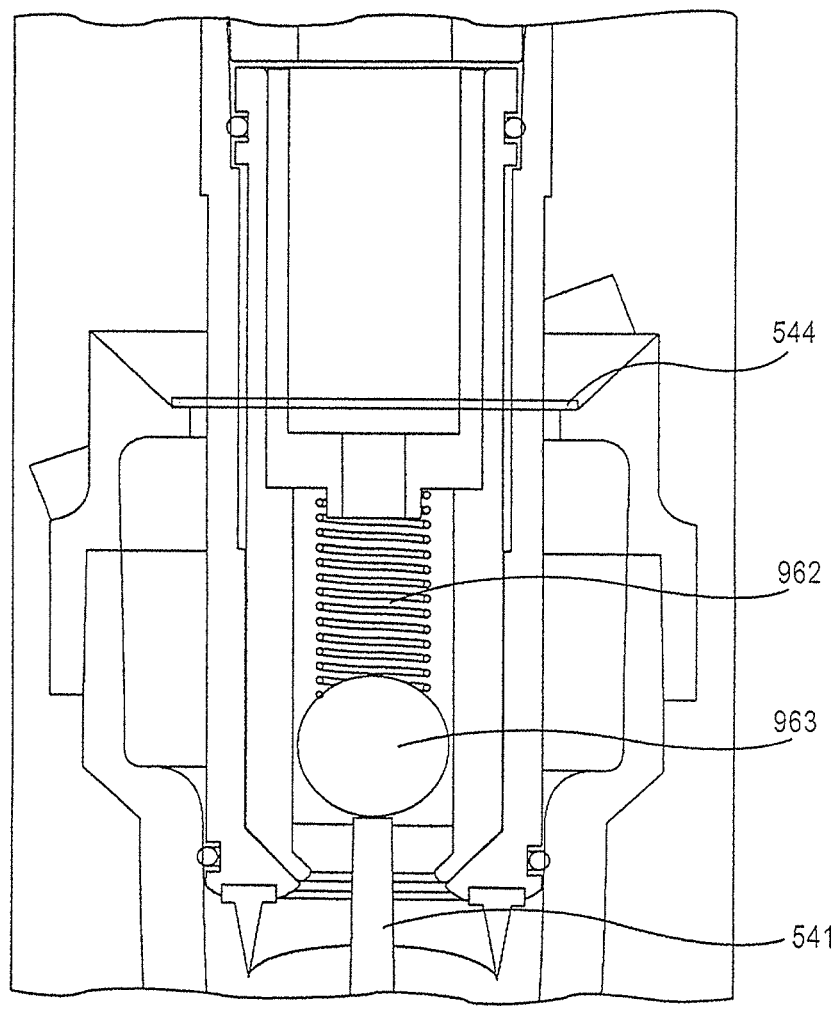

As shown in FIGS. 49 and 50, the evacuation interface 960 may include a normally-closed valve 962, 963 (e.g., a duckbill valve, a check valve, a spring-loaded valve, a poppet valve) to open and close its passageway. In the exemplary variation shown in FIGS. 49, 49(*a*), 49(*b*), and 50, the valve includes a ball 963 biased against a distal end of the hose junction 960 by a spring 962. The valve 962, 963 may be opened from its normally-closed position by an actuation rod or pin 541' positioned inside the evacuation port 540', for example.

Figure 51:
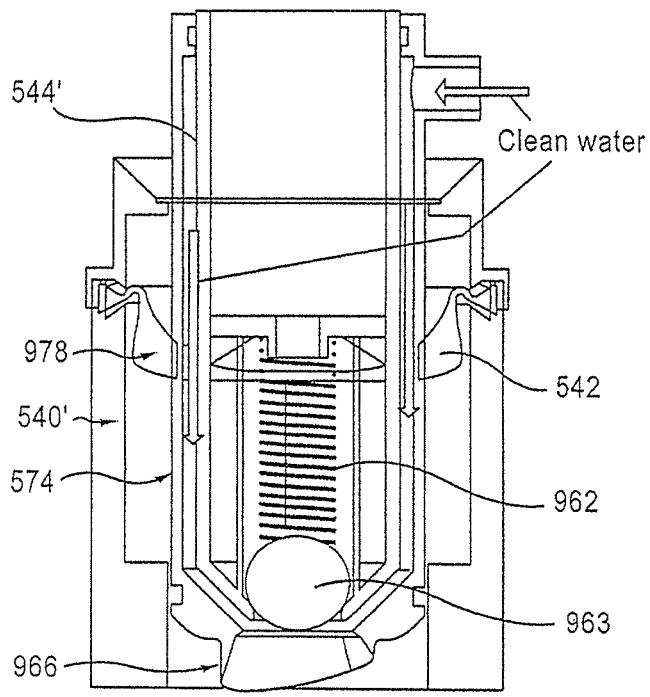
FIG. 51 is a cross-sectional view of the disposal hose junction and valve of FIGS. 49 and 50 in engagement with the evacuation port, illustrating an exemplary flow of cleaning water for cleaning the hose junction, in accordance with aspects of the present invention.

Thus, upon insertion of the valve 962, 963 into the evacuation port 540', the actuator pin 541' engages the valve 962, 963 so as to open the passageway of the evacuation hose junction 960, as shown in FIG. 50. The evacuation port 540' may include a normally-closed, flexible valve 542, as shown in FIG. 51. The valve 542 may be similar to the slit valve 426 described above with reference to FIG. 34 and, therefore, further detailed description thereof is omitted at this point. When the evacuation interface 960 is inserted into the evacuation port 540', the valve 542 may be deflected to open the evacuation port 540', for example.

FIG. 51 is a cross-sectional view of the evacuation interface 960 in engagement with the evacuation port 540', illustrating an exemplary flow of cleaning water for cleaning the interface 960. As shown in FIG. 42, the disposal station 900 may include a pipe conduit 325, branching from the water conduit 315, to supply cleaning water or other cleaning substance to the evacuation hose junction 760. After liquid is removed from a collection bag, clean water or other substance from the pipe conduit 325 may flow into the interior of the evacuation hose junction 760 through a cleaning chamber 974, which can be cycled on and off one or more times to rinse or flush it off as a preventive maintenance for the evacuation interface 760. The cleaning operation may be performed before the evacuation interface 760 is removed from the evacuation port 540' so that cleaning substance may flow to the exterior of the evacuation interface 760 and then be suctioned back through the interior of the evacuation interface 760, thereby flushing any residual fluid or other particles from the components of the interior of the interface 760.

The disposal station 900 may include an interface board 993 for indicating the status of the disposal station 900 and/or for enabling control of various features of the disposal station 900. For example, as shown in FIG. 42, the interface board 993 may include a stop button for stopping a liquid evacuation process. The interface board 993 may also include one or more visual or audible indicators that provide various information relating to its operational characteristics and/or status, such as, for example, whether the station is being used.

Figure 2A:
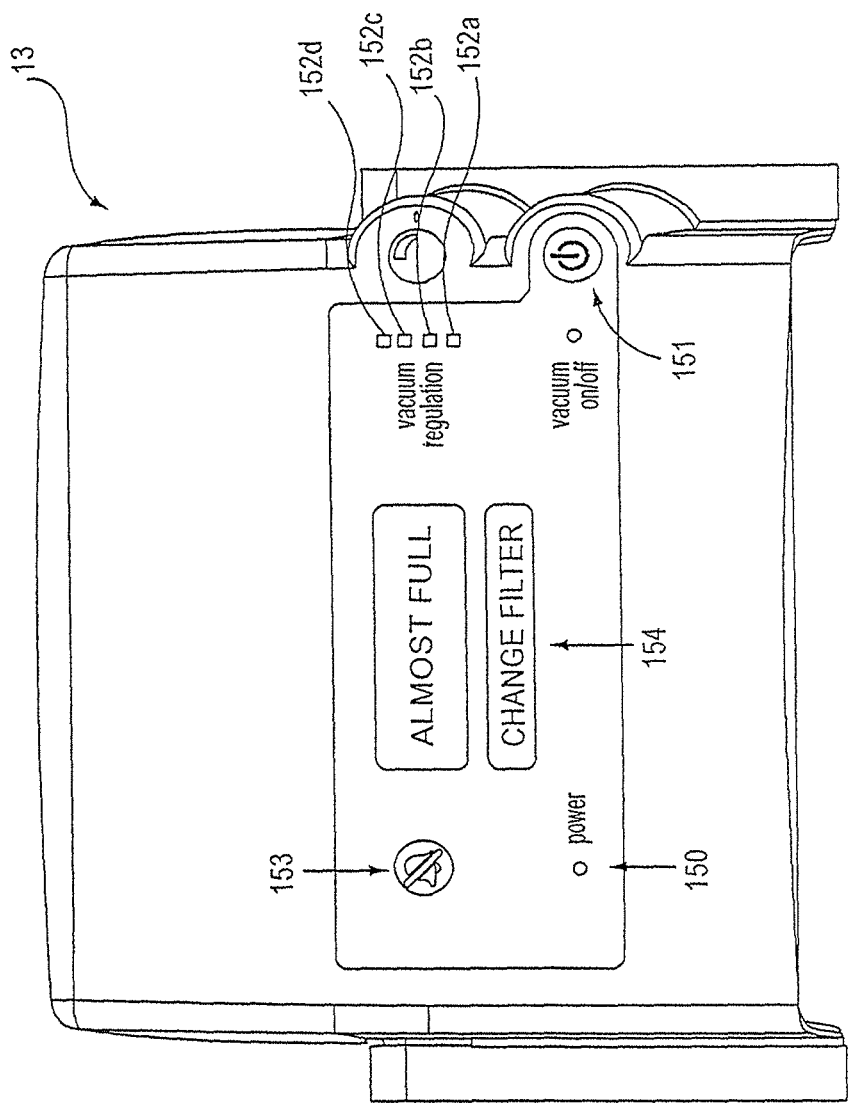
FIG. 2(a) is a partial perspective view of another exemplary embodiment of an interface board.

An exemplary implementation of aspects of the present invention may include a fluid collection system that includes a mobile unit and a disposable fluid collection container. The mobile unit may include a user interface; for example, as shown in FIG. 2*a*, and a cavity, for example as shown in FIG. 4, with the cavity being configured to receive the disposable fluid collection container. The top portion of the cavity may include an interface connector, such as a flexible flange 81 shown in FIG. 4. The mobile unit may include a vacuum pump, HEPA filter(s)/trap(s), a piston, a piston check valve, along with other features, such as those illustrated in FIGS. 11(*a*-*c*).

The piston may be located in the cavity of the mobile unit, as shown with regard to piston 280 in FIG. 22(*a*). The piston may further include a scraper ring abutting the interior walls of the cavity, at least one O-ring sandwiched between the sides of the piston and the interior of the cavity, and a check valve assembly, such as the check valve shown in FIGS. 35-38.

The mobile unit may also include an attachment piece for attaching a back-up container, including a vacuum port on the side of the mobile unit for supplying suction to the back-up container.

Figure 53:
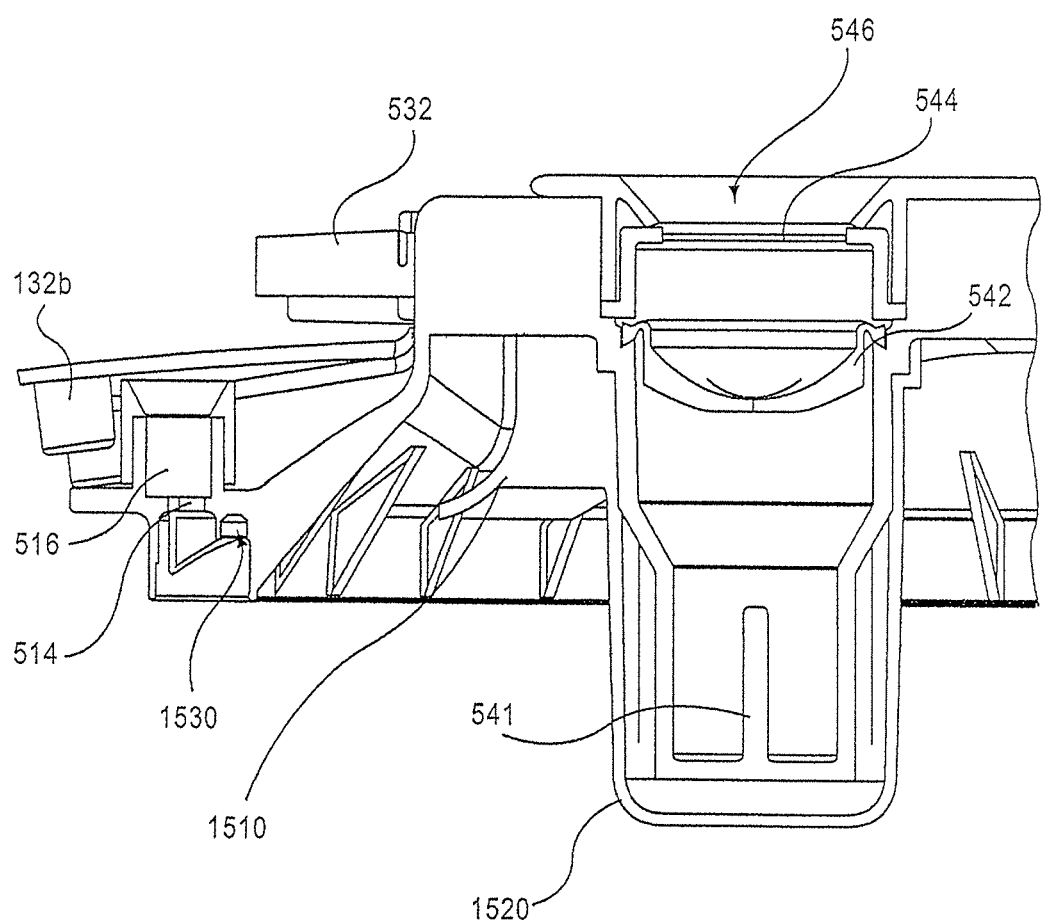
FIGS. 53-55 show exemplary illustrations of a lid in accordance with aspects of the present invention.
Figure 54:
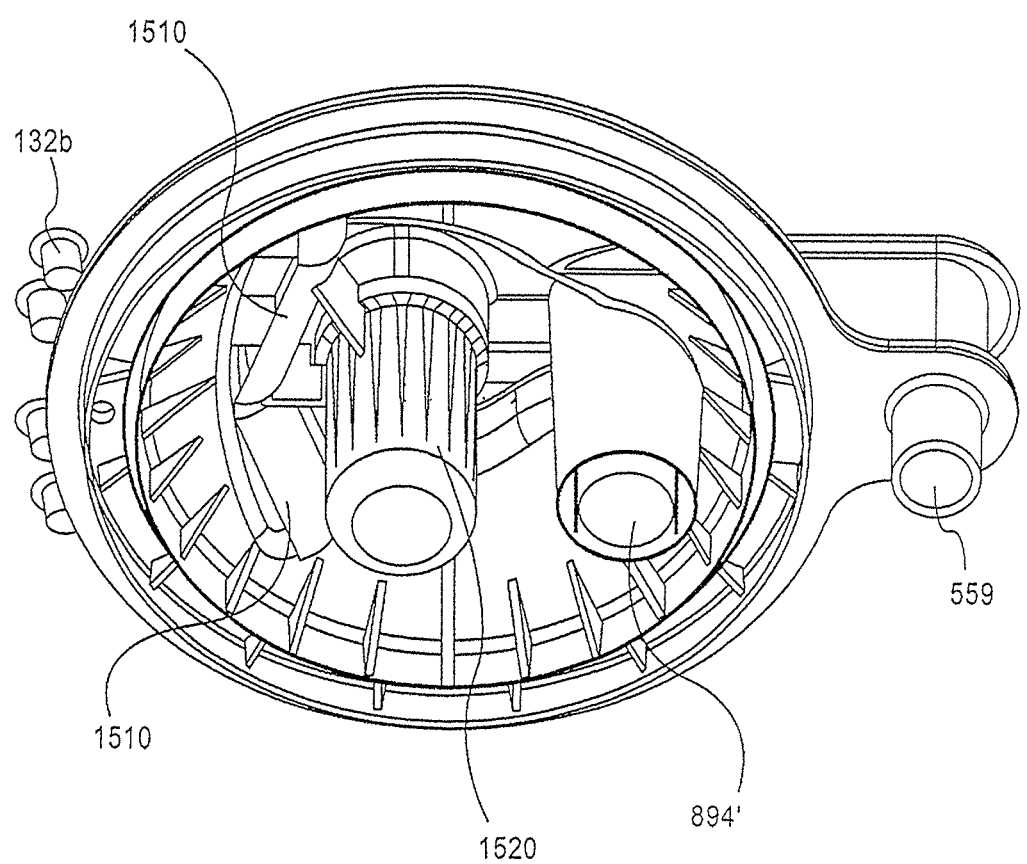
Figure 55:
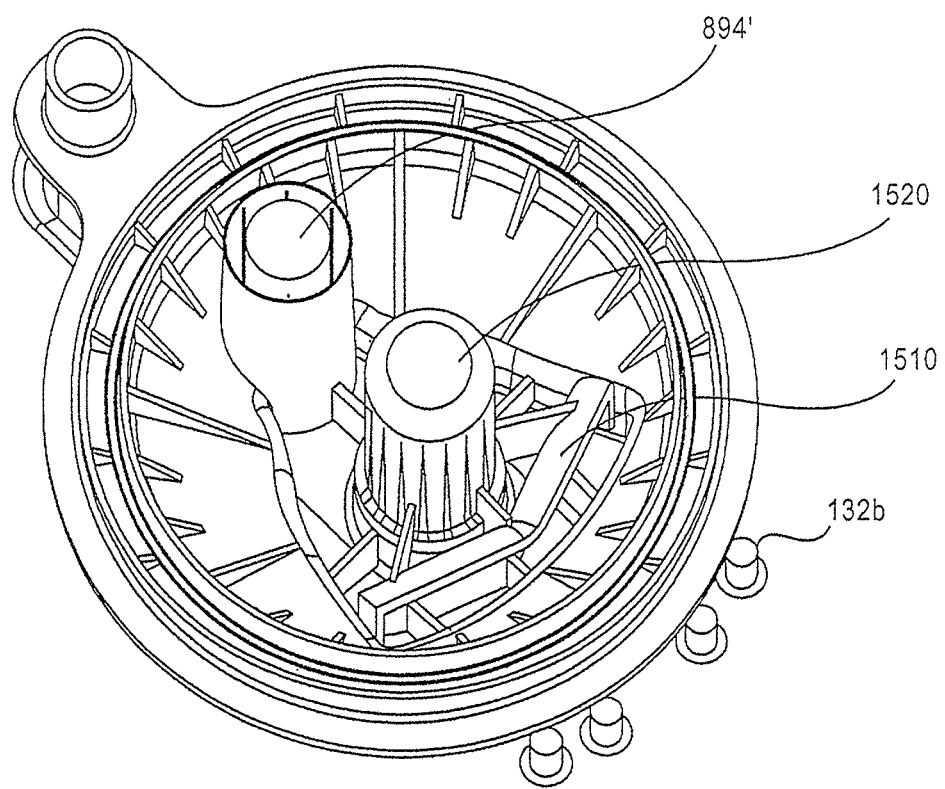

The fluid collection container may include a collapsible liner similar to element 35 in FIG. 10 and a lid, such as the lid illustrated in FIGS. 53-55. As illustrated, the lid may include an opening 546 configured to provide communication with an evacuation source. The opening may include a breakable member, a two-way check valve, and a pin. The lid may also include an interstitial opening for communicating atmospheric pressure, for example, with an interstitial space between the cavity and liner, wherein the interstitial opening is closed by a breakable member. The lid may also include a plurality of ports, each being configured to communicate with a suction instrument, through which fluid is drawn into the fluid collection container. Each port may include a tethered cap. The lid may include a shelf located between the interior opening of the plurality of ports and the opening communicating with the vacuum source to divert collected fluids away from the vacuum source. The lid may also include a screen surrounding the opening to the evacuation opening. The lid may also include additional features illustrated in FIGS. 53-55.

The liner may be attached to the lid via hot melt. Prior to use, the liner may also include a breakable band that maintains the liner in a collapsed position against the lid.

In order to use the fluid collection system in this variation, a user places a disposable fluid collection container in the top of the cavity of the mobile unit. When the lid is attached to the mobile unit, communication is established via a vacuum interface between a space created by the interior of the collapsible liner and the lid, and a vacuum source. A valve, such as a PPV type valve, may be included within a portion of the lid, blocking liquid from entering the vacuum interface.

When the vacuum source is turned on, the vacuum source is communicated with the interstitial space between the exterior of the collapsible liner and the interior of the cavity. This vacuum pressure breaks the band on the fluid collection container, draws the piston down to a first position, and expands the collapsible liner into the cavity, for example, as shown in FIGS. 28 and 29. Vacuum pressure is maintained in the interstitial space by at least one of a seal located between the top of the cavity and the lid, the at least one O-ring sandwiched between the piston and the cavity, and the piston check valve in the center of the piston.

Fluid to be collected is drawn through at least one port in the lid into the expanded liner using the vacuum source. Fluid fills the liner, for example, as shown in FIGS. 29 and 30 The PPV valve prevents fluid from entering the vacuum source.

At the end of a procedure or when use of the liquid collection container is otherwise discontinued (e.g., when full), the mobile unit may be transported to and docked with a disposal station, for example, as illustrated in FIG. 43. The mobile unit may include an attaching mechanism, for example, as shown in FIGS. 44-47, that is configured to secure the mobile unit to the disposal station during a disposal cycle. The disposal station may detect the engagement of a mobile unit and begin an automatic disposal cycle. The disposal station may also include a user interface, for example, as illustrated in FIG. 26(a), and connections to a water supply and waste depository, such as illustrated in FIGS. 42(a-b). The disposal cycle may proceed as described in connection with FIGS. 23, 42, and 42(c).

The disposal station may include an evacuation interface configured to communicate with the lid of the fluid collection device, such as is illustrated in FIG. 51. The evacuation interface pierces the breakable member in the lid, and pushes open a two-way check valve in the lid. A ball biased against the opening of the evacuation interface is pressed away from the opening by a pin in the lid, thereby opening the evacuation interface.

Suction is applied, for example, using an eductor to evacuate the contents of the fluid collection container via the evacuation interface. As the contents are evacuated, the piston moves to a second position (e.g., rises), as shown, for example, in FIGS. 31-32 and the liner collapses. A displacement mechanism, for example, as illustrated in FIGS. 29(a)-32(a) may be provided in the interior of the cavity to prevent the liner from being caught between a stopper and the piston. Near the end of the disposal cycle, a breakable member closing an opening in the lid that communicates the atmosphere with the interstitial space between the cavity and the liner may be pierced, allowing pressure regulation between the interstitial space and atmospheric pressure and allowing the liner to fully evacuate.

The disposal station may be configured to include two channels: one channel that supplies clean, rinse fluid, and a second channel that evacuates contaminated fluid. The second channel, for example, may be situated within the first channel, as shown in FIG. 32 and as similarly shown and described with respect to FIG. 51. A valve, such as a ball valve, may be located within one of the channels. After the collected contents of a liquid collection container have been evacuated, rinse fluid flows from the first channel into and around the valve, flushing the entire surface of the valve. If the valve is a ball valve, the rinse fluid flows in a cylindrical path around the valve housing so that the valve is completely rinsed with the rinse fluid. Via the valve, the rinse fluid enters the second channel and is evacuated, similar to the contents of the liquid collection container. Thus, the second channel is also flushed with rinse fluid. This approach allows the disposal connector to automatically clean both itself and the connection with the liquid collection container.

At this point, the mobile unit may be disconnected from the disposal station, the disposable fluid collection container may be removed and discarded, and a new disposable fluid collection container may be inserted to prepare the fluid collection system for another procedure.

While aspects of the present invention have been described and illustrated with reference to one or more preferred variations thereof, it is not the intention of the applicants that these aspects be restricted to such detail. Rather, it is the intention of the applicants that aspects of the present invention be defined by all equivalents, both suggested hereby and known to those of ordinary skill in the art, of the variations falling within the scope thereof.

We claim:

1. A fluid collection system, comprising:
    a container having a top opening;
    a lid configured to close the top opening;
    and a flexible liner attached to the lid such that the liner is interposed between the lid and the container when the lid closes the top opening, the liner and the lid defining a substantially sealed interior space therebetween,
    wherein the lid includes an access port through which the interior space receives fluid,
    wherein the flexible liner is configured to collapse into an at least partially collapsed state as the fluid is removed from the interior space, and
    wherein the container receives air through a container access port into a space between an interior of the container and an exterior of the liner as the fluid is removed from the interior space.

2. The fluid collection system according to claim 1, further comprising:
    a seal located between the top opening of the container and the lid, wherein the seal prevents air from entering the space between the interior of the container and the exterior of the liner.

3. The fluid collection system according to claim 2, further comprising:
    a piston located in the container below the flexible liner; and
    at least one seal located between the edge of the piston and the interior of the container, wherein the seal prevents air from beneath the piston from entering the sealed portion of the container above the piston.

4. The fluid disposal system of claim 1, further comprising:
    a pumping assembly having a discharge connector configured to mate with an access port of the lid.

5. The fluid disposal system of claim 1, wherein the access port through which the interior space receives fluid is the same as the access port with which the discharge connector is configured to mate.

6. The fluid disposal system of claim 1, wherein the access port through which the interior space receives fluid is separate from the access port with which the discharge connector is configured to mate.

7. A fluid collection system, comprising:
a disposable collection container; and
a disposable collection container receiving housing, the housing including:
 a cavity;
 a suction source; and
 a user interface,
the disposable collection container including:
 a lid configured to attach to the housing;
 an interface configured to communicate with the suction source; and
 a collapsible liner attached to the lid, such that the lid and collapsible liner form a substantially sealed interior space, and wherein the liner is configured to be expandable within the cavity, and
 wherein the housing further includes a communication interface between the suction source and the interior of the cavity, wherein when the communication interface is open, communication with the suction source produces expansion of the liner within the cavity.

8. The fluid collection system according to claim 7, wherein the interface configured to communicate with the suction source includes a valve configured to prevent fluid from entering the suction source once the valve is in contact with liquid.

9. The fluid collection system according to claim 8, wherein the valve is a float ball type valve.

10. The fluid collection system according to claim 8, wherein the valve includes a hydrophilic material.

11. The fluid collection system according to claim 7, further comprising:
a seal located between the cavity and the lid of the disposable collection container, wherein the seal is configured to prevent air from entering the interior of the cavity.

12. The fluid collection system according to claim 11, further comprising:
a piston located in the cavity and proximate to the disposable collection container; and
at least one seal located between the piston and the cavity, wherein the at least one seal is configured to prevent air from beneath the piston from entering the space in the cavity between the piston and the disposable collection container.

13. The fluid collection system according to claim 12, further comprising:
a valve in the piston, wherein the valve is configured to allow air to be evacuated from the space in the container between the disposable collection container and the piston and to prevent air from beneath the piston from entering the space in the cavity between the disposable collection container and the piston.

14. The fluid collection system according to claim 12, wherein the collection device further comprises:
a displacement mechanism configured to displace the liner from the interior side of the cavity when the piston is moved to a first position.

15. The fluid collection system according to claim 7, wherein the housing further comprises:
an attachment section configured to attach an overflow container to the housing.

16. The fluid collection system according to claim 7, wherein the housing further comprises:
a base located beneath the cavity, the base having a plurality of wheels.

17. The fluid collection system according to claim 16, wherein the base includes a securing mechanism configured to removably attach the housing to a disposal system.

18. The fluid collection system according to claim 7, wherein the lid of the disposable collection container comprises an interstitial opening configured to allow communication with an interstitial space between the interior of the cavity and the exterior of the flexible liner.

19. The fluid collection system according to claim 7, wherein the lid of the disposable collection container comprises:
an opening configured for communication with at least one suction instrument through which the disposable collection container is able to receive fluid.

20. The fluid collection system according to claim 19, wherein the lid of the disposable collection container further comprises:
an opening configured for communication with a disposal device; and
a safety mechanism configured to prevent fluid from exiting the opening configured to communicate with a disposal device unless communication with the disposal device is established.

21. The liquid collection system according to claim 20, wherein the safety mechanism includes a check valve.

* * * * *